(12) United States Patent
Kallen et al.

(10) Patent No.: US 12,337,031 B2
(45) Date of Patent: *Jun. 24, 2025

(54) COMBINATION VACCINE

(71) Applicant: CureVac AG, Tübingen (DE)

(72) Inventors: Karl-Josef Kallen, Königsdorf (DE);
Thomas Kramps, Tübingen (DE);
Margit Schnee, Constance (DE);
Daniel Voss, Tübingen (DE)

(73) Assignee: CureVac SE, Tübingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/590,173

(22) Filed: Feb. 1, 2022

(65) Prior Publication Data

US 2022/0152193 A1    May 19, 2022

Related U.S. Application Data

(60) Division of application No. 16/781,781, filed on Feb. 4, 2020, now Pat. No. 11,266,735, which is a division of application No. 15/048,561, filed on Feb. 19, 2016, now Pat. No. 10,588,959, which is a continuation of application No. PCT/EP2014/002302, filed on Aug. 21, 2014.

(51) Int. Cl.
| | |
|---|---|
| *A61K 39/155* | (2006.01) |
| *A61K 39/12* | (2006.01) |
| *A61K 39/145* | (2006.01) |
| *C07K 14/005* | (2006.01) |
| *C12N 7/00* | (2006.01) |
| *A61K 39/00* | (2006.01) |

(52) U.S. Cl.
CPC ............ *A61K 39/155* (2013.01); *A61K 39/12* (2013.01); *A61K 39/145* (2013.01); *C07K 14/005* (2013.01); *C12N 7/00* (2013.01); *A61K 2039/53* (2013.01); *A61K 2039/572* (2013.01); *A61K 2039/575* (2013.01); *C12N 2760/16134* (2013.01); *C12N 2760/18534* (2013.01)

(58) Field of Classification Search
None
See application file for complete search history.

(56) References Cited

U.S. PATENT DOCUMENTS

| | | |
|---|---|---|
| 8,217,016 B2 | 7/2012 | Hoerr et al. |
| 8,383,340 B2 | 2/2013 | Ketterer et al. |
| 8,703,906 B2 | 4/2014 | Baumhof et al. |
| 8,968,746 B2 | 3/2015 | Baumhof et al. |
| 9,155,788 B2 | 10/2015 | Hoerr et al. |
| 9,226,959 B2 | 1/2016 | Kramps et al. |
| 9,234,013 B2 | 1/2016 | Thess et al. |
| 9,314,535 B2 | 4/2016 | Baumhof et al. |
| 9,352,028 B2 | 5/2016 | Barner et al. |
| 9,402,887 B2 | 8/2016 | Probst et al. |
| 9,421,255 B2 | 8/2016 | Baumhof et al. |
| 9,433,669 B2 | 9/2016 | Hoerr et al. |
| 9,433,670 B2 | 9/2016 | Hoerr et al. |
| 9,439,956 B2 | 9/2016 | Hoerr et al. |
| 9,447,431 B2 | 9/2016 | Thess et al. |
| 9,463,228 B2 | 10/2016 | Hoerr et al. |
| 9,572,874 B2 | 2/2017 | Fotin-Mleczek et al. |
| 9,616,084 B2 | 4/2017 | Mutzke |
| 9,623,095 B2 | 4/2017 | Kallen et al. |
| 9,655,955 B2 | 5/2017 | Hoerr et al. |
| 9,669,089 B2 | 6/2017 | Thess et al. |
| 9,683,233 B2 | 6/2017 | Thess |
| 9,688,729 B2 | 6/2017 | Kramps et al. |
| 9,737,595 B2 | 8/2017 | Lorenz et al. |
| 9,839,697 B2 | 12/2017 | Thess et al. |
| 9,890,391 B2 | 2/2018 | Thess et al. |

(Continued)

FOREIGN PATENT DOCUMENTS

| | | |
|---|---|---|
| WO | WO 2002/085434 | 10/2002 |
| WO | WO 2003/059381 | 7/2003 |

(Continued)

OTHER PUBLICATIONS

Agenbach et al., "Amino Acid Variation within the Fusion Protein of Respiratory Syncytial Virus Subtype A and B Strains during Annual Epidemics in South Africa", *Virus Genes*, 30(2):267-278, 2005.
De Baets et al., "Recombinant influenza virus carrying the respiratory syncytial virus (RSV) F85-93 CTL epitope reduces RSV replication in mice," *Journal of Virology*, 87(6):3314-3323, 2013.
Declaration Under 37 C.F.R. § 1.132 by Benjamin Petsch submitted in U.S. Appl. No. 15/048,561, filed May 13, 2019.

(Continued)

*Primary Examiner* — Benjamin P Blumel
(74) *Attorney, Agent, or Firm* — Parker Highlander PLLC

(57) ABSTRACT

The present invention relates to a vaccine, especially a combination vaccine providing at least a first and a second antigenic function, the combination vaccine comprising at least one RNA encoding at least one or more proteins or fragments, variants or derivatives of proteins awarding antigenic function, wherein the first antigenic function being a Fusion (F) protein or a fragment, variant or derivative of a Fusion (F) protein derived from the virus family Paramyxoviridae and the second antigenic function being an Hemagglutinin (HA) protein or a fragment, variant or derivative of an Hemagglutinin (HA) protein derived from the virus family Orthomyxoviridae. Furthermore, the present invention is directed to a kit or kit of parts comprising the components of said combination vaccine and to said combination vaccine for use in a method of prophylactic or therapeutic treatment of diseases, particularly in the prevention or treatment of infectious diseases like RSV and influenza.

24 Claims, 25 Drawing Sheets
Specification includes a Sequence Listing.

(56) References Cited

U.S. PATENT DOCUMENTS

| | | |
|---|---|---|
| 9,907,862 B2 | 3/2018 | Baumhof et al. |
| 9,974,845 B2 | 5/2018 | Fotin-Mleczek et al. |
| 10,010,592 B2 | 7/2018 | Thess et al. |
| 10,017,826 B2 | 7/2018 | von der Mülbe et al. |
| 10,047,375 B2 | 8/2018 | Thess |
| 10,080,809 B2 | 9/2018 | Thess |
| 10,111,967 B2 | 10/2018 | Fotin-Mleczek et al. |
| 10,111,968 B2 | 10/2018 | Thess et al. |
| 10,117,920 B2 | 11/2018 | Fotin-Mleczek et al. |
| 10,150,797 B2 | 12/2018 | Kramps et al. |
| 10,166,283 B2 | 1/2019 | Thess et al. |
| 10,172,935 B2 | 1/2019 | Kallen et al. |
| 10,188,748 B2 | 1/2019 | von der Mülbe et al. |
| 10,232,024 B2 | 3/2019 | Thess et al. |
| 10,293,058 B2 | 5/2019 | Fotin-Mleczek et al. |
| 10,293,060 B2 | 5/2019 | Baumhof |
| 10,307,472 B2 | 6/2019 | Fotin-Mleczek et al. |
| 10,369,216 B2 | 8/2019 | Fotin-Mleczek et al. |
| 10,434,154 B2 | 10/2019 | Probst et al. |
| 10,434,158 B2 | 10/2019 | Fotin-Mleczek et al. |
| 10,441,653 B2 | 10/2019 | Hoerr et al. |
| 10,501,768 B2 | 12/2019 | Eber et al. |
| 10,517,827 B2 | 12/2019 | Eber et al. |
| 10,568,958 B2 | 2/2020 | Baumhof et al. |
| 10,568,972 B2 | 2/2020 | von der Mülbe et al. |
| 10,588,959 B2 | 3/2020 | Kallen et al. |
| 10,596,252 B2 | 3/2020 | Kallen et al. |
| 10,610,605 B2 | 4/2020 | Thess et al. |
| 10,648,017 B2 | 5/2020 | Wochner |
| 10,653,768 B2 | 5/2020 | Mutzke et al. |
| 10,653,799 B2 | 5/2020 | Thess et al. |
| 10,682,406 B2 | 6/2020 | Thess et al. |
| 10,682,426 B2 | 6/2020 | Schnee et al. |
| 10,711,315 B2 | 7/2020 | von der Mülbe et al. |
| 10,729,654 B2 | 8/2020 | Eber et al. |
| 10,729,761 B2 | 8/2020 | Kallen et al. |
| 10,738,306 B2 | 8/2020 | Thess |
| 10,751,424 B2 | 8/2020 | Baumhof et al. |
| 10,760,070 B2 | 9/2020 | Funkner et al. |
| 10,780,054 B2 | 9/2020 | Ketterer et al. |
| 10,799,577 B2 | 10/2020 | Thess et al. |
| 10,799,602 B2 | 10/2020 | Baumhof |
| 10,837,039 B2 | 11/2020 | Wochner et al. |
| 10,869,935 B2 | 12/2020 | Fotin-Mleczek et al. |
| 10,898,584 B2 | 1/2021 | Schlake et al. |
| 10,898,589 B2 | 1/2021 | Thess et al. |
| 10,912,826 B2 | 2/2021 | Thess et al. |
| 10,918,740 B2 | 2/2021 | Fotin-Mleczek et al. |
| 10,988,754 B2 | 4/2021 | Fotin-Mleczek et al. |
| 11,034,729 B2 | 6/2021 | Kramps et al. |
| 11,078,247 B2 | 8/2021 | Fotin-Mleczek et al. |
| 11,110,156 B2 | 9/2021 | Thess et al. |
| 11,110,157 B2 | 9/2021 | Fotin-Mleczek et al. |
| 11,110,166 B2 | 9/2021 | Fotin-Mleczek et al. |
| 11,135,312 B2 | 10/2021 | von der Mülbe et al. |
| 11,141,474 B2 | 10/2021 | Rauch et al. |
| 11,141,476 B2 | 10/2021 | Rauch |
| 11,149,278 B2 | 10/2021 | Thess et al. |
| 11,179,337 B2 | 11/2021 | Eber et al. |
| 11,225,682 B2 | 1/2022 | Reichert et al. |
| 11,241,493 B2 | 2/2022 | Rauch et al. |
| 11,248,223 B2 | 2/2022 | Yazdan Panah et al. |
| 11,254,951 B2 | 2/2022 | Thess |
| 11,266,735 B2 | 3/2022 | Kallen et al. |
| 11,268,157 B2 | 3/2022 | von der Mülbe et al. |
| 11,274,293 B2 | 3/2022 | Funkner et al. |
| 11,279,923 B2 | 3/2022 | Funkner et al. |
| 11,286,492 B2 | 3/2022 | Thess et al. |
| 2005/0032730 A1 | 2/2005 | Von der Mulbe et al. |
| 2005/0059624 A1 | 3/2005 | Hoerr et al. |
| 2005/0250723 A1 | 11/2005 | Hoerr et al. |
| 2006/0188490 A1 | 8/2006 | Hoerr et al. |
| 2007/0280929 A1 | 12/2007 | Hoerr et al. |
| 2008/0025944 A1 | 1/2008 | Hoerr et al. |
| 2008/0171711 A1 | 7/2008 | Hoerr et al. |
| 2008/0267873 A1 | 10/2008 | Hoerr et al. |
| 2009/0324584 A1 | 12/2009 | Hoerr et al. |
| 2010/0047261 A1 | 2/2010 | Hoerr et al. |
| 2010/0048883 A1 | 2/2010 | Ketterer et al. |
| 2010/0189729 A1 | 7/2010 | Hoerr et al. |
| 2010/0203076 A1 | 8/2010 | Fotin-Mleczek et al. |
| 2010/0291156 A1 | 11/2010 | Barner et al. |
| 2010/0305196 A1 | 12/2010 | Probst et al. |
| 2011/0053829 A1 | 3/2011 | Baumhof et al. |
| 2011/0250225 A1 | 10/2011 | Fotin-Mleczek et al. |
| 2012/0021043 A1 | 1/2012 | Kramps et al. |
| 2012/0258046 A1 | 10/2012 | Mutzke |
| 2013/0129754 A1 | 5/2013 | Thess et al. |
| 2013/0142818 A1 | 6/2013 | Baumhof et al. |
| 2013/0195867 A1 | 8/2013 | Hoerr et al. |
| 2013/0202645 A1 | 8/2013 | Barner et al. |
| 2013/0251742 A1 | 9/2013 | Probst et al. |
| 2013/0259879 A1 | 10/2013 | Baumhof et al. |
| 2013/0280283 A1 | 10/2013 | Lorenz et al. |
| 2013/0295043 A1 | 11/2013 | Kallen et al. |
| 2013/0336998 A1 | 12/2013 | Kallen et al. |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0093413 A1 | 4/2015 | Thess et al. |
| 2015/0118183 A1 | 4/2015 | Baumhof |
| 2015/0118264 A1 | 4/2015 | Baumhof et al. |
| 2015/0165006 A1 | 6/2015 | Thess et al. |
| 2015/0184195 A1 | 7/2015 | Thess et al. |
| 2015/0218554 A1 | 8/2015 | Thess |
| 2015/0258214 A1 | 9/2015 | Baumhof et al. |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0206756 A1 | 7/2016 | Thess et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | von der Mülbe |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |
| 2017/0239372 A1 | 8/2017 | Baumhof et al. |
| 2017/0252430 A1 | 9/2017 | Fotin-Mleczek et al. |
| 2017/0326225 A1 | 11/2017 | Rauch et al. |
| 2018/0044687 A1 | 2/2018 | Thess et al. |
| 2018/0078629 A1 | 3/2018 | Lorenz et al. |
| 2018/0125952 A1 | 5/2018 | Fotin-Mleczek et al. |
| 2018/0126003 A1 | 5/2018 | Hoerr |
| 2018/0142275 A1 | 5/2018 | Roos et al. |
| 2018/0147146 A1 | 5/2018 | Eber et al. |
| 2018/0148727 A1 | 5/2018 | Grund et al. |
| 2018/0201967 A1 | 7/2018 | Eber et al. |
| 2018/0207295 A1 | 7/2018 | Fotin-Mleczek et al. |
| 2018/0208957 A1 | 7/2018 | Roos et al. |
| 2018/0214537 A1 | 8/2018 | Mutzke et al. |
| 2018/0237786 A1 | 8/2018 | Schlake et al. |
| 2018/0237817 A1 | 8/2018 | Roos et al. |
| 2018/0243219 A1 | 8/2018 | Ketterer et al. |
| 2018/0256694 A1 | 9/2018 | Barner et al. |
| 2018/0296663 A1 | 10/2018 | Hipp et al. |
| 2018/0298372 A1 | 10/2018 | Funkner et al. |
| 2018/0312545 A1 | 11/2018 | Baumhof et al. |
| 2018/0371392 A1 | 12/2018 | Mayer et al. |
| 2019/0008954 A1 | 1/2019 | Baumhof |
| 2019/0010485 A1 | 1/2019 | Yazdan Panah et al. |
| 2019/0017100 A1 | 1/2019 | Wochner et al. |
| 2019/0024096 A1 | 1/2019 | Schmid et al. |
| 2019/0040378 A1 | 2/2019 | Fotin-Mleczek et al. |
| 2019/0049414 A1 | 2/2019 | Wochner et al. |
| 2019/0083602 A1 | 3/2019 | Roos et al. |
| 2019/0100784 A1 | 4/2019 | Eber et al. |

(56) References Cited

U.S. PATENT DOCUMENTS

| | | |
|---|---|---|
| 2019/0125857 A1 | 5/2019 | Rauch et al. |
| 2019/0133950 A1 | 5/2019 | Eber et al. |
| 2019/0151438 A1 | 5/2019 | Kallen et al. |
| 2019/0160164 A1 | 5/2019 | Rauch et al. |
| 2019/0177714 A1 | 6/2019 | Kunze et al. |
| 2019/0185859 A1 | 6/2019 | Fotin-Mleczek et al. |
| 2019/0194760 A1 | 6/2019 | Koch et al. |
| 2019/0225971 A1 | 7/2019 | Williams |
| 2019/0241633 A1 | 8/2019 | Fotin-Mleczek et al. |
| 2019/0249219 A1 | 8/2019 | Reichert et al. |
| 2019/0255161 A1 | 8/2019 | Thess et al. |
| 2019/0336608 A1 | 11/2019 | Baumhof et al. |
| 2019/0336611 A1 | 11/2019 | Baumhof et al. |
| 2019/0343933 A1 | 11/2019 | Horscroft et al. |
| 2019/0343942 A1 | 11/2019 | Fotin-Mleczek et al. |
| 2019/0345504 A1 | 11/2019 | Grund et al. |
| 2019/0351044 A1 | 11/2019 | Jasny et al. |
| 2019/0351047 A1 | 11/2019 | Jasny et al. |
| 2019/0351048 A1 | 11/2019 | Rauch |
| 2019/0365879 A1 | 12/2019 | Probst et al. |
| 2019/0381155 A1 | 12/2019 | Fotin-Mleczek et al. |
| 2019/0381180 A1 | 12/2019 | Baumhof et al. |
| 2020/0016264 A1 | 1/2020 | Hoerr et al. |
| 2020/0023076 A1 | 1/2020 | Fotin-Mleczek et al. |
| 2020/0040370 A1 | 2/2020 | Eber et al. |
| 2020/0085852 A1 | 3/2020 | Fotin-Mleczek |
| 2020/0085942 A1 | 3/2020 | Kramps et al. |
| 2020/0085943 A1 | 3/2020 | Baumhof et al. |
| 2020/0085944 A1 | 3/2020 | Heidenreich et al. |
| 2020/0149026 A1 | 5/2020 | Horscroft et al. |
| 2020/0163878 A1 | 5/2020 | Baumhof et al. |
| 2020/0179526 A1 | 6/2020 | Baumhof et al. |
| 2020/0216878 A1 | 7/2020 | Wochner |
| 2020/0246451 A1 | 8/2020 | Mutzke et al. |
| 2020/0268908 A1 | 8/2020 | Schnee et al. |
| 2020/0276336 A1 | 9/2020 | Thess et al. |
| 2020/0316189 A1 | 10/2020 | Kallen et al. |
| 2020/0318097 A1 | 10/2020 | Funkner et al. |
| 2020/0332293 A1 | 10/2020 | Thess |
| 2020/0338215 A1 | 10/2020 | Baumhof et al. |
| 2020/0383919 A1 | 12/2020 | Eber et al. |
| 2020/0383922 A1 | 12/2020 | Ketterer et al. |
| 2020/0392572 A1 | 12/2020 | Yazdan Panah et al. |
| 2020/0399322 A1 | 12/2020 | Baumhof et al. |
| 2021/0023199 A1 | 1/2021 | Kallen et al. |
| 2021/0030683 A1 | 2/2021 | Eber et al. |
| 2021/0030864 A1 | 2/2021 | Petsch et al. |
| 2021/0030866 A1 | 2/2021 | Kallen et al. |
| 2021/0040526 A1 | 2/2021 | Wochner et al. |
| 2021/0046179 A1 | 2/2021 | Fotin-Mleczek et al. |
| 2021/0060175 A1 | 3/2021 | Fotin-Mleczek et al. |
| 2021/0060181 A1 | 3/2021 | Thess et al. |
| 2021/0069315 A1 | 3/2021 | Baumhof et al. |
| 2021/0128716 A1 | 5/2021 | Thess et al. |
| 2021/0162037 A1 | 6/2021 | Jasny et al. |
| 2021/0170017 A1 | 6/2021 | Lutz et al. |
| 2021/0180106 A1 | 6/2021 | Wochner et al. |
| 2021/0187124 A1 | 6/2021 | Schlake et al. |
| 2021/0198649 A1 | 7/2021 | Fotin-Mleczek et al. |
| 2021/0205434 A1 | 7/2021 | Petsch et al. |
| 2021/0251898 A1 | 8/2021 | English et al. |
| 2021/0260178 A1 | 8/2021 | Jasny et al. |
| 2021/0261627 A1 | 8/2021 | Kramps et al. |
| 2021/0261897 A1 | 8/2021 | Yazdan Panah et al. |
| 2021/0308238 A1 | 10/2021 | Hoerr et al. |
| 2021/0361761 A1 | 11/2021 | Lutz et al. |
| 2021/0361764 A1 | 11/2021 | Fotin-Mleczek et al. |
| 2021/0369827 A1 | 12/2021 | Fotin-Mleczek et al. |
| 2021/0393755 A1 | 12/2021 | Thess et al. |
| 2021/0401966 A1 | 12/2021 | Rauch et al. |
| 2021/0401971 A1 | 12/2021 | Rauch |
| 2021/0403925 A1 | 12/2021 | Chevessier-Tünnesen et al. |
| 2022/0025369 A1 | 1/2022 | Fotin-Mleczek et al. |
| 2022/0040281 A1 | 2/2022 | Schwendt et al. |
| 2022/0073962 A1 | 3/2022 | Schwenger et al. |
| 2022/0090092 A1 | 3/2022 | Thess et al. |
| 2022/0096616 A1 | 3/2022 | Barner et al. |
| 2022/0119795 A1 | 4/2022 | Yazdan Panah et al. |

FOREIGN PATENT DOCUMENTS

| | | | |
|---|---|---|---|
| WO | WO 2009/127230 | | 10/2009 |
| WO | WO/2010/037539 | * | 4/2010 |
| WO | WO 2010/088927 | | 8/2010 |
| WO | WO 2011/008974 | | 1/2011 |
| WO | WO 2011/069528 | | 6/2011 |
| WO | WO 2011/069586 | | 6/2011 |
| WO | WO 2011/069587 | | 6/2011 |
| WO | WO 2011/144358 | | 11/2011 |
| WO | WO 2012/013326 | | 2/2012 |
| WO | WO 2012/019780 | | 2/2012 |
| WO | WO 2012/089338 | | 7/2012 |
| WO | WO 2012/113513 | | 8/2012 |
| WO | WO 2012/116810 | | 9/2012 |
| WO | WO 2012/116811 | | 9/2012 |
| WO | WO 2013/113501 | | 8/2013 |
| WO | WO 2013/113502 | | 8/2013 |
| WO | WO 2013/113736 | | 8/2013 |
| WO | WO 2015/101414 | | 7/2015 |
| WO | WO 2015/101415 | | 7/2015 |
| WO | WO 2015/101416 | | 7/2015 |
| WO | WO 2015/135558 | | 9/2015 |
| WO | WO 2015/149944 | | 10/2015 |

OTHER PUBLICATIONS

Fleeton et al., "Self-replicative RNA vaccines elicit protection against influenza A virus, respiratory syncytial virus, and a tickborne encephalitis virus," *Journal of Infectious Diseases*, 183(9):1395-1398, 2001.

GenBank Accession AAX23994, fusion protein [human orthopneumovirus], 2005.

GenBank Accession HEMA_I34A1, RecName: Full=Hemagglutinin; Contain: RecName: Full=Hemagglutinin HA1 chain; Contains: RecName: Full=Hemagglutinin HA2 chain; Flags: Precursor, 2012.

Johnstone et al., "Shifting immunodominance pattern of two cytotoxic T lymphocyte epitopes in the F glycoprotein of the Long strain of respiratory syncytial virus", *J. Gen. Virol.*, 85(11):3229-3238, 2004.

Mani et al., "Codon optimization of the major antigen encoding genes of diverse strains of influenza A virus," Interdiscip. Sci. Comput. Life Sci., 3:36-42, 2011.

Mottram et al., "Type 1 and 2 immunity following vaccination is influenced by nanoparticle size: formulation of a model vaccine for respiratory syncytial virus," *Molecular Pharmaceutics*, 4(1):73-84, 2007.

Office Action issued in U.S. Appl. No. 15/048,561, mailed Aug. 29, 2016.

Office Action issued in U.S. Appl. No. 15/048,561, mailed Aug. 22, 2019.

Office Action issued in U.S. Appl. No. 15/048,561, mailed Feb. 8, 2018.

Office Action issued in U.S. Appl. No. 15/048,561, mailed Jan. 18, 2017.

Office Action issued in U.S. Appl. No. 15/048,561, mailed Jan. 11, 2019.

Office Action issued in U.S. Appl. No. 15/048,561, mailed Jun. 30, 2017.

Office Communication issued in corresponding EP Application No. 14761282, mailed on Feb. 28, 2019.

Office Communication issued in U.S. Appl. No. 16/781,781, mailed Oct. 28, 2020.

Office Communication issued in U.S. Appl. No. 16/781,781, mailed May 12, 2021.

Office Communication issued in U.S. Appl. No. 16/781,781, mailed Nov. 1, 2021.

PCT International Search Report and Written Opinion issued in International Application No. PCT/EP2014/002302, mailed Nov. 3, 2014.

(56) References Cited

OTHER PUBLICATIONS

Petsch et al., "Protective efficacy of in vitro synthesized, specific mRNA vaccines against influenza A virus infection," *Nature Biotechnology*, 30(12):1210-1216, 2012.
Schlake et al., "Developing mRNA-vaccine technologies," *RNA Biology*, 9(11):1319-1330, 2012.
Talaat et al., "A combination vaccine confers full protection against co-infections with influenza, herpes simplex and respiratory syncytial viruses," *Vaccine*, 20(3-4):538-544, 2001.
Turner et al., "A novel influenza virus hemagglutinin-respiratory syncytial virus (RSV) fusion protein subunit vaccine against influenza and RSV," *Journal of Virology*, 87(19):10792-10804, 2013.

\* cited by examiner

Anti-HA antibodies

FIG. 4

F protein of RSV Long (SEQ ID No. 1):

NCBI Accession No. AAX23994

MELPILKANAITTILAAVTFCFASSQNITEEFYQSTCSAVSKGYLSALRTGWYTSVITIELSNIKENKCN
GTDAKVKLINQELDKYKNAVTELQLLMQSTTAANNRARRELPRFMNYTLNNTKKTNVTLSKKRKRRFLGF
LLGVGSAIASGIAVSKVLHLEGEVNKIKSALLSTNKAVVSLSNGVSVLTSKVLDLKNYIDKQLLPIVNKQ
SCRISNIETVIEFQQKNNRLLEITREFSVNAGVTTPVSTYMLTNSELLSLINDMPITNDQKKLMSNNVQI
VRQQSYSIMSIIKEEVLAYVVQLPLYGVIDTPCWKLHTSPLCTTNTKEGSNICLTRTDRGWYCDNAGSVS
FFPQAETCKVQSNRVFCDTMNSLTLPSEVNLCNVDIFNPKYDCKIMTSKTDVSSSVITSLGAIVSCYGKT
KCTASNKNRGIIKTFSNGCDYVSNKGVDTVSVGNTLYYVNKQEGKSLYVKGEPIINFYDPLVFPSDEFDA
SISQVNEKINQSLAFIRKSDELLHHVNAGKSTTNIMITTIIVIIVILLSLIAVGLLLYCKARSTPVTLS
KDQLSGINNIAFSN

FIG. 5

F protein of RSV A2 (SEQ ID No. 2):

NCBI Accession No. AAB59858

MELLILKANAITTILTAVTFCFASGQNITEEFYQSTCSAVSKGYLSALRTGWYTSVITIELSNI
KENKCNGTDAKVKLIKQELDKYKNAVTELQLLMQSTPPTNNRARRELPRFMNYTLNNAKKTNVT
LSKKRKRRFLGFLLGVGSAIASGVAVSKVLHLEGEVNKIKSALLSTNKAVVSLSNGVSVLTSKV
LDLKNYIDKQLLPIVNKQSCSISNIETVIEFQQKNNRLLEITREFSVNAGVTTPVSTYMLTNSE
LLSLINDMPITNDQKKLMSNNVQIVRQQSYSIMSIIKEEVLAYVVQLPLYGVIDTPCWKLHTSP
LCTTNTKEGSNICLTRTDRGWYCDNAGSVSFFPQAETCKVQSNRVFCDTMNSLTLPSEINLCNV
DIFNPKYDCKIMTSKTDVSSSVITSLGAIVSCYGKTKCTASNKNRGIIKTFSNGCDYVSNKGMD
TVSVGNTLYYVNKQEGKSLYVKGEPIINFYDPLVFPSDEFDASISQVNEKINQSLAFIRKSDEL
LHNVAGKSTTNIMITTIIVIIVILLSLIAVGLLLYCKARSTPVTLSKDQLSGINNIAFSN

FIG. 6

HA protein of Influenza A/Puerto Rico/8/1934 (SEQ ID No. 3):

NCBI Accession No. ABO21709

MKANLLVLLCALAAADADTICIGYHANNSTDTVDTVLEKNVTVTHSVNLLEDSHNGKLCRLKGI
APLQLGKCNIAGWLLGNPECDPLLPVRSWSYIVETPNSENGICYPGDFIDYEELREQLSSVSSF
ERFEIFPKESSWPNHNTNGVTAACSHEGKSSFYRNLLWLTEKEGSYPKLKNSYVNKKGKEVLVL
WGIHHPPNSKEQQNLYQNENAYVSVVTSNYNRRFTPEIAERPKVRDQAGRMNYYWTLLKPGDTI
IFEANGNLIAPMYAFALSRGFGSGIITSNASMHECNTKCQTPLGAINSSLPYQNIHPVTIGECP
KYVRSAKLRMVTGLRNIPSIQSRGLFGAIAGFIEGGWTGMIDGWYGYHHQNEQGSGYAADQKST
QNAINGITNKVNTVIEKMNIQFTAVGKEFNKLEKRMENLNKKVDDGFLDIWTYNAELLVLLENE
RTLDFHDSNVKNLYEKVKSQLKNNAKEIGNGCFEFYHKCDNECMESVRNGTYDYPKYSEESKLN
REKVDGVKLESMGIYQILAIYSTVASSLVLLVSLGAISFWMCSNGSLQCRICI

FIG. 7

Wild type coding sequence of F protein of RSV Long (Human respiratory syncytial virus strain ATCC VR-26 (SEQ ID No. 4):

NCBI Accession No. AY911262 atggagttgccaatcctcaaagcaaatgcaattaccacaatcctcgctgcagtcacattttgctttgctt
ctagtcaaaacatcactgaagaattttatcaatcaacatgcagtgcagttagcaaaggctatcttagtgc
tctaagaactggttggtatactagtgttataactatagaattaagtaatatcaaggaaaataagtgtaat
ggaacagatgctaaggtaaaattgataaaccaagaattagataaatataaaaatgctgtaacagaattgc
agttgctcatgcaaagcacaacagcagcaaacaatcgagccagaagagaactaccaaggtttatgaatta
tacactcaacaataccaaaaaaaccaatgtaacattaagcaagaaaaggaaaagaagatttcttggtttt
ttgttaggtgttggatctgcaatcgccagtggcattgctgtatctaaggtcctgcacttagaaggagaag
tgaacaagatcaaaagtgctctactatccacaaacaaggccgtagtcagcttatcaaatggagttagtgt
cttaaccagcaaagtgttagacctcaaaaactatatagataaacaattgttacctattgtgaataagcaa
agctgcagaatatcaaatatagaaactgtgatagagttccaacaaaagaacaacagactactagagatta
ccagggaatttagtgttaatgcaggtgtaactacacctgtaagcacttacatgttaactaatagtgaatt
attgtcattaatcaatgatatgcctataacaaatgatcagaaaaagttaatgtccaacaatgttcaaata
gttagacagcaaagttactctatcatgtccataataaaagaggaagtcttagcatatgtagtacaattac
cactatatggtgtgatagataccttgttggaaattacacacatcccctctatgtacaaccaacacaaa
agaagggtcaaacatctgtttaacaagaactgacagaggatggtactgtgacaatgcaggatcagtatct
ttcttcccacaagctgaaacatgtaaagttcaatcgaatcgagtattttgtgacacaatgaacagtttaa
cattaccaagtgaagtaaatctctgcaatgttgacatattcaatcccaaatatgattgtaaaattatgac
ttcaaaaacagatgtaagcagctccgttatcacatctctaggagccattgtgtcatgctatggcaaaact
aaatgtacagcatccaataaaaatcgtggaatcataagacattttctaacgggtgtgattatgtatcaa
ataaaggggtggacactgtgtctgtaggtaacacattatattgtaaataagcaagaaggcaaaagtct
ctatgtaaaaggtgaaccaataataaatttctatgacccattagtattcccctctgatgaatttgatgca
tcaatatctcaagtcaatgagaagattaaccagagtttagcatttattcgtaaatccgatgaattattac
atcatgtaaatgctggtaaatcaaccacaaatatcatgataactactataattatagtgattatagtaat
attgttatcattaattgctgttggactgctcctatactgtaaggccagaagcacaccagtcacactaagc
aaggatcaactgagtggtataaataatattgcatttagtaactga

FIG. 8

Wild type coding sequence of F protein of RSV A2 (SEQ ID No. 5)

NCBI Accession No. M11486.1 atggagttgctaatcctcaaagcaaatgcaattaccacaatcctcactgcagtcacattttgtt
ttgcttctggtcaaaacatcactgaagaattttatcaatcaacatgcagtgcagttagcaaagg
ctatcttagtgctctgagaactggttggtataccagtgttataactatagaattaagtaatatc
aaggaaaataagtgtaatggaacagatgctaaggtaaaattgataaaacaagaattagataaat
ataaaaatgctgtaacagaattgcagttgctcatgcaaagcacaccaccaacaaacaatcgagc
cagaagagaactaccaaggtttatgaattatacactcaacaatgccaaaaaaccaatgtaaca
ttaagcaagaaaggaaaagaagatttcttggttttttgttaggtgttggatctgcaatcgcca
gtggcgttgctgtatctaaggtcctgcacctagaaggggaagtgaacaagatcaaaagtgctct
actatccacaaacaaggctgtagtcagcttatcaaatggagttagtgtcttaaccagcaaagtg
ttagacctcaaaaactatatagataaacaattgttacctattgtgaacaagcaaagctgcagca
tatcaaatatagaaactgtgatagagttccaacaaaagaacaacagactactagagattaccag
ggaatttagtgttaatgcaggtgtaactacacctgtaagcacttacatgttaactaatagtgaa
ttattgtcattaatcaatgatatgcctataacaaatgatcagaaaagttaatgtccaacaatg
ttcaaatagttagacagcaaagttactctatcatgtccataataaagaggaagtcttagcata
tgtagtacaattaccactatatggtgttatagatacaccctgttggaaactacacacatccct
ctatgtacaaccaacacaaaagaagggtccaacatctgtttaacaagaactgacagaggatggt
actgtgacaatgcaggatcagtatctcttcttcccacaagctgaaacatgtaaagttcaatcaaa
tcgagtattttgtgacacaatgaacagtttaacattaccaagtgaaataaatctctgcaatgtt
gacatattcaaccccaaatatgattgtaaaattatgacttcaaaaacagatgtaagcagctccg
ttatcacatctctaggagccattgtgtcatgctatggcaaaactaaatgtacagcatccaataa
aaatcgtggaatcataaagacattttctaacgggtgcgattatgtatcaaataaagggatggac
actgtgtctgtaggtaacacattatattatgtaaataagcaagaaggtaaaagtctctatgtaa
aaggtgaaccaataataaatttctatgacccattagtattccctctgatgaatttgatgcatc
aatatctcaagtcaacgagaagattaaccagagcctagcatttattcgtaaatccgatgaatta
ttacataatgtaaatgctggtaaatccaccacaaatatcatgataactactataattatagtga
ttatagtaatattgttatcattaattgctgttggactgctcttatactgtaaggccagaagcac
accagtcacactaagcaaagatcaactgagtggtataaataatattgcatttagtaactaa

FIG. 9

Wild type coding sequence of HA protein of Influenza A/Puerto Rico/8/1934 (SEQ ID No. 6)

NCBI Accession No. EF467821 atgaaggcaaacctactggtcctgttatgtgcacttgcagctgcagatgcagacacaatatgtataggct
accatgcgaacaattcaaccgacactgttgacacagtactcgagaagaatgtgacagtgacacactctgt
taacctgctcgaagacagccacaacggaaaactatgtagattaaaaggaatagccccactacaattgggg
aaatgtaacatcgccggatggctcttgggaaacccagaatgcgacccactgcttccagtgagatcatggt
cctacattgtagaaacaccaaactctgagaatggaatatgttatccaggagatttcatcgactatgagga
gctgagggagcaattgagctcagtgtcatcattcgaaagattcgaaatatttcccaaagaaagctcatgg
cccaaccacaacacaaacggagtaacggcagcatgctcccatgaggggaaaagcagtttttacagaaatt
tgctatggctgacggagaaggagggctcatacccaaagctgaaaaattcttatgtgaacaaaaagggaa
agaagtccttgtactgtggggtattcatcaccgcctaacagtaaggaacaacagaatctctatcagaat
gaaaatgcttatgtctctgtagtgacttcaaattataacaggagatttaccccggaaatagcagaaagac
ccaaagtaagagatcaagctgggaggatgaactattactggaccttgctaaaacccggagacacaataat
atttgaggcaaatggaaatctaatagcaccaatgtatgctttcgcactgagtagaggctttgggtccggc
atcatcacctcaaacgcatcaatgcatgagtgtaacacgaagtgtcaaacaccctgggagctataaaca
gcagtctcccttaccagaatatacacccagtcacaataggagagtgcccaaaatacgtcaggagtgccaa
attgaggatggttacaggactaaggaacaatccgtccattcaatccagaggtctatttggagccattgcc
ggttttattgaaggggatggactggaatgatagatggatggtatggttatcatcatcagaatgaacagg
gatcaggctatgcagcggatcaaaaaagcacacaaaatgccattaacgggattacaaacaaggtgaacac
tgttatcgagaaaatgaacattcaattcacagctgtgggtaaagaattcaacaaattagaaaaaggatg
gaaaatttaaataaaaagttgatgatggatttctggacatttggacatataatgcagaattgttagttc
tactggaaaatgaaaggactctggatttccatgactcaaatgtgaagaatctgtatgagaaagtaaaaag
ccaattaaagaataatgccaaagaaatcggaaatggatgttttgagttctaccacaagtgtgacaatgaa
tgcatggaaagtgtaagaaatgggacttatgattatcccaaatattcagaagagtcaaagttgaacaggg
aaaaggtagatggagtgaaattggaatcaatggggatctatcagattctggcgatctactcaactgtcgc
cagttcactggtgcttttggtctccctgggggcaatcagtttctggatgtgttctaatggatctttgcag
tgcagaatatgcatctga

FIG. 10

DNA RSV Long F, GC enriched (SEQ ID No. 7)

```
ATGGAGCTGCCCATCCTCAAGGCCAACGCCATCACCACCATCCTGGCGGCCGTGACGTTCTGCT
TCGCCAGCTCCCAGAACATCACCGAGGAGTTCTACCAGAGCACCTGCTCCGCCGTCAGCAAGGG
CTACCTGTCCGCCCTCCGGACCGGGTGGTACACGAGCGTGATCACCATCGAGCTGTCCAACATC
AAGGAGAACAAGTGCAACGGCACCGACGCGAAGGTGAAGCTGATCAACCAGGAGCTCGACAAGT
ACAAGAACGCCGTCACCGAGCTGCAGCTGCTCATGCAGAGCACGACCGCCGCCAACAACCGCGC
GCGGCGCGAGCTGCCGCGGTTCATGAACTACACCCTGAACAACACCAAGAAGACGAACGTGACC
CTCTCCAAGAAGCGCAAGCGGCGCTTCCTGGGGTTCCTGCTCGGCGTGGGGAGCGCCATCGCCT
CCGGCATCGCCGTCAGCAAGGTGCTGCACCTGGAGGGCGAGGTGAACAAGATCAAGTCCGCCCT
CCTGAGCACCAACAAGGCGGTCGTGTCCCTGAGCAACGGGGTGTCCGTCCTCACCAGCAAGGTG
CTGGACCTGAAGAACTACATCGACAAGCAGCTCCTGCCCATCGTGAACAAGCAGTCCTGCCGGA
TCAGCAACATCGAGACGGTCATCGAGTTCCAGCAGAAGAACAACCGCCTGCTCGAGATCACCCG
GGAGTTCAGCGTGAACGCCGGCGTGACCACCCCCGTCTCCACGTACATGCTGACCAACAGCGAG
CTGCTCTCCCTGATCAACGACATGCCCATCACCAACGACCAGAAGAAGCTGATGAGCAACAACG
TGCAGATCGTGCGCCAGCAGTCCTACAGCATCATGTCCATCATCAAGGAGGAGGTCCTCGCCTA
CGTGGTGCAGCTGCCGCTGTACGGGGTCATCGACACCCCTGCTGGAAGCTCCACACGAGCCCC
CTGTGCACCACCAACACCAAGGAGGGCTCCAACATCTGCCTGACGCGGACCGACCGCGGGTGGT
ACTGCGACAACGCCGGCAGCGTGTCCTTCTTCCCCCAGGCCGAGACCTGCAAGGTCCAGAGCAA
CCGGGTGTTCTGCGACACCATGAACTCCCTCACGCTGCCGAGCGAGGTGAACCTGTGCAACGTC
GACATCTTCAACCCCAAGTACGACTGCAAGATCATGACCTCCAAGACCGACGTGAGCTCCAGCG
TGATCACCTCCCTCGGCGCGATCGTCAGCTGCTACGGGAAGACGAAGTGCACCGCCAGCAACAA
GAACCGCGGCATCATCAAGACCTTCTCCAACGGGTGCGACTACGTGAGCAACAAGGGCGTGGAC
ACCGTCTCCGTGGGCAACACCCTGTACTACGTGAACAAGCAGGAGGGGAAGAGCCTGTACGTCA
AGGGCGAGCCCATCATCAACTTCTACGACCCCCTCGTGTTCCCGTCCGACGAGTTCGACGCCAG
CATCTCCCAGGTGAACGAGAAGATCAACCAGAGCCTGGCCTTCATCCGGAAGTCCGACGAGCTG
CTGCACCACGTCAACGCCGGGAAGAGCACGACCAACATCATGATCACCACCATCATCATCGTGA
TCATCGTGATCCTCCTGTCCCTGATCGCGGTCGGCCTCCTGCTGTACTGCAAGGCCCGCAGCAC
GCCCGTGACCCTCTCCAAGGACCAGCTGAGCGGGATCAACAACATCGCCTTCTCCAACTGA
```

FIG. 11

DNA RSV A2 F, GC enriched (SEQ ID No. 8)

```
ATGGAGCTGCTCATCCTGAAGGCCAACG

DNA RSV A2 F (P102A), GC enriched (SEQ ID No. 9)

ATGGAGCTGCTCATCCTGAAGGCCAACGCCATCACCACCATCCTGACGGCGGTGACCTTCTGCT
TCGCCAGCGGCCAGAACATCACCGAGGAGTTCTACCAGTCCACCTGCAGCGCCGTCTCCAAGGG
GTACCTCAGCGCCCTGCGGACGGGCTGGTACACCTCCGTGATCACCATCGAGCTGAGCAACATC
AAGGAGAACAAGTGCAACGGGACCGACGCCAAGGTGAAGCTCATCAAGCAGGAGCTGGACAAGT
ACAAGAACGCGGTCACGGAGCTGCAGCTCCTGATGCAGTCCACCCCGGCGACCAACAACCGCGC
CCGGCGCGAGCTGCCCCGGTTCATGAACTACACCCTCAACAACGCCAAGAAGACGAACGTGACC
CTGAGCAAGAAGCGCAAGCGGCGCTTCCTGGGCTTCCTCCTGGGGGTGGGCTCCGCCATCGCGA
GCGGCGTCGCCGTGTCCAAGGTGCTGCACCTCGAGGGGGAGGTCAACAAGATCAAGAGCGCCCT
GCTGTCCACCAACAAGGCCGTGGTGAGCCTCTCCAACGGCGTCAGCGTGCTGACCTCCAAGGTG
CTGGACCTCAAGAACTACATCGACAAGCAGCTGCTGCCCATCGTCAACAAGCAGAGCTGCTCCA
TCAGCAACATCGAGACGGTGATCGAGTTCCAGCAGAAGAACAACCGGCTCCTGGAGATCACCCG
CGAGTTCAGCGTGAACGCCGGGGTCACCACCCCCGTGTCCACGTACATGCTGACCAACAGCGAG
CTCCTGTCCCTGATCAACGACATGCCGATCACCAACGACCAGAAGAAGCTCATGAGCAACAACG
TGCAGATCGTCCGGCAGCAGTCCTACAGCATCATGTCCATCATCAAGGAGGAGGTGCTGGCGTA
CGTGGTCCAGCTGCCCCTCTACGGCGTGATCGACACCCCCTGCTGGAAGCTGCACACGAGCCCC
CTGTGCACCACCAACACCAAGGAGGGGTCCAACATCTGCCTCACGCGCACCGACCGGGGCTGGT
ACTGCGACAACGCCGGCAGCGTCTCCTTCTTCCCGCAGGCCGAGACCTGCAAGGTGCAGAGCAA
CCGCGTGTTCTGCGACACCATGAACTCCCTGACGCTGCCCAGCGAGATCAACCTCTGCAACGTC
GACATCTTCAACCCCAAGTACGACTGCAAGATCATGACCTCCAAGACCGACGTGAGCTCCAGCG
TGATCACCTCCCTGGGGGCCATCGTCAGCTGCTACGGCAAGACGAAGTGCACCGCCAGCAACAA
GAACCGGGGGATCATCAAGACCTTCTCCAACGGCTGCGACTACGTGAGCAACAAGGGCATGGAC
ACCGTGTCCGTCGGGAACACCCTGTACTACGTGAACAAGCAGGAGGGCAAGAGCCTCTACGTGA
AGGGGGAGCCCATCATCAACTTCTACGACCCGCTGGTCTTCCCCTCCGACGAGTTCGACGCGAG
CATCTCCCAGGTGAACGAGAAGATCAACCAGAGCCTGGCCTTCATCCGCAAGTCCGACGAGCTG
CTCCACAACGTGAACGCCGGCAAGAGCACGACCAACATCATGATCACCACCATCATCATCGTCA
TCATCGTGATCCTGCTGTCCCTCATCGCCGTGGGGCTGCTGCTCTACTGCAAGGCCCGGAGCAC
GCCCGTCACCCTGTCCAAGGACCAGCTGAGCGGCATCAACAACATCGCGTTCTCCAACTGA

FIG. 13

DNA RSV A2 F (I379V), GC enriched (SEQ ID No. 10)

ATGGAGCTGCTCATCCTGAAGGCCAACGCCATCACCACCATCCTGACGGCGGTGACCTTCTGCT
TCGCCAGCGGCCAGAACATCACCGAGGAGTTCTACCAGTCCACCTGCAGCGCCGTCTCCAAGGG
GTACCTCAGCGCCCTGCGGACGGGCTGGTACACCTCCGTGATCACCATCGAGCTGAGCAACATC
AAGGAGAACAAGTGCAACGGGACCGACGCCAAGGTGAAGCTCATCAAGCAGGAGCTGGACAAGT
ACAAGAACGCGGTCACGGAGCTGCAGCTCCTGATGCAGTCCACCCCGCCGACCAACAACCGCGC
CCGGCGCGAGCTGCCCCGGTTCATGAACTACACCCTCAACAACGCCAAGAAGACGAACGTGACC
CTGAGCAAGAAGCGCAAGCGGCGCTTCCTGGGCTTCCTCCTGGGGGTGGGCTCCGCCATCGCGA
GCGGCGTCGCCGTGTCCAAGGTGCTGCACCTCGAGGGGGAGGTCAACAAGATCAAGAGCGCCCT
GCTGTCCACCAACAAGGCCGTGGTGAGCCTCTCCAACGGCGTCAGCGTGCTGACCTCCAAGGTG
CTGGACCTCAAGAACTACATCGACAAGCAGCTGCTGCCCATCGTCAACAAGCAGAGCTGCTCCA
TCAGCAACATCGAGACGGTGATCGAGTTCCAGCAGAAGAACAACCGGCTCCTGGAGATCACCCG
CGAGTTCAGCGTGAACGCCGGGGTCACCACCCCCGTGTCCACGTACATGCTGACCAACAGCGAG
CTCCTGTCCCTGATCAACGACATGCCGATCACCAACGACCAGAAGAAGCTCATGAGCAACAACG
TGCAGATCGTCCGGCAGCAGTCCTACAGCATCATGTCCATCATCAAGGAGGAGGTGCTGGCGTA
CGTGGTCCAGCTGCCCCTCTACGGCGTGATCGACACCCCCTGCTGGAAGCTGCACACGAGCCCC
CTGTGCACCACCAACACCAAGGAGGGGTCCAACATCTGCCTCACGCGCACCGACCGGGGCTGGT
ACTGCGACAACGCCGGCAGCGTCTCCTTCTTCCCGCAGGCCGAGACCTGCAAGGTGCAGAGCAA
CCGCGTGTTCTGCGACACCATGAACTCCCTGACGCTGCCCAGCGAGGTCAACCTCTGCAACGTC
GACATCTTCAACCCCAAGTACGACTGCAAGATCATGACCTCCAAGACCGACGTGAGCTCCAGCG
TGATCACCTCCCTGGGGGCCATCGTCAGCTGCTACGGCAAGACGAAGTGCACCGCCAGCAACAA
GAACCGGGGGATCATCAAGACCTTCTCCAACGGCTGCGACTACGTGAGCAACAAGGGCATGGAC
ACCGTGTCCGTCGGGAACACCCTGTACTACGTGAACAAGCAGGAGGGCAAGAGCCTCTACGTGA
AGGGGGAGCCCATCATCAACTTCTACGACCCGCTGGTCTTCCCCTCCGACGAGTTCGACGCGAG
CATCTCCCAGGTGAACGAGAAGATCAACCAGAGCCTGGCCTTCATCCGCAAGTCCGACGAGCTG
CTCCACAACGTGAACGCCGGCAAGAGCACGACCAACATCATGATCACCACCATCATCATCGTCA
TCATCGTGATCCTGCTGTCCCTCATCGCCGTGGGCTGCTGCTCTACTGCAAGGCCCGGAGCAC
GCCCGTCACCCTGTCCAAGGACCAGCTGAGCGGCATCAACAACATCGCGTTCTCCAACTGA

FIG. 14

DNA RSV A2 F (M447V), GC enriched (SEQ ID No. 11)

```
ATGGAGCTGCTCATCCTGAAGGCCAACGCCATCACCACCATCCTGACGGCGGTGACCTTCTGCT
TCGCCAGCGGCCAGAACATCACCGAGGAGTTCTACCAGTCCACCTGCAGCGCCGTCTCCAAGGG
GTACCTCAGCGCCCTGCGGACGGGCTGGTACACCTCCGTGATCACCATCGAGCTGAGCAACATC
AAGGAGAACAAGTGCAACGGGACCGACGCCAAGGTGAAGCTCATCAAGCAGGAGCTGGACAAGT
ACAAGAACGCGGTCACGGAGCTGCAGCTCCTGATGCAGTCCACCCCGCCGACCAACAACCGCGC
CCGGCGCGAGCTGCCCCGGTTCATGAACTACACCCTCAACAACGCCAAGAAGACGAACGTGACC
CTGAGCAAGAAGCGCAAGCGGCGCTTCCTGGGCTTCCTCCTGGGGGTGGGCTCCGCCATCGCGA
GCGGCGTCGCCGTGTCCAAGGTGCTGCACCTCGAGGGGGAGGTCAACAAGATCAAGAGCGCCCT
GCTGTCCACCAACAAGGCCGTGGTGAGCCTCTCCAACGGCGTCAGCGTGCTGACCTCCAAGGTG
CTGGACCTCAAGAACTACATCGACAAGCAGCTGCTGCCCATCGTCAACAAGCAGAGCTGCTCCA
TCAGCAACATCGAGACGGTGATCGAGTTCCAGCAGAAGAACAACCGGCTCCTGGAGATCACCCG
CGAGTTCAGCGTGAACGCCGGGGTCACCACCCCCGTGTCCACGTACATGCTGACCAACAGCGAG
CTCCTGTCCCTGATCAACGACATGCCGATCACCAACGACCAGAAGAAGCTCATGAGCAACAACG
TGCAGATCGTCCGGCAGCAGTCCTACAGCATCATGTCCATCATCAAGGAGGAGGTGCTGGCGTA
CGTGGTCCAGCTGCCCCTCTACGGCGTGATCGACACCCCCTGCTGGAAGCTGCACACGAGCCCC
CTGTGCACCACCAACACCAAGGAGGGGTCCAACATCTGCCTCACGCGCACCGACCGGGGCTGGT
ACTGCGACAACGCCGGCAGCGTCTCCTTCTTCCCGCAGGCCGAGACCTGCAAGGTGCAGAGCAA
CCGCGTGTTCTGCGACACCATGAACTCCCTGACGCTGCCCAGCGAGATCAACCTCTGCAACGTC
GACATCTTCAACCCCAAGTACGACTGCAAGATCATGACCTCCAAGACCGACGTGAGCTCCAGCG
TGATCACCTCCCTGGGGGCCATCGTCAGCTGCTACGGCAAGACGAAGTGCACCGCCAGCAACAA
GAACCGGGGGATCATCAAGACCTTCTCCAACGGCTGCGACTACGTGAGCAACAAGGGCGTGGAC
ACCGTGTCCGTCGGGAACACCCTGTACTACGTGAACAAGCAGGAGGGCAAGAGCCTCTACGTGA
AGGGGGAGCCCATCATCAACTTCTACGACCCGCTGGTCTTCCCCTCCGACGAGTTCGACGCGAG
CATCTCCCAGGTGAACGAGAAGATCAACCAGAGCCTGGCCTTCATCCGCAAGTCCGACGAGCTG
CTCCACAACGTGAACGCCGGCAAGAGCACGACCAACATCATGATCACCACCATCATCATCGTCA
TCATCGTGATCCTGCTGTCCCTCATCGCCGTGGGCTGCTGCTCTACTGCAAGGCCCGGAGCAC
GCCCGTCACCCTGTCCAAGGACCAGCTGAGCGGCATCAACAACATCGCGTTCTCCAACTGA
```

FIG. 15

DNA Influenza PR8 HA, GC enriched (SEQ ID No. 12)

```
ATGAAGGCCAACCTGCTCGTGCTGCTGTGCGCCCTCGCGGCCGCCGACGCCGACACCATCTGCA
TCGGCTACCACGCCAACAACAGCACCGACACGGTCGACACCGTGCTGGAGAAGAACGTGACCGT
CACCCACTCCGTGAACCTGCTCGAGGACAGCCACAACGGGAAGCTGTGCCGGCTGAAGGGCATC
GCGCCCCTCCAGCTGGGGAAGTGCAACATCGCCGGCTGGCTGCTCGGGAACCCGGAGTGCGACC
CCTGCTGCCCGTGCGCTCCTGGAGCTACATCGTCGAGACGCCCAACTCCGAGAACGGCATCTG
CTACCCGGGCGACTTCATCGACTACGAGGAGCTCCGGGAGCAGCTGAGCTCCGTGAGCTCCTTC
GAGCGCTTCGAGATCTTCCCCAAGGAGAGCTCCTGGCCCAACCACAACACCAACGGGGTGACCG
CCGCCTGCAGCCACGAGGGCAAGTCCAGCTTCTACCGGAACCTGCTCTGGCTGACCGAGAAGGA
GGGGTCCTACCCCAAGCTGAAGAACAGCTACGTCAACAAGAAGGGCAAGGAGGTGCTCGTGCTG
TGGGGGATCCACCACCCGCCCAACTCCAAGGAGCAGCAGAACCTGTACCAGAACGAGAACGCGT
ACGTCAGCGTGGTGACGTCCAACTACAACGCCGGTTCACCCCCGAGATCGCCGAGCGCCCCAA
GGTCCGGGACCAGGCCGGCCGCATGAACTACTACTGGACCCTCCTGAAGCCGGGCGACACCATC
ATCTTCGAGGCCAACGGGAACCTGATCGCCCCGATGTACGCGTTCGCCCTCAGCCGGGGCTTCG
GGAGCGGCATCATCACGTCCAACGCCAGCATGCACGAGTGCAACACCAAGTGCCAGACCCCCCT
GGGCGCCATCAACTCCAGCCTGCCCTACCAGAACATCCACCCGGTGACCATCGGGGAGTGCCCC
AAGTACGTGCGCTCCGCCAAGCTCCGGATGGTCACGGGCCTGCGCAACAACCCCAGCATCCAGT
CCCGGGGGCTGTTCGGCGCGATCGCCGGGTTCATCGAGGGCGGCTGGACCGGGATGATCGACGG
CTGGTACGGGTACCACCACCAGAACGAGCAGGGCAGCGGGTACGCCGCCGACCAGAAGTCCACC
CAGAACGCCATCAACGGCATCACCAACAAGGTGAACACGGTGATCGAGAAGATGAACATCCAGT
TCACCGCGGTCGGCAAGGAGTTCAACAAGCTCGAGAAGCGCATGGAGAACCTGAACAAGAAGGT
GGACGACGGGTTCCTGGACATCTGGACCTACAACGCCGAGCTCCTGGTGCTGCTCGAGAACGAG
CGGACCCTGGACTTCCACGACAGCAACGTCAAGAACCTGTACGAGAAGGTGAAGTCCCAGCTCA
AGAACAACGCCAAGGAGATCGGCAACGGGTGCTTCGAGTTCTACCACAAGTGCGACAACGAGTG
CATGGAGAGCGTCCGCAACGGCACGTACGACTACCCCAAGTACTCCGAGGAGAGCAAGCTGAAC
CGGGAGAAGGTGGACGGGGTGAAGCTGGAGTCCATGGGCATCTACCAGATCCTCGCCATCTACA
GCACCGTCGCCTCCAGCCTGGTGCTGCTGGTGTCCCTCGGCGCGATCAGCTTCTGGATGTGCAG
CAACGGGTCCCTGCAGTGCCGCATCTGCATCTGA
```

FIG. 16

RNA RSV Long F, GC enriched (SEQ ID No. 13)

```
AUGGAGCUGCCCAUCCUCAAGGCCAACGCCAUCACCACCAUCCUGGCGGCCGUGACGUUCUGCU
UCGCCAGCUCCCAGAACAUCACCGAGGAGUUCUACCAGAGCACCUGCUCCGCCGUCAGCAAGGG
CUACCUGUCCGCCCUCCGGACCGGGUGGUACACGAGCGUGAUCACCAUCGAGCUGUCCAACAUC
AAGGAGAACAAGUGCAACGGCACCGACGCGAAGGUGAAGCUGAUCAACCAGGAGCUCGACAAGU
ACAAGAACGCCGUCACCGAGCUGCAGCUGCUCAUGCAGAGCACGACCGCCGCCAACAACCGCGC
GCGGCGCGAGCUGCCGCGGUUCAUGAACUACACCCUGAACAACACCAAGAAGACGAACGUGACC
CUCUCCAAGAAGCGCAAGCGGCGCUUCCUGGGGUUCCUGCUCGGCGUGGGGAGCGCCAUCGCCU
CCGGCAUCGCCGUCAGCAAGGUGCUGCACCUGGAGGGCGAGGUGAACAAGAUCAAGUCCGCCCU
CCUGAGCACCAACAAGGCGGUCGUGUCCCUGAGCAACGGGGUGUCCGUCCUCACCAGCAAGGUG
CUGGACCUGAAGAACUACAUCGACAAGCAGCUCCUGCCCAUCGUGAACAAGCAGUCCUGCCGGA
UCAGCAACAUCGAGACGGUCAUCGAGUUCCAGCAGAAGAACAACCGCCUGCUCGAGAUCACCCG
GGAGUUCAGCGUGAACGCCGGCGUGACCACCCCCGUCUCCACGUACAUGCUGACCAACAGCGAG
CUGCUCUCCCUGAUCAACGACAUGCCCAUCACCAACGACCAGAAGAAGCUGAUGAGCAACAACG
UGCAGAUCGUGCGCCAGCAGUCCUACAGCAUCAUGUCCAUCAUCAAGGAGGAGGUCCUCGCCUA
CGUGGUGCAGCUGCCGCUGUACGGGGUCAUCGACACCCCCUGCUGGAAGCUCCACACGAGCCCC
CUGUGCACCACCAACACCAAGGAGGGCUCCAACAUCUGCCUGACGCGGACCGACCGCGGGUGGU
ACUGCGACAACGCCGGCAGCGUGUCCUUCUUCCCCAGGCCGAGACCUGCAAGGUCCAGAGCAA
CCGGGUGUUCUGCGACACCAUGAACUCCCUCACGCUGCCGAGCGAGGUGAACCUGUGCAACGUC
GACAUCUUCAACCCCAAGUACGACUGCAAGAUCAUGACCUCCAAGACCGACGUGAGCUCCAGCG
UGAUCACCUCCCUCGGCGCGAUCGUCAGCUGCUACGGGAAGACGAAGUGCACCGCCAGCAACAA
GAACCGCGGCAUCAUCAAGACCUUCUCCAACGGGUGCGACUACGUGAGCAACAAGGGCGUGGAC
ACCGUCUCCGUGGGCAACACCCUGUACUACGUGAACAAGCAGGAGGGGAAGAGCCUGUACGUCA
AGGGCGAGCCCAUCAUCAACUUCUACGACCCCCUCGUGUUCCCGUCCGACGAGUUCGACGCCAG
CAUCUCCCAGGUGAACGAGAAGAUCAACCAGAGCCUGGCCUUCAUCCGGAAGUCCGACGAGCUG
CUGCACCACGUCAACGCCGGGAAGAGCACGACCAACAUCAUGAUCACCACCAUCAUCAUCGUGA
UCAUCGUGAUCCUCCUGUCCCUGAUCGCGGUCGGCCUCCUGCUGUACUGCAAGGCCCGCAGCAC
GCCCGUGACCCUCUCCAAGGACCAGCUGAGCGGGAUCAACAACAUCGCCUUCUCCAACUGA
```

FIG. 17

RNA RSV A2 F, GC enriched (SEQ ID No. 14)

```
AUGGAGCUGCUCAUCCUGAAGGCCAACGCCAUCACCACCAUCCUGACGGCGGUGACCUUCUGCU
UCGCCAGCGGCCAGAACAUCACCGAGGAGUUCUACCAGUCCACCUGCAGCGCCGUCUCCAAGGG
GUACCUCAGCGCCCUGCGGACGGGCUGGUACACCUCCGUGAUCACCAUCGAGCUGAGCAACAUC
AAGGAGAACAAGUGCAACGGGACCGACGCCAAGGUGAAGCUCAUCAAGCAGGAGCUGGACAAGU
ACAAGAACGCGGUCACGGAGCUGCAGCUCCUGAUGCAGUCCACCCCGCCGACCAACAACCGCGC
CCGGCGCGAGCUGCCCCGGUUCAUGAACUACACCCUCAACAACGCCAAGAAGACGAACGUGACC
CUGAGCAAGAAGCGCAAGCGGCGCUUCCUGGGCUUCCUCCUGGGGGUGGGCUCCGCCAUCGCGA
GCGGCGUCGCCGUGUCCAAGGUGCUGCACCUCGAGGGGGAGGUCAACAAGAUCAAGAGCGCCCU
GCUGUCCACCAACAAGGCCGUGGUGAGCCUCUCCAACGGCGUCAGCGUGCUGACCUCCAAGGUG
CUGGACCUCAAGAACUACAUCGACAAGCAGCUGCUGCCCAUCGUCAACAAGCAGAGCUGCUCCA
UCAGCAACAUCGAGACGGUGAUCGAGUUCCAGCAGAAGAACAACCGGCUCCUGGAGAUCACCCG
CGAGUUCAGCGUGAACGCCGGGGUCACCACCCCCGUGUCCACGUACAUGCUGACCAACAGCGAG
CUCCUGUCCCUGAUCAACGACAUGCCGAUCACCAACGACCAGAAGAAGCUCAUGAGCAACAACG
UGCAGAUCGUCCGGCAGCAGUCCUACAGCAUCAUGUCCAUCAUCAAGGAGGAGGUGCUGGCGUA
CGUGGUCCAGCUGCCCCUCUACGGCGUGAUCGACACCCCCUGCUGGAAGCUGCACACGAGCCCC
CUGUGCACCACCAACACCAAGGAGGGGUCCAACAUCUGCCUCACGCGCACCGACCGGGGCUGGU
ACUGCGACAACGCCGGCAGCGUCUCCUUCUUCCCGCAGGCCGAGACCUGCAAGGUGCAGAGCAA
CCGCGUGUUCUGCGACACCAUGAACUCCCUGACGCUGCCCAGCGAGAUCAACCUCUGCAACGUC
GACAUCUUCAACCCCAAGUACGACUGCAAGAUCAUGACCUCCAAGACCGACGUGAGCUCCAGCG
UGAUCACCUCCCUGGGGGCCAUCGUCAGCUGCUACGGCAAGACGAAGUGCACCGCCAGCAACAA
GAACCGGGGGAUCAUCAAGACCUUCUCCAACGGCUGCGACUACGUGAGCAACAAGGGCAUGGAC
ACCGUGUCCGUCGGGAACACCCUGUACUACGUGAACAAGCAGGAGGGCAAGAGCCUCUACGUGA
AGGGGGAGCCCAUCAUCAACUUCUACGACCCGCUGGUCUUCCCCUCCGACGAGUUCGACGCGAG
CAUCUCCCAGGUGAACGAGAAGAUCAACCAGAGCCUGGCCUUCAUCCGCAAGUCCGACGAGCUG
CUCCACAACGUGAACGCCGGCAAGAGCACGACCAACAUCAUGAUCACCACCAUCAUCAUCGUCA
UCAUCGUGAUCCUGCUGUCCCUCAUCGCCGUGGGCUGCUGCUCUACUGCAAGGCCCGGAGCAC
GCCCGUCACCCUGUCCAAGGACCAGCUGAGCGGCAUCAACAACAUCGCGUUCUCCAACUGA
```

FIG. 18

RNA RSV A2 F (P102A), GC enriched (SEQ ID No. 15)

```
AUGGAGCUGCUCAUCCUGAAGGCCAACGCCAUCACCACCAUCCUGACGGCGGUGACCUUCUGCU
UCGCCAGCGGCCAGAACAUCACCGAGGAGUUCUACCAGUCCACCUGCAGCGCCGUCUCCAAGGG
GUACCUCAGCGCCCUGCGGACGGGCUGGUACACCUCCGUGAUCACCAUCGAGCUGAGCAACAUC
AAGGAGAACAAGUGCAACGGGACCGACGCCAAGGUGAAGCUCAUCAAGCAGGAGCUGGACAAGU
ACAAGAACGCGGUCACGGAGCUGCAGCUCCUGAUGCAGUCCACCCCGGCGACCAACAACCGCGC
CCGGCGCGAGCUGCCCCGGUUCAUGAACUACACCCUCAACAACGCCAAGAAGACGAACGUGACC
CUGAGCAAGAAGCGCAAGCGGCGCUUCCUGGGCUUCCUCCUGGGGGUGGGCUCCGCCAUCGCGA
GCGGCGUCGCCGUGUCCAAGGUGCUGCACCUCGAGGGGGAGGUCAACAAGAUCAAGAGCGCCCU
GCUGUCCACCAACAAGGCCGUGGUGAGCCUCUCCAACGGCGUCAGCGUGCUGACCUCCAAGGUG
CUGGACCUCAAGAACUACAUCGACAAGCAGCUGCUGCCCAUCGUCAACAAGCAGAGCUGCUCCA
UCAGCAACAUCGAGACGGUGAUCGAGUUCCAGCAGAAGAACAACCGGCUCCUGGAGAUCACCCG
CGAGUUCAGCGUGAACGCCGGGGUCACCACCCCCGUGUCCACGUACAUGCUGACCAACAGCGAG
CUCCUGUCCCUGAUCAACGACAUGCCGAUCACCAACGACCAGAAGAAGCUCAUGAGCAACAACG
UGCAGAUCGUCCGGCAGCAGUCCUACAGCAUCAUGUCCAUCAUCAAGGAGGAGGUGCUGGCGUA
CGUGGUCCAGCUGCCCCUCUACGGCGUGAUCGACACCCCCUGCUGGAAGCUGCACACGAGCCCC
CUGUGCACCACCAACACCAAGGAGGGGUCCAACAUCUGCCUCACGCGCACCGACCGGGGCUGGU
ACUGCGACAACGCCGGCAGCGUCUCCUUCUUCCCGCAGGCCGAGACCUGCAAGGUGCAGAGCAA
CCGCGUGUUCUGCGACACCAUGAACUCCCUGACGCUGCCCAGCGAGAUCAACCUCUGCAACGUC
GACAUCUUCAACCCCAAGUACGACUGCAAGAUCAUGACCUCCAAGACCGACGUGAGCUCCAGCG
UGAUCACCUCCCUGGGGGCCAUCGUCAGCUGCUACGGCAAGACGAAGUGCACCGCCAGCAACAA
GAACCGGGGGAUCAUCAAGACCUUCUCCAACGGCUGCGACUACGUGAGCAACAAGGGCAUGGAC
ACCGUGUCCGUCGGGAACACCCUGUACUACGUGAACAAGCAGGAGGGCAAGAGCCUCUACGUGA
AGGGGGAGCCCAUCAUCAACUUCUACGACCCGCUGGUCUUCCCCUCCGACGAGUUCGACGCGAG
CAUCUCCCAGGUGAACGAGAAGAUCAACCAGAGCCUGGCCUUCAUCCGCAAGUCCGACGAGCUG
CUCCACAACGUGAACGCCGGCAAGAGCACGACCAACAUCAUGAUCACCACCAUCAUCAUCGUCA
UCAUCGUGAUCCUGCUGUCCCUCAUCGCCGUGGGGCUGCUGCUCUACUGCAAGGCCCGGAGCAC
GCCCGUCACCCUGUCCAAGGACCAGCUGAGCGGCAUCAACAACAUCGCGUUCUCCAACUGA
```

FIG. 19

RNA RSV A2 F (I379V), GC enriched (SEQ ID No. 16)

AUGGAGCUGCUCAUCCUGAAGGCCAACGCCAUCACCACCAUCCUGACGGCGGUGACCUUCUGCU
UCGCCAGCGGCCAGAACAUCACCGAGGAGUUCUACCAGUCCACCUGCAGCGCCGUCUCCAAGGG
GUACCUCAGCGCCCUGCGGACGGGCUGGUACACCUCCGUGAUCACCAUCGAGCUGAGCAACAUC
AAGGAGAACAAGUGCAACGGGACCGACGCCAAGGUGAAGCUCAUCAAGCAGGAGCUGGACAAGU
ACAAGAACGCGGUCACGGAGCUGCAGCUCCUGAUGCAGUCCACCCCGCCGACCAACAACCGCGC
CCGGCGCGAGCUGCCCCGGUUCAUGAACUACACCCUCAACAACGCCAAGAAGACGAACGUGACC
CUGAGCAAGAAGCGCAAGCGGCGCUUCCUGGGCUUCCUCCUGGGGGUGGGCUCCGCCAUCGCGA
GCGGCGUCGCCGUGUCCAAGGUGCUGCACCUCGAGGGGGAGGUCAACAAGAUCAAGAGCGCCCU
GCUGUCCACCAACAAGGCCGUGGUGAGCCUCUCCAACGGCGUCAGCGUGCUGACCUCCAAGGUG
CUGGACCUCAAGAACUACAUCGACAAGCAGCUGCUGCCCAUCGUCAACAAGCAGAGCUGCUCCA
UCAGCAACAUCGAGACGGUGAUCGAGUUCCAGCAGAAGAACAACCGGCUCCUGGAGAUCACCCG
CGAGUUCAGCGUGAACGCCGGGGUCACCACCCCCGUGUCCACGUACAUGCUGACCAACAGCGAG
CUCCUGUCCCUGAUCAACGACAUGCCGAUCACCAACGACCAGAAGAAGCUCAUGAGCAACAACG
UGCAGAUCGUCCGGCAGCAGUCCUACAGCAUCAUGUCCAUCAUCAAGGAGGAGGUGCUGGCGUA
CGUGGUCCAGCUGCCCCUCUACGGCGUGAUCGACACCCCCUGCUGGAAGCUGCACACGAGCCCC
CUGUGCACCACCAACACCAAGGAGGGGUCCAACAUCUGCCUCACGCGCACCGACCGGGGCUGGU
ACUGCGACAACGCCGGCAGCGUCUCCUUCUUCCCGCAGGCCGAGACCUGCAAGGUGCAGAGCAA
CCGCGUGUUCUGCGACACCAUGAACUCCCUGACGCUGCCCAGCGAGGUCAACCUCUGCAACGUC
GACAUCUUCAACCCCAAGUACGACUGCAAGAUCAUGACCUCCAAGACCGACGUGAGCUCCAGCG
UGAUCACCUCCCUGGGGGCCAUCGUCAGCUGCUACGGCAAGACGAAGUGCACCGCCAGCAACAA
GAACCGGGGGAUCAUCAAGACCUUCUCCAACGGCUGCGACUACGUGAGCAACAAGGGCAUGGAC
ACCGUGUCCGUCGGGAACACCCUGUACUACGUGAACAAGCAGGAGGGCAAGAGCCUCUACGUGA
AGGGGGAGCCCAUCAUCAACUUCUACGACCCGCUGGUCUUCCCCUCCGACGAGUUCGACGCGAG
CAUCUCCCAGGUGAACGAGAAGAUCAACCAGAGCCUGGCCUUCAUCCGCAAGUCCGACGAGCUG
CUCCACAACGUGAACGCCGGCAAGAGCACGACCAACAUCAUGAUCACCACCAUCAUCAUCGUCA
UCAUCGUGAUCCUGCUGUCCCUCAUCGCCGUGGGGCUGCUGCUCUACUGCAAGGCCCGGAGCAC
GCCCGUCACCCUGUCCAAGGACCAGCUGAGCGGCAUCAACAACAUCGCGUUCUCCAACUGA

FIG. 20

RNA RSV A2 F (M447V), GC enriched (SEQ ID No. 17)

AUGGAGCUGCUCAUCCUGAAGGCCAACGCCAUCACCACCAUCCUGACGGCGGUGACCUUCUGCU
UCGCCAGCGGCCAGAACAUCACCGAGGAGUUCUACCAGUCCACCUGCAGCGCCGUCUCCAAGGG
GUACCUCAGCGCCCUGCGGACGGGCUGGUACACCUCCGUGAUCACCAUCGAGCUGAGCAACAUC
AAGGAGAACAAGUGCAACGGGACCGACGCCAAGGUGAAGCUCAUCAAGCAGGAGCUGGACAAGU
ACAAGAACGCGGUCACGGAGCUGCAGCUCCUGAUGCAGUCCACCCCGCCGACCAACAACCGCGC
CCGGCGCGAGCUGCCCCGGUUCAUGAACUACACCCUCAACAACGCCAAGAAGACGAACGUGACC
CUGAGCAAGAAGCGCAAGCGGCGCUUCCUGGGCUUCCUCCUGGGGGUGGGCUCCGCCAUCGCGA
GCGGCGUCGCCGUGUCCAAGGUGCUGCACCUCGAGGGGGAGGUCAACAAGAUCAAGAGCGCCCU
GCUGUCCACCAACAAGGCCGUGGUGAGCCUCUCCAACGGCGUCAGCGUGCUGACCUCCAAGGUG
CUGGACCUCAAGAACUACAUCGACAAGCAGCUGCUGCCCAUCGUCAACAAGCAGAGCUGCUCCA
UCAGCAACAUCGAGACGGUGAUCGAGUUCCAGCAGAAGAACAACCGGCUCCUGGAGAUCACCCG
CGAGUUCAGCGUGAACGCCGGGGUCACCACCCCCGUGUCCACGUACAUGCUGACCAACAGCGAG
CUCCUGUCCCUGAUCAACGACAUGCCGAUCACCAACGACCAGAAGAAGCUCAUGAGCAACAACG
UGCAGAUCGUCCGGCAGCAGUCCUACAGCAUCAUGUCCAUCAUCAAGGAGGAGGUGCUGGCGUA
CGUGGUCCAGCUGCCCCUCUACGGCGUGAUCGACACCCCCUGCUGGAAGCUGCACACGAGCCCC
CUGUGCACCACCAACACCAAGGAGGGGUCCAACAUCUGCCUCACGCGCACCGACCGGGGCUGGU
ACUGCGACAACGCCGGCAGCGUCUCCUUCUUCCCGCAGGCCGAGACCUGCAAGGUGCAGAGCAA
CCGCGUGUUCUGCGACACCAUGAACUCCCUGACGCUGCCCAGCGAGAUCAACCUCUGCAACGUC
GACAUCUUCAACCCCAAGUACGACUGCAAGAUCAUGACCUCCAAGACCGACGUGAGCUCCAGCG
UGAUCACCUCCCUGGGGGCCAUCGUCAGCUGCUACGGCAAGACGAAGUGCACCGCCAGCAACAA
GAACCGGGGGAUCAUCAAGACCUUCUCCAACGGCUGCGACUACGUGAGCAACAAGGGCGUGGAC
ACCGUGUCCGUCGGGAACACCCUGUACUACGUGAACAAGCAGGAGGGCAAGAGCCUCUACGUGA
AGGGGGAGCCCAUCAUCAACUUCUACGACCCGCUGGUCUUCCCCUCCGACGAGUUCGACGCGAG
CAUCUCCCAGGUGAACGAGAAGAUCAACCAGAGCCUGGCCUUCAUCCGCAAGUCCGACGAGCUG
CUCCACAACGUGAACGCCGGCAAGAGCACGACCAACAUCAUGAUCACCACCAUCAUCAUCGUCA
UCAUCGUGAUCCUGCUGUCCCUCAUCGCCGUGGGGCUGCUGCUCUACUGCAAGGCCCGGAGCAC
GCCCGUCACCCUGUCCAAGGACCAGCUGAGCGGCAUCAACAACAUCGCGUUCUCCAACUGA

FIG. 21

RNA Influenza PR8 HA, GC enriched (SEQ ID No. 18)

AUGAAGGCCAACCUGCUCGUGCUGCUGUGCGCCCUCGCGGCCGCCGACGCCGACACCAUCUGCA
UCGGCUACCACGCCAACAACAGCACCGACACGGUCGACACCGUGCUGGAGAAGAACGUGACCGU
CACCCACUCCGUGAACCUGCUCGAGGACAGCCACAACGGGAAGCUGUGCCGGCUGAAGGGCAUC
GCGCCCUCCAGCUGGGGAAGUGCAACAUCGCCGGCUGGCUGCUCGGGAACCCGGAGUGCGACC
CCCUGCUGCCCGUGCGCUCCUGGAGCUACAUCGUCGAGACGCCCAACUCCGAGAACGGCAUCUG
CUACCCGGGCGACUUCAUCGACUACGAGGAGCUCCGGGAGCAGCUGAGCUCCGUGAGCUCCUUC
GAGCGCUUCGAGAUCUUCCCCAAGGAGAGCUCCUGGCCCAACCACAACACCAACGGGGUGACCG
CCGCCUGCAGCCACGAGGGCAAGUCCAGCUUCUACCGGAACCUGCUCUGGCUGACCGAGAAGGA
GGGGUCCUACCCCAAGCUGAAGAACAGCUACGUCAACAAGAAGGGCAAGGAGGUGCUCGUGCUG
UGGGGGAUCCACCACCCGCCCAACUCCAAGGAGCAGCAGAACCUGUACCAGAACGAGAACGCGU
ACGUCAGCGUGGUGACGUCCAACUACAACCGCCGGUUCACCCCCGAGAUCGCCGAGCGCCCCAA
GGUCCGGGACCAGGCCGGCCGCAUGAACUACUACUGGACCCUCCUGAAGCCGGGCGACACCAUC
AUCUUCGAGGCCAACGGGAACCUGAUCGCCCCGAUGUACGCGUUCGCCCUCAGCCGGGGCUUCG
GGAGCGGCAUCAUCACGUCCAACGCCAGCAUGCACGAGUGCAACACCAAGUGCCAGACCCCCCU
GGGCGCCAUCAACUCCAGCCUGCCCUACCAGAACAUCCACCCGGUGACCAUCGGGGAGUGCCCC
AAGUACGUGCGCUCCGCCAAGCUCCGGAUGGUCACGGGCCUGCGCAACAACCCCAGCAUCCAGU
CCCGGGGGCUGUUCGGCGCGAUCGCCGGGUUCAUCGAGGGCGGCUGGACCGGGAUGAUCGACGG
CUGGUACGGGUACCACCACCAGAACGAGCAGGGCAGCGGGUACGCCGCCGACCAGAAGUCCACC
CAGAACGCCAUCAACGGCAUCACCAACAAGGUGAACACGGUGAUCGAGAAGAUGAACAUCCAGU
UCACCGCGGUCGGCAAGGAGUUCAACAAGCUCGAGAAGCGCAUGGAGAACCUGAACAAGAAGGU
GGACGACGGGUUCCUGGACAUCUGGACCUACAACGCCGAGCUCCUGGUGCUGCUCGAGAACGAG
CGGACCCUGGACUUCCACGACAGCAACGUCAAGAACCUGUACGAGAAGGUGAAGUCCCAGCUCA
AGAACAACGCCAAGGAGAUCGGCAACGGGUGCUUCGAGUUCUACCACAAGUGCGACAACGAGUG
CAUGGAGAGCGUCCGCAACGGCACGUACGACUACCCCAAGUACUCCGAGGAGAGCAAGCUGAAC
CGGGAGAAGGUGGACGGGGUGAAGCUGGAGUCCAUGGGCAUCUACCAGAUCCUCGCCAUCUACA
GCACCGUCGCCUCCAGCCUGGUGCUGCUGGUGUCCCUCGGCGCGAUCAGCUUCUGGAUGUGCAG
CAACGGGUCCCUGCAGUGCCGCAUCUGCAUCUGA

FIG. 22

GC-enriched mRNA coding for F protein of RSV Long (SEQ ID No. 19):

```
GGGAGAAAGCUUACCAUGGAGCUGCCCAUCCUCAAGGCCAACGCCAUCACCACCAUCCUGGCGG
CCGUGACGUUCUGCUUCGCCAGCUCCCAGAACAUCACCGAGGAGUUCUACCAGAGCACCUGCUC
CGCCGUCAGCAAGGGCUACCUGUCCGCCCUCCGGACCGGGUGGUACACGAGCGUGAUCACCAUC
GAGCUGUCCAACAUCAAGGAGAACAAGUGCAACGGCACCGACGCGAAGGUGAAGCUGAUCAACC
AGGAGCUCGACAAGUACAAGAACGCCGUCACCGAGCUGCAGCUGCUCAUGCAGAGCACGACCGC
CGCCAACAACCGCGCGCGGCGCGAGCUGCCGCGGUUCAUGAACUACACCCUGAACAACACCAAG
AAGACGAACGUGACCCUCUCCAAGAAGCGCAAGCGGCGCUUCCUGGGGUUCCUGCUCGGCGUGG
GGAGCGCCAUCGCCUCCGGCAUCGCCGUCAGCAAGGUGCUGCACCUGGAGGGCGAGGUGAACAA
GAUCAAGUCCGCCCUCCUGAGCACCAACAAGGCGGUCGUGUCCCUGAGCAACGGGGUGUCCGUC
CUCACCAGCAAGGUGCUGGACCUGAAGAACUACAUCGACAAGCAGCUCCUGCCCAUCGUGAACA
AGCAGUCCUGCCGGAUCAGCAACAUCGAGACGGUCAUCGAGUUCCAGCAGAAGAACAACCGCCU
GCUCGAGAUCACCCGGGAGUUCAGCGUGAACGCCGGCGUGACCACCCCCGUCUCCACGUACAUG
CUGACCAACAGCGAGCUGCUCUCCCUGAUCAACGACAUGCCCAUCACCAACGACCAGAAGAAGC
UGAUGAGCAACAACGUGCAGAUCGUGCGCCAGCAGUCCUACAGCAUCAUGUCCAUCAUCAAGGA
GGAGGUCCUCGCCUACGUGGUGCAGCUGCCGCUGUACGGGGUCAUCGACACCCCCUGCUGGAAG
CUCCACACGAGCCCCCUGUGCACCACCAACACCAAGGAGGGCUCCAACAUCUGCCUGACGCGGA
CCGACCGCGGGUGGUACUGCGACAACGCCGGCAGCGUGUCCUUCUUCCCCAGGCCGAGACCUG
CAAGGUCCAGAGCAACCGGGUGUUCUGCGACACCAUGAACUCCCUCACGCUGCCGAGCGAGGUG
AACCUGUGCAACGUCGACAUCUUCAACCCCAAGUACGACUGCAAGAUCAUGACCUCCAAGACCG
ACGUGAGCUCCAGCGUGAUCACCUCCCUCGGCGCGAUCGUCAGCUGCUACGGGAAGACGAAGUG
CACCGCCAGCAACAAGAACCGCGGCAUCAUCAAGACCUUCUCCAACGGGUGCGACUACGUGAGC
AACAAGGGCGUGGACACCGUCUCCGUGGGCAACACCCUGUACUACGUGAACAAGCAGGAGGGGA
AGAGCCUGUACGUCAAGGGCGAGCCCAUCAUCAACUUCUACGACCCCCUCGUGUUCCCGUCCGA
CGAGUUCGACGCCAGCAUCUCCCAGGUGAACGAGAAGAUCAACCAGAGCCUGGCCUUCAUCCGG
AAGUCCGACGAGCUGCUGCACCACGUCAACGCCGGGAAGAGCACGACCAACAUCAUGAUCACCA
CCAUCAUCAUCGUGAUCAUCGUGAUCCUCCUGUCCCUGAUCGCGGUCGGCCUCCUGCUGUACUG
CAAGGCCCGCAGCACGCCCGUGACCCUCUCCAAGGACCAGCUGAGCGGGAUCAACAACAUCGCC
UUCUCCAACUGAGGACUAGUUAUAAGACUGACUAGCCCGAUGGGCCUCCCAACGGGCCCUCCUC
CCCUCCUUGCACCGAGAUUAAUAAAAAAAAAAAAAAAAAAAAAAAAAAAAAAAAAAAAAAAAAA
AAAAAAAAAAAAAAAAAAAAAUGCAUCCCCCCCCCCCCCCCCCCCCCCCCCCCCCCCCAAAGGC
UCUUUUCAGAGCCACCAGAAUU
```

FIG. 23

GC-enriched mRNA coding for F protein of RSV A2 (SEQ ID No. 20):

```
GGGAGAAAGCUUACCAUGGAGCUGCUCAUCCUGAAGGCCAACGCCAUCACCACCAUCCUGACGG
CGGUGACCUUCUGCUUCGCCAGCGGCCAGAACAUCACCGAGGAGUUCUACCAGUCCACCUGCAG
CGCCGUCUCCAAGGGGUACCUCAGCGCCCUGCGGACGGGCUGGUACACCUCCGUGAUCACCAUC
GAGCUGAGCAACAUCAAGGAGAACAAGUGCAACGGGACCGACGCCAAGGUGAAGCUCAUCAAGC
AGGAGCUGGACAAGUACAAGAACGCGGUCACGGAGCUGCAGCUCCUGAUGCAGUCCACCCCGCC
GACCAACAACCGCGCCCGGCGCGAGCUGCCCCGGUUCAUGAACUACACCCUCAACAACGCCAAG
AAGACGAACGUGACCCUGAGCAAGAAGCGCAAGCGGCGCUUCCUGGGCUUCCUCCUGGGGGUGG
GCUCCGCCAUCGCGAGCGGCGUCGCCGUGUCCAAGGUGCUGCACCUCGAGGGGGAGGUCAACAA
GAUCAAGAGCGCCCUGCUGUCCACCAACAAGGCCGUGGUGAGCCUCUCCAACGGCGUCAGCGUG
CUGACCUCCAAGGUGCUGGACCUCAAGAACUACAUCGACAAGCAGCUGCUGCCCAUCGUCAACA
AGCAGAGCUGCUCCAUCAGCAACAUCGAGACGGUGAUCGAGUUCCAGCAGAAGAACAACCGGCU
CCUGGAGAUCACCCGCGAGUUCAGCGUGAACGCCGGGGUCACCACCCCCGUGUCCACGUACAUG
CUGACCAACAGCGAGCUCCUGUCCCUGAUCAACGACAUGCCGAUCACCAACGACCAGAAGAAGC
UCAUGAGCAACAACGUGCAGAUCGUCCGGCAGCAGUCCUACAGCAUCAUGUCCAUCAUCAAGGA
GGAGGUGCUGGCGUACGUGGUCCAGCUGCCCCUCUACGGCGUGAUCGACACCCCCUGCUGGAAG
CUGCACACGAGCCCCCUGUGCACCACCAACACCAAGGAGGGGUCCAACAUCUGCCUCACGCGCA
CCGACCGGGGCUGGUACUGCGACAACGCCGGCAGCGUCUCCUUCUUCCCGCAGGCCGAGACCUG
CAAGGUGCAGAGCAACCGCGUGUUCUGCGACACCAUGAACUCCCUGACGCUGCCCAGCGAGAUC
AACCUCUGCAACGUCGACAUCUUCAACCCCAAGUACGACUGCAAGAUCAUGACCUCCAAGACCG
ACGUGAGCUCCAGCGUGAUCACCUCCCUGGGGGCCAUCGUCAGCUGCUACGGCAAGACGAAGUG
CACCGCCAGCAACAAGAACCGGGGGAUCAUCAAGACCUUCUCCAACGGCUGCGACUACGUGAGC
AACAAGGGCAUGGACACCGUGUCCGUCGGGAACACCCUGUACUACGUGAACAAGCAGGAGGGCA
AGAGCCUCUACGUGAAGGGGGAGCCCAUCAUCAACUUCUACGACCCGCUGGUCUUCCCCUCCGA
CGAGUUCGACGCGAGCAUCUCCCAGGUGAACGAGAAGAUCAACCAGAGCCUGGCCUUCAUCCGC
AAGUCCGACGAGCUGCUCCACAACGUGAACGCCGGCAAGAGCACGACCAACAUCAUGAUCACCA
CCAUCAUCAUCGUCAUCAUCGUGAUCCUGCUGUCCCUCAUCGCCGUGGGGCUGCUGCUCUACUG
CAAGGCCCGGAGCACGCCCGUCACCCUGUCCAAGGACCAGCUGAGCGGCAUCAACAACAUCGCG
UUCUCCAACUGAGGACUAGUUAUAAGACUGACUAGCCCGAUGGGCCUCCCAACGGGCCCUCCUC
CCCUCCUUGCACCGAGAUUAAUAAAAAAAAAAAAAAAAAAAAAAAAAAAAAAAAAAAAAAAAAA
AAAAAAAAAAAAAAAAAAAAAAAUGCAUCCCCCCCCCCCCCCCCCCCCCCCCCCCCCCAAAGGC
UCUUUUCAGAGCCACCAGAAUU
```

FIG. 24

GC-enriched mRNA coding for HA protein of Influenza A/Puerto Rico/8/1934 (SEQ ID No. 21):

GGGAGAAAGCUUACCAUGAAGGCCAACCUGCUCGUGCUGCUGUGCGCCCUCGCGGCCGCCGACG
CCGACACCAUCUGCAUCGGCUACCACGCCAACAACAGCACCGACACGGUCGACACCGUGCUGGA
GAAGAACGUGACCGUCACCCACUCCGUGAACCUGCUCGAGGACAGCCACAACGGGAAGCUGUGC
CGGCUGAAGGGCAUCGCGCCCCUCCAGCUGGGGAAGUGCAACAUCGCCGGCUGGCUGCUCGGGA
ACCCGGAGUGCGACCCCUGCUGCCCGUGCGCUCCGGAGCUACAUCGUCGAGACGCCCAACUC
CGAGAACGGCAUCUGCUACCCGGGCGACUUCAUCGACUACGAGGAGCUCCGGGAGCAGCUGAGC
UCCGUGAGCUCCUUCGAGCGCUUCGAGAUCUUCCCCAAGGAGAGCUCCUGGCCCAACCACAACA
CCAACGGGGUGACCGCCGCCUGCAGCCACGAGGGCAAGUCCAGCUUCUACCGGAACCUGCUCUG
GCUGACCGAGAAGGAGGGGUCCUACCCCAAGCUGAAGAACAGCUACGUCAACAAGAAGGGCAAG
GAGGUGCUCGUGCUGUGGGGGAUCCACCACCCGCCCAACUCCAAGGAGCAGCAGAACCUGUACC
AGAACGAGAACGCGUACGUCAGCGUGGUGACGUCCAACUACAACCGCCGGUUCACCCCCGAGAU
CGCCGAGCGCCCCAAGGUCCGGGACCAGGCCGGCCGCAUGAACUACUACUGGACCCUCCUGAAG
CCGGGCGACACCAUCAUCUUCGAGGCCAACGGGAACCUGAUCGCCCCGAUGUACGCGUUCGCCC
UCAGCCGGGGCUUCGGGAGCGGCAUCAUCACGUCCAACGCCAGCAUGCACGAGUGCAACACCAA
GUGCCAGACCCCCCUGGGCGCCAUCAACUCCAGCCUGCCCUACCAGAACAUCCACCCGGUGACC
AUCGGGGAGUGCCCCAAGUACGUGCGCUCCGCCAAGCUCCGGAUGGUCACGGGCCUGCGCAACA
ACCCCAGCAUCCAGUCCCGGGGGCUGUUCGGCGCGAUCGCCGGGUUCAUCGAGGGCGGCUGGAC
CGGGAUGAUCGACGGCUGGUACGGGUACCACCACCAGAACGAGCAGGGCAGCGGGUACGCCGCC
GACCAGAAGUCCACCCAGAACGCCAUCAACGGCAUCACCAACAAGGUGAACACGGUGAUCGAGA
AGAUGAACAUCCAGUUCACCGCGGUCGGCAAGGAGUUCAACAAGCUCGAGAAGCGCAUGGAGAA
CCUGAACAAGAAGGUGGACGACGGGUUCCUGGACAUCUGGACCUACAACGCCGAGCUCCUGGUG
CUGCUCGAGAACGAGCGGACCCUGGACUUCCACGACAGCAACGUCAAGAACCUGUACGAGAAGG
UGAAGUCCCAGCUCAAGAACAACGCCAAGGAGAUCGGCAACGGGUGCUUCGAGUUCUACCACAA
GUGCGACAACGAGUGCAUGGAGAGCGUCCGCAACGGCACGUACGACUACCCCAAGUACUCCGAG
GAGAGCAAGCUGAACCGGGAGAAGGUGGACGGGGUGAAGCUGGAGUCCAUGGGCAUCUACCAGA
UCCUCGCCAUCUACAGCACCGUCGCCUCCAGCCUGGUGCUGCUGGUGUCCCUCGGCGCGAUCAG
CUUCUGGAUGUGCAGCAACGGGUCCCUGCAGUGCCGCAUCUGCAUCUGACCACUAGUUAUAAGA
CUGACUAGCCCGAUGGGCCUCCCAACGGGCCCUCCUCCCCUCCUUGCACCGAGAUUAAUAAAAA
AAAAAAAAAAAAAAAAAAAAAAAAAAAAAAAAAAAAAAAAAAAAAAAAAAAAAAAAAAAAUGCAU
CCCCCCCCCCCCCCCCCCCCCCCCCCCCCAAAGGCUCUUUUCAGAGCCACCAGAAUU

FIG. 25

Non coding RNA (SEQ ID No. 23):

GGGAGAAAGCUCAAGCUUGGAGCAAUGCCCGCACAUUGAGGAAACCGAGUUGCAUAUCUCAGAG
UAUUGGCCCCCGUGUAGGUUAUUCUUGACAGACAGUGGAGCUUAUUCACUCCCAGGAUCCGAGU
CGCAUACUACGGUACUGGUGACAGACCUAGGUCGUCAGUUGACCAGUCCGCCACUAGACGUGAG
UCCGUCAAAGCAGUUAGAUGUUACACUCUAUUAGAUCUCGGAUUACAGCUGGAAGGAGCAGGAG
UAGUGUUCUUGCUCUAAGUACCGAGUGUGCCCAAUACCCGAUCAGCUUAUUAACGAACGGCUCC
UCCUCUUAGACUGCAGCGUAAGUGCGGAAUCUGGGGAUCAAAUUACUGACUGCCUGGAUUACCC
UCGGACAUAUAACCUUGUAGCACGCUGUUGCUGUAUAGGUGACCAACGCCCACUCGAGUAGACC
AGCUCUCUUAGUCCGGACAAUGAUAGGAGGCGCGGUCAAUCUACUUCUGGCUAGUUAAGAAUAG
GCUGCACCGACCUCUAUAAGUAGCGUGUCCUCUAG

FIG. 26

COMBINATION VACCINE

The present application is a divisional of U.S. application Ser. No. 16/781,781, filed Feb. 4, 2020, which is a divisional of U.S. application Ser. No. 15/048,561, filed Feb. 19, 2016, now U.S. Pat. No. 10,588,959, which is a continuation of International Application No. PCT/EP2014/002302, filed Aug. 21, 2014, which claims priority benefit of European Application No. PCT/EP2013/002513, filed Aug. 21, 2013, the entire text of each of the above referenced disclosures being specifically incorporated herein by reference.

The sequence listing that is contained in the file named "CRVCP0152USD2", which is 61 KB (as measured in Microsoft Windows®) and was created on Feb. 1, 2022, is filed herewith by electronic submission and is incorporated by reference herein.

The present invention relates to a vaccine, especially a combination vaccine providing at least a first and a second antigenic function, wherein the antigenic functions are encoded by at least one mRNA encoding at least one or more proteins or fragments, variants or derivatives of proteins awarding antigenic function, wherein the first antigenic function being a Fusion (F) protein or a fragment, variant or derivative of a Fusion (F) protein derived from the virus family Paramyxoviridae and the second antigenic function being an Hemagglutinin (HA) protein or a fragment, variant or derivative of an Hemagglutinin (HA) protein derived from the virus family Orthomyxoviridae. Furthermore, the present invention is directed to a kit or kit of parts comprising the components of said combination vaccine and to said combination vaccine for use in a method of prophylactic or therapeutic treatment of diseases, particularly in the prevention or treatment of infectious diseases like RSV and influenza.

Respiratory diseases caused by viruses or bacteria are a major health and economic burden worldwide. In this regard most prominent viral pathogens are respiratory syncytial virus (RSV), parainfluenza viruses 1-3 (PIV), and influenza A and B viruses, which are responsible for the majority of lower respiratory tract infections resulting in a significant rate of hospitalizations particularly of young children less than 3 years of age (Forster, J. et al., 2004. Prospective population-based study of viral lower respiratory tract infections in children under 3 years of age (the PRI.DE study). European Journal of Pediatrics, 163(12), S.709-716).

In this context, RSV which belongs to the virus family of Paramyxoviridae, is one of the most contagious pathogens and makes a substantial contribution to severe respiratory tract infections in infants, the elderly and immunocompromised patients.

As RSV, human parainfluenza viruses (PIV) belong to the virus family of Paramyxoviridae and are regarded as important pathogens likewise affecting the respiratory tract particularly of infants, children and the elderly. The subtypes 1 and 2 of PIV are the principal causes of croup, whereas subtype 3 causes more severe lower respiratory tract illness with RSV-like symptoms including pneumonia and bronchiolitis.

Paramyxoviruses are also responsible for a range of diseases in other animal species, for example canine distemper virus (dogs), phocine distemper virus (seals), cetacean morbillivirus (dolphins and porpoises), Newcastle disease virus (birds), and rinderpest virus (cattle). Some paramyxoviruses such as the henipaviruses are zoonotic pathogens, occurring naturally in an animal host, while being also able to infect humans. Hendra virus (HeV) and Nipah virus (NiV) in the genus Henipavirus have emerged in humans and are contagious, highly virulent, and capable of infecting a number of mammalian species and causing potentially fatal disease.

Paramyxoviridae typically do express a so called Fusion (F) protein which projects from the virus envelope surface and mediates cell entry by inducing a fusion process between the virus and the cell to be infected.

Influenza viruses, however, belong to the virus family Orthomyxoviridae and pose a high risk especially for infants, children and the elderly. Influenza viruses possess a segmented, negative-stranded RNA genome and are divided into three main types A, B, and C, of which type A is the most prominent one in humans. Influenza A viruses can be further subdivided based on different forms of the two surface glycoproteins Hemagglutinin (HA) and Neuraminidase (NA). The impact of seasonal influenza, characteristically a febrile disease with respiratory syndromes, has been estimated at 25-50 million cases per year worldwide. Due to the possibility of re-assortment of genetic material new variants of influenza viruses can emerge sporadically and spread worldwide (pandemic). Such re-assortment occurs most readily in pigs ("mixing vessels") resulting e.g. in the genesis of the swine-origin H1N1 in 2009 ("swine flu").

Currently, there are no approved vaccines against parainfluenza virus infection available; while available influenza vaccines are subunit, inactivated split or whole virion vaccines propagated in cell culture or chicken eggs which are not recommended for infants and only limited recommended for pregnant women.

With respect to RSV, a humanised monoclonal antibody against the viral surface F protein is the only prophylactic product on the market which is recommended for infants considered at high risk including pre-term infants and infants with chronic lung disease (The IMpact-RSV Study Group. 1998. Palivizumab, a Humanized Respiratory Syncytial Virus Monoclonal Antibody, Reduces Hospitalization From Respiratory Syncytial Virus Infection in High-risk Infants. Pediatrics, 102(3), S.531-537, Tablan et al. 2003. Guidelines for preventing health-care-associated pneumonia, 2003: recommendations of CDC and the Healthcare Infection Control Practices Advisory Committee. MMWR. Recommendations and Reports: Morbidity and Mortality Weekly Report. Recommendations and Reports/Centers for Disease Control, 53(RR-3), S.1-36).

Recent studies with animal models demonstrated that sufficient amounts of neutralising antibodies targeting RSV F protein limit viral replication leading to a less severe course of disease (Singh, S. R. et al., 2007. Immunogenicity and efficacy of recombinant RSV-F vaccine in a mouse model. Vaccine, 25(33), S.6211-6223, Zhan, X. et al., 2007. Respiratory syncytial virus (RSV) F protein expressed by recombinant Sendai virus elicits B-cell and T-cell responses in cotton rats and confers protection against RSV subtypes A and B. Vaccine, 25(52), S.8782-8793, Vaughan, K., et al., 2005. DNA immunization against respiratory syncytial virus (RSV) in infant rhesus monkeys. Vaccine, 23(22), S.2928-2942).

Moreover, it could be shown that a balanced regulatory and effector T cell function is required for viral clearance and reduction of severity of illness (Liu, J. et al., 2010. Epitope-specific regulatory CD4 T cells reduce virus-induced illness while preserving CD8 T-cell effector function at the site of infection. Journal of Virology, 84(20), S.10501-10509).

Despite the above mentioned humanised monoclonal antibody, live-attenuated vaccine viruses were developed which elicit a strong immune response, but which are not recommended for use in the specific target groups (infants, children, the elderly and immunocompromised patients).

Also, DNA vectors expressing RSV F protein which bears B-cell epitopes were used to induce the production of neutralizing antibodies. In this context, WO 2008/077527 and WO 96/040945 disclose vectors comprising DNA sequences encoding RSV F protein for the use as vaccines. However, the use of DNA as a vaccine may be dangerous due to unwanted insertion into the genome, possibly leading to interruption of functional genes and cancer or the formation of anti-DNA antibodies.

Furthermore, co-administration of vaccines based on polypeptides and/or DNA plasmids against different respiratory diseases has previously been reported. For example WO 2011/030218 discloses immunogenic compositions comprising viral (RSV and influenza) and bacterial (pneumococcus) immunogens, WO 00/35481 discloses combinations of RSV F, G and matrix proteins with a non-virulent influenza virus preparation, and WO 2010/149743 discloses combinations of F proteins derived from human metapneumovirus, parainfluenza virus and RSV. Furthermore, Talaat et al. (Talaat, A. M. et al. 2001. A combination vaccine confers full protection against co-infections with influenza, herpes simplex and respiratory syncytial viruses. Vaccine, 20(3-4), S.538-544) disclose a combination of DNA plasmid-driven vaccines against RSV, Herpes simplex virus (HSV) and Influenza A. Such a strategy, however, still requires administration of DNA based vectors. A further drawback, however, is the unknown compatibility between different co-administered novel vaccines e.g. by antigen competition.

Taken together, so far no approved RSV vaccine, especially no combination vaccine against additional respiratory diseases like influenza is available which can be administered particularly to the target groups (infants, children, the elderly and immunocompromised patients) without safety-concerns.

With respect to the problems and disadvantages of the known prior art as cited above, it is the object of the invention to provide a further vaccine or possibly even an improved vaccine. Particularly, it is the object of the invention to provide a (combination) vaccine against respiratory diseases caused by viruses of the Paramyxoviridae and/or the Orthomyxoviridae family, more particularly caused by RSV and/or influenza viruses.

Further, it is the object of the invention to provide a pharmaceutical composition or a kit comprising the (combination) vaccine or the respective components thereof. It is an object to provide a (combination) vaccine for use in a method of treatment of infections caused by viruses of the virus families Paramyxoviridae, e.g. RSV, and/or Orthomyxoviridae, e.g. Influenza virus.

It is an object of the invention to provide a vaccine that can be used as a combination vaccine against respiratory diseases caused by members of the virus families Paramyxoviridae and Orthomyxoviridae, particularly respiratory syncytial virus (RSV), parainfluenza viruses 1-3 (PIV), and Influenza A and B viruses and which induce a balanced immune response, i.e. a humoral and a cellular immune response.

Furthermore, it is the object of the invention to provide a method for the manufacturing of such a combination vaccine.

Likewise it is an object to provide a pharmaceutical composition or a vaccine that can be used as a vaccine for high risk groups like infants, children, the elderly or immunocompromised patients targeting the above mentioned pathogenic viruses in parallel, i.e. RSV, Parainfluenza and Influenza. Particularly, in the case of pre-term neonates it would be desirable that the vaccine could be applied as soon as possible after birth without safety-concerns or loss of efficacy.

These objects are solved by the subject matter of the present invention, in particular by the subject matter of the attached claims.

For the sake of clarity and readability the following scientific background information and definitions are provided. Any technical features disclosed thereby can be part of each and every embodiment of the invention. Additional definitions and explanations can be provided in the context of this disclosure.

Genome of RSV: RSV has 10 genes encoding 11 proteins—there are 2 open reading frames of M2. NS1 and NS2 inhibit type I interferon activity. N encodes nucleocapsid protein that associates with the genomic RNA forming the nucleocapsid. M encodes the Matrix protein required for viral assembly. SH, G and F form the viral coat. The "G" protein is a surface protein that is heavily glycosylated. It functions as the attachment protein. The "F" protein is another important surface protein; F mediates fusion, allowing entry of the virus into the cell cytoplasm and also allowing the formation of syncytia. The "F" protein is homologous in both subtypes of RSV; antibodies directed against the "F" protein are neutralizing. In contrast, the "G" protein differs considerably between the two subtypes. M2 is the second matrix protein also required for transcription, it encodes M2-1 (elongation factor) and M2-2 (transcription regulation), M2 contains CD8 epitopes. L encodes the RNA polymerase. The phosphoprotein P is a cofactor for L.

Genome of Influenza: Despite of all variations, the viral particles of all influenza viruses are similar in composition. These are made of a viral envelope containing two main types of glycoproteins, wrapped around a central core. The central core contains the viral RNA genome and other viral proteins that package and protect this RNA. Unusually for a virus, its genome is not a single piece of nucleic acid; instead, it contains seven or eight pieces of segmented negative-sense RNA, each piece of RNA containing either one or two genes, which code for a gene product (protein). For example, the influenza A genome contains 11 genes on eight pieces of RNA, encoding 11 proteins: hemagglutinin (HA), neuraminidase (NA), nucleoprotein (NP), M1, M2, NS1, NS2 (NEP: nuclear export protein), PA, PB1 (polymerase basic 1), PB1-F2 and PB2. Hemagglutinin (HA) and neuraminidase (NA) are the two large glycoproteins on the outside of the viral particles. HA is a lectin that mediates binding of the virus to target cells and entry of the viral genome into the target cell, while NA is involved in the release of progeny virus from infected cells, by cleaving sugars that bind the mature viral particles. Furthermore, they are antigens to which antibodies can be raised. Influenza A viruses are classified into subtypes based on antibody responses to HA and NA. These different types of HA and NA form the basis of the H and N distinctions in, for example, H5N1. There are 16H and 9 N subtypes known, but only H 1, 2 and 3, and N 1 and 2 are commonly found in humans.

Adaptive immune response: The adaptive immune response is typically understood to be antigen-specific. Antigen specificity allows for the generation of responses that are tailored to specific antigens, pathogens or pathogen-infected cells. The ability to mount these tailored responses is maintained in the body by "memory cells". Should a pathogen infect the body more than once, these specific memory cells are used to quickly eliminate it. In this context, the first step of an adaptive immune response is the activation of naïve antigen-specific T cells or different immune cells able to induce an antigen-specific immune response by antigen-presenting cells. This occurs in the lymphoid tissues and organs through which naïve T cells are constantly passing. Cell types that can serve as antigen-presenting cells are inter alia dendritic cells, macrophages, and B cells. Each of these cells has a distinct function in eliciting immune responses. Dendritic cells take up antigens by phagocytosis and macropinocytosis and are stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. Presenting the antigen on MHC molecules leads to activation of T cells which induces their proliferation and differentiation into armed effector T cells. The most important function of effector T cells is the killing of infected cells by CD8+ cytotoxic T cells and the activation of macrophages by Th1 cells which together make up cell-mediated immunity, and the activation of B cells by both Th2 and Th1 cells to produce different classes of antibody, thus driving the humoral immune response. T cells recognize an antigen by their T cell receptors which do not recognize and bind antigen directly, but instead recognize short peptide fragments e.g. of pathogen-derived protein antigens, which are bound to MHC molecules on the surfaces of other cells.

Adaptive immune system: The adaptive immune system is composed of highly specialized, systemic cells and processes that eliminate or prevent pathogenic growth. The adaptive immune response provides the vertebrate immune system with the ability to recognize and remember specific pathogens (to generate immunity), and to mount stronger attacks each time the pathogen is encountered. The system is highly adaptable because of somatic hypermutation (a process of increased frequency of somatic mutations), and V(D)J recombination (an irreversible genetic recombination of antigen receptor gene segments). This mechanism allows a small number of genes to generate a vast number of different antigen receptors, which are then uniquely expressed on each individual lymphocyte. Because the gene rearrangement leads to an irreversible change in the DNA of each cell, all of the progeny (offspring) of that cell will then inherit genes encoding the same receptor specificity, including the Memory B cells and Memory T cells that are the keys to long-lived specific immunity. Immune network theory is a theory of how the adaptive immune system works, that is based on interactions between the variable regions of the receptors of T cells, B cells and of molecules made by T cells and B cells that have variable regions.

Adjuvant/adjuvant component: An adjuvant or an adjuvant component in the broadest sense is typically a (e.g. pharmacological or immunological) agent or composition that may modify, e.g. enhance, the efficacy of other agents, such as a drug or vaccine. Conventionally the term refers in the context of the invention to a compound or composition that serves as a carrier or auxiliary substance for immunogens and/or other pharmaceutically active compounds. It is to be interpreted in a broad sense and refers to a broad spectrum of substances that are able to increase the immunogenicity of antigens incorporated into or co-administered with an adjuvant in question. In the context of the present invention an adjuvant will preferably enhance the specific immunogenic effect of the active agents of the present invention. Typically, "adjuvant" or "adjuvant component" has the same meaning and can be used mutually. Adjuvants may be divided, e.g., into immuno potentiators, antigenic delivery systems or even combinations thereof.

The term "adjuvant" is typically understood not to comprise agents which confer immunity by themselves. An adjuvant assists the immune system unspecifically to enhance the antigen-specific immune response by e.g. promoting presentation of an antigen to the immune system or induction of an unspecific innate immune response. Furthermore, an adjuvant may preferably e.g. modulate the antigen-specific immune response by e.g. shifting the dominating Th2-based antigen specific response to a more Th1-based antigen specific response or vice versa. Accordingly, an adjuvant may favourably modulate cytokine expression/secretion, antigen presentation, type of immune response etc.

Antigen: According to the present invention, the term "antigen" refers typically to a substance which may be recognized by the immune system and may be capable of triggering an antigen-specific immune response, e.g. by formation of antibodies or antigen-specific T-cells as part of an adaptive immune response. An antigen may be a protein or peptide. In this context, the first step of an adaptive immune response is the activation of naïve antigen-specific T cells by antigen-presenting cells. This occurs in the lymphoid tissues and organs through which naïve T cells are constantly passing. The three cell types that can serve as antigen-presenting cells are dendritic cells, macrophages, and B cells. Each of these cells has a distinct function in eliciting immune responses. Tissue dendritic cells take up antigens by phagocytosis and macropinocytosis and are stimulated by infection to migrate to the local lymphoid tissue, where they differentiate into mature dendritic cells. Macrophages ingest particulate antigens such as bacteria and are induced by infectious agents to express MHC class II molecules. The unique ability of B cells to bind and internalize soluble protein antigens via their receptors may be important to induce T cells. By presenting the antigen on MHC molecules leads to activation of T cells which induces their proliferation and differentiation into armed effector T cells. The most important function of effector T cells is the killing of infected cells by $CD8^+$ cytotoxic T cells and the activation of macrophages by TH1 cells which together make up cell-mediated immunity, and the activation of B cells by both TH2 and TH1 cells to produce different classes of antibody, thus driving the humoral immune response. T cells recognize an antigen by their T cell receptors which does not recognize and bind antigen directly, but instead recognize short peptide fragments e.g. of pathogens' protein antigens, which are bound to MHC molecules on the surfaces of other cells.

T cells fall into two major classes that have different effector functions. The two classes are distinguished by the expression of the cell-surface proteins CD4 and CD8. These two types of T cells differ in the class of MHC molecule that they recognize. There are two classes of MHC molecules—MHC class I and MHC class II molecules—which differ in their structure and expression pattern on tissues of the body. $CD4^+$ T cells bind to a MHC class II molecule and $CD8^+$ T cells to a MHC class I molecule. MHC class I and MHC class II molecules have distinct distributions among cells that reflect the different effector functions of the T cells that recognize them. MHC class I molecules present peptides of cytosolic and nuclear origin e.g. from pathogens, commonly viruses, to $CD8^+$ T cells, which differentiate into cytotoxic T cells that are specialized to kill any cell that they specifically recognize. Almost all cells express MHC class I molecules, although the level of constitutive expression varies from one cell type to the next. But not only pathogenic peptides from viruses are presented by MHC class I molecules, also self-antigens like tumour antigens are presented by them. MHC class I molecules bind peptides from proteins degraded in the cytosol and transported in the endoplasmic reticulum. The CD8$^+$ T cells that recognize MHC class I:peptide complexes at the surface of infected cells are specialized to kill any cells displaying foreign peptides and so rid the body of cells infected with viruses and other cytosolic pathogens. The main function of CD4$^+$ T cells (CD4$^+$ helper T cells) that recognize MHC class II molecules is to activate other effector cells of the immune system. Thus MHC class II molecules are normally found on B lymphocytes, dendritic cells, and macrophages, cells that participate in immune responses, but not on other tissue cells. Macrophages, for example, are activated to kill the intravesicular pathogens they harbour, and B cells to secrete immunoglobulins against foreign molecules. MHC class II molecules are prevented from binding to peptides in the endoplasmic reticulum and thus MHC class II molecules bind peptides from proteins which are degraded in endosomes. They can capture peptides from pathogens that have entered the vesicular system of macrophages, or from antigens internalized by immature dendritic cells or the immunoglobulin receptors of B cells. Pathogens that accumulate in large numbers inside macrophage and dendritic cell vesicles tend to stimulate the differentiation of TH1 cells, whereas extracellular antigens tend to stimulate the production of TH2 cells. TH1 cells activate the microbicidal properties of macrophages and induce B cells to make IgG antibodies that are very effective of opsonising extracellular pathogens for ingestion by phagocytic cells, whereas TH2 cells initiate the humoral response by activating naïve B cells to secrete IgM, and induce the production of weakly opsonising antibodies such as IgG1 and IgG3 (mouse) and IgG2 and IgG4 (human) as well as IgA and IgE (mouse and human).

Vaccine: A vaccine is typically understood to be a prophylactic or therapeutic material providing at least one antigen or antigenic function. The antigen or antigenic function may stimulate the body's adaptive immune system to provide an adaptive immune response.

Antibacterial agent: An antibacterial agent is typically a substance that may be effective against bacteria. The antibacterial agent may for example directly kill bacteria, reduce bacterial growth, and/or inhibit bacterial propagation and spreading. Examples for antibacterial agents are given further below.

Antiviral agent: An antiviral agent is typically a substance that may be effective against viruses. The antiviral agent may for example directly inactivate viruses, reduce viral replication, and/or inhibit viral propagation and spreading. Examples for antibacterial agents are given further below.

Antigenic function: An antigenic function may for example be an immunogen. Antigenic functions in the context of the present invention, however, also encompass mediators, i.e. nucleic acids which do show an antigenic function in vivo if they code for antigenic proteins/peptides. Such carriers having antigenic function as understood in the context of the inventions may be expressed by the nucleic acid in vivo which in turn leads to the presence of proteins or peptides that may act as an immunogen. Accordingly, in the context of the invention, an antigenic function is typically a component that can lead directly (direct antigenic functionality/directly acting antigenic function) or indirectly (indirect antigenic functionality/indirectly acting antigenic function) to the presence of an antigen within an organism when introduced into this organism. In this context, direct antigenic functionality typically means that the antigenic function is, e.g., a protein or peptide (or a killed bacterium, virus or the like) that is administered to an organism and induces an adaptive immune response, mostly without being modified by e.g. translation or the like. However, indirect antigenic functionality typically means in this context that the "antigenic function" is, e.g., a nucleic acid sequence that is taken up by the target organism and translated within the organism into a peptide or protein. This peptide or protein then functions as an immunogen and induces an adaptive immune response. Thus, in one variant, an "antigenic function" is understood to be a preform or precursor of an immunogen. Also, an "antigenic function" can be understood to be an immunogen itself. In the context of the present invention, an antigenic function may in particular be a Fusion (F) protein of the virus family Paramyxoviridae and (e.g. artificial) functional variants or fragments thereof as well as (preferably immunogenic) fragments of said Fusion (F) protein and respective variants; as well as corresponding nucleic acids encoding any of these, i.e. Fusion (F) proteins of the virus family Paramyxoviridae, variants thereof as well as fragments of said Fusion (F) protein and respective variants. In the context of the present invention, an antigenic function may also in particular be a Hemagglutinin (HA) protein of the virus family Orthomyxoviridae and (e.g. artificial) variants thereof as well as (preferably immunogenic) fragments of said Hemagglutinin (HA) protein and respective variants; as well as corresponding nucleic acids encoding any of these, i.e. Hemagglutinin (HA) proteins of the virus family Orthomyxoviridae, variants thereof as well as fragments of said Hemagglutinin (HA) protein and respective variants. Fusion (F) proteins of the virus family Paramyxoviridae and their amino acid sequence and (e.g. artificial) variants thereof may for example be identified in established databases such as the UniProt database or the Protein database provided by the National Center for Biotechnology (NCBI, US). Hemagglutinin (HA) proteins of the virus family Orthomyxoviridae and (e.g. artificial) variants thereof may for instance likewise be identified in databases such as the UniProt database or the Protein database provided by the National Center for Biotechnology (NCBI, US). Antigenic function preferably represents the immune response elicited by a protein or peptide sequence. The antigenic function or the antigenic potential of the HA and F protein is typically sequence specific and depends on specific epitope sequences within the full-length protein. Accordingly, the antigens function in terms of the T cell response typically depends on T cell epitopes, which is typically evoked by peptide (fragments) of a length of between 8 and 11 amino acids (for presentation by MHC class I molecules), whereas B cell epitopes (for presentation on MHC class II molecules) are typically longer peptides of 13-17 amino acids in length. The antigenic function(s) may preferably be understood as the immunological potential or immunogenicity (for triggering a T- and B cell response), which is due to the characteristic T and B cell epitopes of the full-length protein, e.g. the HA or F protein. The fragments, variants or derivatives of the full-length protein shall typically retain the same immunological potential as the full-length HA or F proteins to reflect their antigenic function.

Antigen-providing RNA: An antigen-providing RNA (in particular an antigen-providing mRNA) in the context of the invention may typically be a RNA, having at least one open reading frame that can be translated by a cell or an organism provided with that RNA. The product of this translation is a peptide or protein that may act as an antigen, preferably as an immunogen. The product may also be a fusion protein composed of more than one immunogen, e.g. a fusion protein that consist of two or more epitopes, peptides or proteins derived from the same or different virus-proteins, wherein the epitopes, peptides or proteins may be linked by linker sequences.

Bi-/multicistronic RNA: RNA, preferably an mRNA, that typically may have two (bicistronic) or more (multicistronic) open reading frames (ORF). An open reading frame in this context is a sequence of several nucleotide triplets (codons) that can be translated into a peptide or protein. Translation of such RNA yields two (bicistronic) or more (multicistronic) distinct translation products (provided the ORFs are not identical). For expression in eukaryotes such RNA may for example comprise an internal ribosomal entry site (IRES) sequence.

Fragments or variants of nucleic acids: These fragments or variants may typically comprise a sequence having a sequence identity with a nucleic acid, or with a protein or peptide, if encoded by the nucleic acid molecule, of at least 5%, 10%, 20%, 30%, 40%, 50%, 60%, preferably at least 70%, more preferably at least 80%, equally more preferably at least 85%, even more preferably at least 90% and most preferably at least 95% or even 97%, 98% or 99%, to the entire wild type sequence, either on nucleic acid level or on amino acid level.

Carrier/polymeric carrier: A carrier in the context of the invention may typically be a compound that facilitates transport and/or complexation of another compound. Said carrier may form a complex with said other compound. A polymeric carrier is a carrier that is formed of a polymer.

Cationic component: The term "cationic component" typically refers to a charged molecule, which is positively charged (cation) at a pH value of typically about 1 to 9, preferably of a pH value of or below 9 (e.g. 5 to 9), of or below 8 (e.g. 5 to 8), of or below 7 (e.g. 5 to 7), most preferably at physiological pH values, e.g. about 7.3 to 7.4. Accordingly, a cationic peptide, protein or polymer according to the present invention is positively charged under physiological conditions, particularly under physiological salt conditions of the cell in vivo. A cationic peptide or protein preferably contains a larger number of cationic amino acids, e.g. a larger number of Arg, His, Lys or Orn than other amino acid residues (in particular more cationic amino acids than anionic amino acid residues like Asp or Glu) or contains blocks predominantly formed by cationic amino acid residues. The definition "cationic" may also refer to "polycationic" components.

5'-Cap-Structure: A 5' cap is typically a modified nucleotide, particularly a guanine nucleotide, added to the 5' end of a RNA-molecule. Preferably, the 5'cap is added using a 5'-5'-triphosphate linkage.

Cellular immunity/cellular immune response: Cellular immunity relates typically to the activation of macrophages, natural killer cells (NK), antigen-specific cytotoxic T-lymphocytes, and the release of various cytokines in response to an antigen. In a more general way, cellular immunity is not related to antibodies but to the activation of cells of the immune system. A cellular immune response is characterized e.g. by activating antigen-specific cytotoxic T-lymphocytes that are able to induce apoptosis in body cells displaying epitopes of an antigen on their surface, such as virus-infected cells, cells with intracellular bacteria, and cancer cells displaying tumor antigens; activating macrophages and natural killer cells, enabling them to destroy pathogens; and stimulating cells to secrete a variety of cytokines that influence the function of other cells involved in adaptive immune responses and innate immune responses.

Combination vaccine: A combination vaccine is typically a vaccine that may provide two or more immunogens and/or antigenic functions. The immunogens and/or antigenic functions are provided simultaneously by one composition.

Fragments of proteins: "Fragments" of proteins or peptides in the context of the present invention may, typically, comprise a sequence of a protein or peptide as defined herein, which is, with regard to its amino acid sequence (or its encoded nucleic acid molecule), N-terminally and/or C-terminally truncated compared to the amino acid sequence of the original (native) protein (or its encoded nucleic acid molecule). Such truncation may thus occur either on the amino acid level or correspondingly on the nucleic acid level. A sequence identity with respect to such a fragment as defined herein may therefore preferably refer to the entire protein or peptide as defined herein or to the entire (coding) nucleic acid molecule of such a protein or peptide. Likewise, "fragments" of nucleic acids in the context of the present invention may comprise a sequence of a nucleic acid as defined herein, which is, with regard to its nucleic acid molecule 5'- and/or 3'-truncated compared to the nucleic acid molecule of the original (native) nucleic acid molecule. A sequence identity with respect to such a fragment as defined herein may therefore preferably refer to the entire nucleic acid as defined herein.

Fragments of proteins or peptides in the context of the present invention may furthermore comprise a sequence of a protein or peptide as defined herein, which has a length of for example at least 5 amino acids, preferably a length of at least 6 amino acids, preferably at least 7 amino acids, more preferably at least 8 amino acids, even more preferably at least 9 amino acids; even more preferably at least 10 amino acids; even more preferably at least 11 amino acids; even more preferably at least 12 amino acids; even more preferably at least 13 amino acids; even more preferably at least 14 amino acids; even more preferably at least 15 amino acids; even more preferably at least 16 amino acids; even more preferably at least 17 amino acids; even more preferably at least 18 amino acids; even more preferably at least 19 amino acids; even more preferably at least 20 amino acids; even more preferably at least 25 amino acids; even more preferably at least 30 amino acids; even more preferably at least 35 amino acids; even more preferably at least 50 amino acids; or most preferably at least 100 amino acids. For example such fragment may have a length of about 6 to about 20 or even more amino acids, e.g. fragments as processed and presented by MHC class I molecules, preferably having a length of about 8 to about 10 amino acids, e.g. 8, 9, or 10, (or even 6, 7, 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognized in their native form. Fragments of proteins or peptides may comprise at least one epitope of those proteins or peptides. Furthermore also domains of a protein, like the extracellular domain, the intracellular domain or the transmembrane domain and shortened or truncated versions of a protein may be understood to comprise a fragment of a protein. The fragment may be chosen as mentioned from any part of the full length protein or peptide. For example, the fragment of a Fusion (F) protein of the virus family Paramyxoviridae, and/or the fragment of the Hemagglutinin (HA) protein of the virus family Orthomyxoviridae, may be selected, independently of each other, from the first, second, third or fourth quarter of the amino acid sequence of said Fusion (F) protein of the virus family Paramyxoviridae and/or the amino acid sequence of said Hemagglutinin (HA) protein of the virus family Orthomyxoviridae, respectively.

Epitope (also called "antigen determinant"): T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule.

B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

Variants of proteins: "Variants" of proteins or peptides as defined in the context of the present invention may be generated, having an amino acid sequence which differs from the original sequence in one or more mutation(s), such as one or more substituted, inserted and/or deleted amino acid(s). Preferably, these fragments and/or variants have the same biological function or specific activity compared to the full-length native protein, e.g. its specific antigenic property. "Variants" of proteins or peptides as defined in the context of the present invention may comprise conservative amino acid substitution(s) compared to their native, i.e. non-mutated physiological, sequence. Those amino acid sequences as well as their encoding nucleotide sequences in particular fall under the term variants as defined herein. Substitutions in which amino acids, which originate from the same class, are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

Furthermore, variants of proteins or peptides as defined herein, which may be encoded by a nucleic acid molecule, may also comprise those sequences, wherein nucleotides of the nucleic acid are exchanged according to the degeneration of the genetic code, without leading to an alteration of the respective amino acid sequence of the protein or peptide, i.e. the amino acid sequence or at least part thereof may not differ from the original sequence in one or more mutation(s) within the above meaning.

In order to determine the percentage to which two sequences are identical, e.g. nucleic acid sequences or amino acid sequences as defined herein, preferably the amino acid sequences encoded by a nucleic acid sequence of the polymeric carrier as defined herein or the amino acid sequences themselves, the sequences can be aligned in order to be subsequently compared to one another. Therefore, e.g. a position of a first sequence may be compared with the corresponding position of the second sequence. If a position in the first sequence is occupied by the same component (residue) as is the case at a position in the second sequence, the two sequences are identical at this position. If this is not the case, the sequences differ at this position. If insertions occur in the second sequence in comparison to the first sequence, gaps can be inserted into the first sequence to allow a further alignment. If deletions occur in the second sequence in comparison to the first sequence, gaps can be inserted into the second sequence to allow a further alignment. The percentage to which two sequences are identical is then a function of the number of identical positions divided by the total number of positions including those positions which are only occupied in one sequence. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program. A "variant" of a protein or peptide may have at least 70%, 75%, 80%, 85%, 90%, 95%, 98% or 99% amino acid identity over a stretch of 10, 20, 30, 50, 75 or 100 amino acids of such protein or peptide. Analogously, a "variant" of a nucleic acid sequence may have at least 70%, 75%, 80%, 85%, 90%, 95%, 98% or 99% nucleotide identity over a stretch of 10, 20, 30, 50, 75 or 100 nucleotide of such nucleic acid sequence Derivative of a protein or peptide: A derivative of a peptide or protein is typically understood to be a molecule that is derived from another molecule, such as said peptide or protein. A "derivative" of a peptide or protein also encompasses fusions comprising a peptide or protein used in the present invention. For example, the fusion comprises a label, such as, for example, an epitope, e.g., a FLAG epitope or a V5 epitope. For example, the epitope is a FLAG epitope. Such a tag is useful for, for example, purifying the fusion protein.

Fusion protein: A fusion protein is typically an artificial peptide or protein. Fusion proteins are typically created through the joining of two or more open reading frames which originally coded for separate peptides or proteins wherein joining may optionally occur via a linker sequence. These joined open reading frames are typically translated in a single peptide, polypeptide or protein with functional properties derived from each of the original proteins or peptides. A person skilled in the art will be readily aware, that the definition of the term "Fusion protein" does not relate to the terms "Fusion (F) protein" or F protein, which instead refer to a specific class of viral proteins (see above).

Humoral immunity/humoral immune response: Humoral immunity refers typically to antibody production and the accessory processes that may accompany it. A humoral immune response may be typically characterized, e.g., by Th2 activation and cytokine production, germinal center formation and isotype switching, affinity maturation and memory cell generation. Humoral immunity also typically may refer to the effector functions of antibodies, which include pathogen and toxin neutralization, classical complement activation, and opsonin promotion of phagocytosis and pathogen elimination.

Immunogen: An immunogen is preferably a protein or peptide, e.g. the product of an in vivo translation of a provided antigenic function. Typically, an immunogen may elicit at least or exclusively an adaptive immunogen/antigen-specific immune response. In the context of the present invention, an immunogen may in particular be a (F) protein of the virus family Paramyxoviridae and (e.g. artificial) variants thereof as well as immunogenic fragments of said Fusion (F) protein and respective variants. In the context of the present invention, an immunogen may also in particular be a Hemagglutinin (HA) protein of the virus family Orthomyxoviridae and (e.g. artificial) variants thereof as well as immunogenic fragments of said Hemagglutinin (HA) protein and respective variants.

Immune response: An immune response may typically either be a specific reaction of the adaptive immune system to a particular antigen (so called specific or adaptive immune response) or an unspecific reaction of the innate immune system (so called unspecific or innate immune response). The invention relates to the core to specific reactions (adaptive immune responses) of the adaptive immune system. Particularly, it relates to adaptive immune responses to infections by viruses like e.g. RSV or influenza. However, this specific response can be supported by an additional unspecific reaction (innate immune response). Therefore, the invention also relates to a compound for simultaneous stimulation of the innate and the adaptive immune system to evoke an efficient adaptive immune response.

Immune system: The immune system may protect organisms from infection. If a pathogen breaks through a physical barrier of an organism and enters this organism, the innate immune system provides an immediate, but non-specific response. If pathogens evade this innate response, vertebrates possess a second layer of protection, the adaptive immune system. Here, the immune system adapts its response during an infection to improve its recognition of the pathogen. This improved response is then retained after the pathogen has been eliminated, in the form of an immunological memory, and allows the adaptive immune system to mount faster and stronger attacks each time this pathogen is encountered. According to this, the immune system comprises the innate and the adaptive immune system. Each of these two parts contains so called humoral and cellular components.

Immunostimulatory RNA: An immunostimulatory RNA (isRNA) in the context of the invention may typically be a RNA that is able to induce an innate immune response itself. It usually does not have an open reading frame and thus does not provide a peptide-antigen or immunogen but elicits an innate immune response e.g. by binding to a specific kind of Toll-like-receptor (TLR) or other suitable receptors. However, of course also mRNAs having an open reading frame and coding for a peptide/protein (e.g. an antigenic function) may induce an innate immune response.

Innate immune system: The innate immune system, also known as non-specific immune system, comprises the cells and mechanisms that defend the host from infection by other organisms in a non-specific manner. This means that the cells of the innate system recognize and respond to pathogens in a generic way, but unlike the adaptive immune system, it does not confer long-lasting or protective immunity to the host. The innate immune system may be e.g. activated by ligands of pathogen-associated molecular patterns (PAMP) receptors, e.g. Toll-like receptors (TLRs) or other auxiliary substances such as lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (isRNA), a CpG-DNA, an antibacterial agent, or an anti-viral agent. Typically a response of the innate immune system includes recruiting immune cells to sites of infection, through the production of chemical factors, including specialized chemical mediators, called cytokines; activation of the complement cascade; identification and removal of foreign substances present in organs, tissues, the blood and lymph, by specialized white blood cells; activation of the adaptive immune system through a process known as antigen presentation; and/or acting as a physical and chemical barrier to infectious agents.

Monocistronic RNA: A monocistronic RNA may typically be a RNA, preferably a mRNA, that encodes only one open reading frame. An open reading frame in this context is a sequence of several nucleotide triplets (codons) that can be translated into a peptide or protein.

Nucleic acid: The term nucleic acid means any DNA- or RNA-molecule and is used synonymous with polynucleotide. Wherever herein reference is made to a nucleic acid or nucleic acid sequence encoding a particular protein and/or peptide, said nucleic acid or nucleic acid sequence, respectively, preferably also comprises regulatory sequences allowing in a suitable host, e.g. a human being, its expression, i.e. transcription and/or translation of the nucleic acid sequence encoding the particular protein or peptide.

Peptide: A peptide is a polymer of amino acid monomers. Usually the monomers are linked by peptide bonds. The term "peptide" does not limit the length of the polymer chain of amino acids. In some embodiments of the present invention a peptide may for example contain less than 50 monomer units. Longer peptides are also called polypeptides, typically having 50 to 600 monomeric units, more specifically 50 to 300 monomeric units.

Pharmaceutically effective amount: A pharmaceutically effective amount in the context of the invention is typically understood to be an amount that is sufficient to induce an immune response.

Protein: A protein typically consists of one or more peptides and/or polypeptides folded into 3-dimensional form, facilitating a biological function.

Poly (C) sequence: A poly-(C)-sequence is typically a long sequence of cytosine nucleotides, typically about 10 to about 200 cytosine nucleotides, preferably about 10 to about 100 cytosine nucleotides, more preferably about 10 to about 70 cytosine nucleotides or even more preferably about 20 to about 50 or even about 20 to about 30 cytosine nucleotides. A poly(C) sequence may preferably be located 3' of the coding region comprised by a nucleic acid.

Poly-A-tail: A poly-A-tail also called "3'-poly(A) tail" is typically a long sequence of adenosine nucleotides of up to about 400 adenosine nucleotides, e.g. from about 25 to about 400, preferably from about 50 to about 400, more preferably from about 50 to about 300, even more preferably from about 50 to about 250, most preferably from about 60 to about 250 adenosine nucleotides, added to the 3' end of a RNA.

Polyadenylation signal: Polyadenylation is typically the addition of a Poly-A-Tail to a RNA, particularly to an mRNA. It is induced by a so called polyadenylation signal. This signal may be typically located at the 3'-end of a RNA to be polyadenylated and may typically comprise a hexamer consisting of adenine and uracil, preferably the hexamer AAUAAA. Other hexamer sequences are conceivable.

Stabilized nucleic acid: A stabilized nucleic acid, typically, exhibits a modification increasing resistance to in vivo degradation (e.g. degradation by an exo- or endo-nuclease) and/or ex vivo degradation (e.g. by the manufacturing process prior to vaccine administration, e.g. in the course of the preparation of the vaccine solution to be administered). Stabilization of RNA can, e.g., be achieved by providing a 5'Cap-Structure, a Poly-A-Tail, or any other UTR-modification. It can also be achieved by backbone-modification or modification of the G/C-content of the nucleic acid. Various other methods are known in the art and conceivable in the context of the invention.

Vaccine: A vaccine is typically understood to be a prophylactic or therapeutic material providing at least one antigenic function, particularly an immunogen. The antigen or immunogen stimulates the body's adaptive immune system to provide an adaptive immune response.

Vehicle: An agent, e.g. a carrier, that may typically be used within a vaccine for facilitating administering of the immunogenic composition and/or the antigenic function to an individual.

In a first aspect, the invention provides a combination vaccine providing at least a first and a second antigenic function; the combination vaccine comprising at least one RNA (preferably mRNA) encoding at least one or more proteins or fragments, variants or derivatives of proteins awarding the antigenic functions; wherein the first antigenic function being a Fusion (F) protein or a fragment, variant or derivative of a Fusion (F) protein derived from the virus family Paramyxoviridae and the second antigenic function being an Hemagglutinin (HA) protein or a fragment, variant or derivative of an Hemagglutinin (HA) protein derived from the virus family Orthomyxoviridae.

It can easily be recognised that each RNA encoding an antigenic function is an antigen-providing RNA according to the above given definition. The immuno-active component (that means the component that causes an interaction with the immune system of the treated individual to provoke preferably an adaptive immune response) is at least one antigen-providing RNA. As an example the combination vaccine can contain either one antigen-providing RNA that encodes both or all antigenic functions or two or more distinct antigen-providing RNAs encoding both or all antigenic functions.

According to the invention the RNA in the combination vaccine may for example be an mRNA. However, other forms of RNA may likewise find its application in carrying out the teaching of the present invention by providing mRNA. For example, the RNA may be a virus derived RNA vector such as a retrovirus or an alphavirus derived RNA replicon vector. A retrovirus is an RNA virus that is duplicated in a host cell using the reverse transcriptase enzyme to produce DNA from its RNA genome. The DNA is then incorporated into the host's genome by an integrase enzyme. The virus thereafter replicates as part of the host cell's DNA and then undergoes the usual transcription and translational processes to express the genes carried by the virus. Alphaviruses are single stranded RNA viruses in which heterologous genes of interest may substitute for the alphavirus' structural genes. By providing the structural genes in trans, the replicon RNA is packaged into replicon particles (RP) which may be used for example for vaccination (see for example Vander Veen et al., 2012. Alphavirus replicon vaccines. Animal Health Research Reviews, p. 1-9). After entry into the host cell, the genomic viral RNA initially serves as an mRNA for translation of the viral nonstructural proteins (nsPs) required for initiation of viral RNA amplification. RNA replication occurs via synthesis of a full-length minusstrand intermediate that is used as the template for synthesis of additional genome-length RNAs and for transcription of a plus-strand subgenomic RNA from an internal promoter. Such RNA may then be considered as self replicating RNA, since the non-structural proteins responsible for replication (and transcription of the heterologous genes) are still present in such replicon. The Fusion (F) protein and the Hemagglutinin (HA) protein as encoded by said RNA (e.g. mRNA or viral RNA) are defined as either being full-length proteins or being fragments, variants or derivatives of the proteins, wherein fragments, variants and derivatives of the proteins are understood as defined above. The encoded proteins or fragments, variants or derivatives of the proteins may be antigens, particularly immunogens. It is also possible that the coding sequence of the Fusion (F) protein and/or the Hemagglutinin (HA) protein is distributed over two or more RNAs and/or over two or more open reading frames. The two or more RNAs and/or two or more open reading frames will in such scenario encode several distinct fragments of the Fusion (F) protein and/or the Hemagglutinin (HA) protein.

According to the present invention, the inventive combination vaccine comprising at least one RNA providing these antigenic functions (HA protein and F protein, or fragments, variants or derivatives thereof) does show an unexpectedly remarkable synergistic effect. Particularly, it was unexpectedly found by the inventors that such a combination vaccine comprising RNAs encoding a Fusion (F) protein of the virus family Paramyxoviridae, particularly RSV and a Hemagglutinin (HA) protein of the virus family Orthomyxoviridae, particularly Influenza, or fragments, variants or derivatives thereof, provides an improved Fusion (F) protein-specific immune response, particularly a superior specific T cell response compared to vaccination with mRNA coding solely for the Fusion (F) protein. The combination vaccine according to the invention is thus preferably suitable to elicit an antigen-specific immune response in a patient. Herein, the mRNA encoded Fusion (F) protein and Hemagglutinin (HA) protein, respectively their fragments, variants or derivatives, serve as antigens. In this context, it may be preferred that the RNA encoding the Fusion (F) protein or a fragment, variant or derivative thereof of the virus family Paramyxoviridae, and the RNA encoding the Hemagglutinin (HA) protein or a fragment, variant or derivative thereof of the virus family Orthomyxoviridae are comprised in the same composition of the combination vaccine. One single composition enables the locally and timely simultaneous application of different antigens, which may be considered to be particularly advantageous in this specific application, because it improves the T cell response directed against the F protein. Furthermore, it reduces the number of injections required to prevent the diseases and minimizes the costs of stocking separate vaccines.

Quasi-simultaneous administration may, alternatively, be also achieved by subsequent administration (within e.g. up to 10 minutes, more preferably within two minutes) of a combination vaccine which is composed of e.g. two separate compositions, wherein the first composition contains RNA encoding the Fusion (F) protein or a fragment, variant or derivative thereof of the virus family Paramyxoviridae, and the second composition contains the RNA encoding the Hemagglutinin (HA) protein or a fragment, variant or derivative thereof of the virus family Orthomyxoviridae. In case of subsequent administration, it is preferred to administer both compositions at the same site of the body or at least close to each other such that the same area of the patient's lymphatic system is addressed by both administrations, thereby triggering an immune response which as coherent as an immune response triggered by the administration of a combination vaccine composed one single composition containing mRNA molecules encoding both antigenic functions. Accordingly, a "staggered" combination vaccine may, alternatively, be provided by subsequent administration by separate compositions, each composition comprising distinct immunogens and/or antigenic functions. By subsequent administration however, a immune response is to be triggered which is comparable to the coherent immune response achieved by the administration of one single composition, i.e. the synergistic effect on e.g. the immune response against the F protein.

Besides, this approach according to the invention shows the potential of an RNA based vaccine allowing simultaneous vaccination against viruses belonging to the virus families Paramyxoviridae and Orthomyxoviridae, respectively, by combination of RNA vaccines encoding relevant viral antigens. The combination of RNAs encoding the Fusion (F) protein or a fragment, variant or derivative thereof of e.g. RSV strains and the Hemagglutinin (HA) protein or a fragment, variant or derivative thereof of e.g. Influenza viruses was shown to specifically enhance the adaptive immune response against the e.g. RSV F protein in an unexpected way. Thus, the combination vaccine according to the invention provides not only a mixture of RNAs encoding different antigens (of two distinct viruses) but also an unexpected synergistic effect for the F protein specific T cell immune response.

Any functional fragment, variant or derivative of the Fusion (F) protein or the Hemagglutinin (HA) protein, which may be encoded by the RNAs of the inventive combination vaccine shall advantageously trigger the same synergistic immune response as the corresponding full-length proteins, in particular the same specific T cell immune response and preferably also the same B-cell response, as observed for the full-length protein-based combination vaccine, against the F protein of e.g. RSV. The "same" in this regard means of "the same order of magnitude". The T cell or B cell immune responses against the F protein (or its functional fragments, derivatives or variants) may be measured as shown in Examples 4 and 5 (FIGS. 1 to 3) herein. Typically, any functional fragment, variant or derivative of the full-length F or HA proteins contains the decisive epitopes of the full-length HA or F protein sequences such that the immune response is not decreased due to less antigenic potential of the fragments, variant or derivative.

In a specific embodiment of the first aspect of the invention, the antigenic functions are provided by the combination vaccine in the form of monocistronic RNAs, whereby a first monocistronic RNA encodes said Fusion (F) protein or said fragment, variant or derivative thereof and a second monocistronic RNA encodes said Hemagglutinin (HA) protein or said fragment, variant or derivative thereof.

In another embodiment, the antigenic functions are provided by the combination vaccine in the form of a bicistronic or a multicistronic RNA. For example, the bi- or multicistronic RNA may contain at least one open reading frame, which encodes said Fusion (F) protein or said fragment, variant or derivative thereof and wherein at least one other open reading frame encodes said Hemagglutinin (HA) protein or said fragment, variant or derivative thereof. Hereby, both antigenic functions are provided by one single RNA molecule. More generally, however, such a bi- or multicistronic RNA may encode, e.g., two or even more coding sequences of at least two antigenic functions, as defined above. Accordingly, a bi- or multicistronic RNA may e.g. contain distinct antigenic functions of the Fusion (F) protein only (e.g. derived from the same or from different RSV strains), whereas another bi- or multicistronic RNA may, e.g., contain distinct antigenic functions of the Hemagglutinin (HA) protein (derived e.g. from the same or from different Influenza strains).

Accordingly, it is encompassed by the invention that the combination vaccine comprises a first bi- or multicistronic RNA encoding for an ensemble of Fusion (F) proteins or fragments, variants or derivatives thereof derived from different Paramyxoviridae and a second monocistronic RNA encoding for a Hemagglutinin (HA) protein derived from a virus belonging to the Orthomyxoviridae, or the other way around.

The coding sequences of such bi- or multicistronic RNAs, e.g. the ORFs of the at least two antigenic functions, may be separated by at least one internal ribosomal entry site (IRES) sequence. This so-called IRES sequence can function as a sole ribosome binding site, but it can also serve to provide a bi- or even multicistronic RNA as defined herein which codes for several antigens, which are to be translated by the ribosomes independently of one another. Examples of IRES sequences which can be used according to the invention are those from picornaviruses (e.g. FMDV), pestiviruses (CFFV), polioviruses (PV), encephalomyocarditis viruses (ECMV), foot and mouth disease viruses (FMDV), hepatitis C viruses (HCV), classical swine fever viruses (CSFV), mouse leukemia virus (MLV), simian immunodeficiency viruses (SIV) or cricket paralysis viruses (CrPV).

In another embodiment according to the first aspect of the invention, the antigenic functions are provided by the combination vaccine in the form of a monocistronic RNA encoding the Fusion (F) protein or a fragment, variant or derivative thereof and encoding the Hemagglutinin (HA)

protein or a fragment, variant or derivative thereof as a fusion protein. By such a fusion protein, e.g. the full-length sequences of the Fusion (F) protein and the full-length sequence of the Hemagglutinin (HA) protein are linked with or without a linker sequence. Alternatively, such a fusion protein may contain a full-length protein sequence of the Fusion (F) protein and only parts of the Hemagglutinin (HA) protein (or vice versa) or may contain parts of either both of these proteins. Preferred are RNAs encoding fusion proteins which are composed of one or more antigenic peptide sequences, encoding epitopes of the Fusion (F) and/or the Hemagglutinin (HA) protein that can individually act as immunogens. These epitopes of each of these proteins are preferably arranged in a non-native way, which means that the epitope sequences are isolated from the native sequences and are linked by non-native linker sequences (e.g linker sequences having more than 50% glycine and proline residues). Generally, however, inventive monocistronic RNAs encoding such fusion proteins may be provided with or without linker sequences. Such linker sequences typically comprise 5 to 25 amino acids, preferably selected from proline and glycine. Preferably, the linker sequence is immunologically neutral. e.g. non-immunogenic and non-immunostimulatory.

It is preferred that the at least one Fusion (F) protein is derived from viruses selected from: Avulavirus, Ferlavirus, Henipavirus, Morbillivirus, Respirovirus, Rubulavirus, TPMV-like viruses, Pneumovirus, Metapneumovirus, Atlantic salmon paramyxovirus, Beilong virus, J virus, Mossman virus, Nariva virus, Salem virus, or Pacific salmon paramyxovirus. Avulavirus can be e.g. Newcastle disease virus; Ferlavirus can be e.g. Fer-de-Lance virus; Henipavirus can be e.g. Hendravirus, Nipahvirus; Morbillivirus can be e.g. Measles virus, Rinderpest virus, Canine distemper virus, Phocine distemper virus, Peste des Petits Ruminants virus (PPR); Respirovirus can be e.g. Sendai virus, Human Parainfluenza viruses 1 and 3, viruses of the common cold; Rubulavirus can be e.g. Mumps virus, Human Parainfluenza viruses 2 and 4, Simian Parainfluenza virus 5, Menangle virus, Tioman virus, Tuhokovirus 1, 2 and 3; TPMV-like viruses can be e.g. Tupaia paramyxovirus; Pneumovirus can be e.g. Human respiratory syncytial virus, Bovine respiratory syncytial virus; and Metapneumovirus which can be e.g. Avian pneumovirus, Human metapneumovirus. Particularly, it is preferred that the Fusion (F) protein is derived from human respiratory syncytial virus (RSV), preferably selected from RSV Long (preferably according to SEQ ID No. 1) or RSV A2 (preferably according to SEQ ID No. 2 or mutants thereof such as P102A, I379V or M447V), more preferably the Fusion (F) protein is a protein encoded at least partially by one of the nucleic acid sequences according to SEQ ID No. 4, SEQ ID No. 5, SEQ ID No. 7, SEQ ID No. 8, SEQ ID No. 9, SEQ ID No. 10, SEQ ID No. 11, SEQ ID No. 13, SEQ ID No. 14, SEQ ID No. 15, SEQ ID No. 16, SEQ ID No. 17, SEQ ID No. 19, or SEQ ID No. 20.

The combination vaccine of the invention can contain an ensemble of more than one antigenic function derived from distinct Fusion (F) proteins, which may either be derived from distinct strains of e.g. the above viruses or derived from (e.g. the above) different viruses or may be a combination of both. They may be provided distinct RNA molecules (more than one type) or by a single RNA molecule (one type). If provided by one single RNA type, the distinct antigenic functions may be provided by a monocistronic type of RNA encoding a fusion protein presenting these distinct antigenic functions or by a bi- or multicistronic RNA coding for distinct antigenic functions. Of course, the above embodiments may be combined and do not exclude each other.

It is further preferred that the at least one Hemagglutinin (HA) protein is derived from an Influenza virus, preferably selected from: Influenza A (e.g. H1N1, H1N2, H2N2, H3N1, H3N2, H3N8, H5N1, H5N2, H5N3, H5N8, H5N9, H7N1, H7N2, H7N3, H7N4, H7N7, H9N1, H9N2, H10N7), Influenza B, Influenza C, Isavirus (e.g. Infectious salmon anemia virus), Thogotovirus (e.g. Dhori virus), Quaranfil virus, Johnston Atoll virus, or Lake Chad virus, more preferably the HA protein is a protein according to SEQ ID No. 3, more preferably the Hemagglutinin (HA) protein is a protein encoded at least partially by the nucleic acid sequence according to SEQ ID No. 6, SEQ ID No: 12, SEQ ID No: 18, or SEQ ID No. 21. More preferably, the HA protein as encoded by any of the above SEQ ID Nos. may be combined, e.g. for providing one single composition comprising at least two nucleic acids, e.g. SEQ ID No. 18 or SEQ ID No. 21, with a F protein encoded by any of the following SEQ ID Nos. 13, 14, 15, 16, 17, 19 and 20. Accordingly, e.g. SEQ ID No. 18 or SEQ ID No. 21 may be combined for the combination vaccine, e.g. in the form of one single composition or as a staggered combination vaccine, with SEQ ID No. 13, alternatively, with SEQ ID No. 14. or alternatively with SEQ ID No. 15, or alternatively with SEQ ID No: 16, or alternatively SEQ ID No. 17 or alternatively SEQ ID No 19 or alternatively SEQ ID No 20.

The combination vaccine of the invention can contain an ensemble of more than one antigenic function derived from distinct Hemagglutinin (HA) proteins, which may either be derived from distinct strains of e.g. the above viruses or derived from (e.g. the above) different viruses or may be a combination of both. They may be provided by more distinct RNA molecules (more than one type) or by a single RNA molecule (one type). If provided by one single RNA type, the distinct antigenic functions may be provided by a monocistronic type of RNA encoding a fusion protein presenting these distinct antigenic functions or a bi- or multicistronic RNA coding for distinct antigenic functions. Of course, the above embodiments may be combined and do not exclude each other. The at least one RNA of the inventive combination vaccine (or any further nucleic acid as defined herein) may be stabilized in order to prevent instability and (fast) degradation of the RNA (or any further nucleic acid molecule) by various approaches. This instability of RNA is typically due to RNA-degrading enzymes, "RNases" (ribonucleases), wherein contamination with such ribonucleases may sometimes completely degrade RNA in solution. Accordingly, the natural degradation of RNA in the cytoplasm of cells is very finely regulated and RNase contaminations may be generally removed by special treatment prior to use of said compositions, in particular with diethyl pyrocarbonate (DEPC). A number of mechanisms of natural degradation are known in this connection in the prior art, which may be utilized as well. E.g., the terminal structure is typically of critical importance particularly for an mRNA. As an example, at the 5' end of naturally occurring mRNAs there is usually a so-called cap structure, which is a modified guanosine nucleotide also called 5'Cap structure, and at the 3' end is typically a sequence of up to 200 adenosine nucleotides (the so-called poly-A tail). By a further embodiment the at least one RNA comprises at least one of the following structural elements: a histone-stem-loop structure, preferably a histone-stem-loop in its 3' untranslated region, a 5'Cap structure, a poly(C) sequence, a poly-A tail and/or a polyadenylation signal, preferably as defined herein.

By a further embodiment, the at least one RNA preferably comprises at least two of the following structural elements: a 5' and/or 3'-stabilizing sequence; a histone-stem-loop structure, preferably a histone-stem-loop in its 3' untranslated region; a 5'-Cap structure; a poly(C) sequence; a poly-A tail; or a polyadenylation signal, e.g. given a 5'-Cap structure and a histone-stem-loop and, potentially a poly-A-tail.

Stabilizing sequences in the 5' and/or 3' untranslated regions have the effect of increasing the half-life of the nucleic acid in the cytosol. These stabilizing sequences can have 100% sequence identity to naturally occurring sequences which occur in viruses, bacteria and eukaryotes, but can also be partly or completely synthetic. The untranslated sequences (UTR) of the (alpha-)globin gene, e.g. from *Homo sapiens* or *Xenopus laevis* may be mentioned as an example of stabilizing sequences which can be used in the present invention for a stabilized nucleic acid.

Another example of a stabilizing sequence has the general formula $(C/U)CCAN_xCCC(U/A)Py_xUC(C/U)CC$ which is contained in the 3' UTR of the very stable RNA which codes for (alpha-)globin, type(I)-collagen, 15-lipoxygenase or for tyrosine hydroxylase (cf. Holcik et al., Proc. Natl. Acad. Sci. USA 1997, 94: 2410 to 2414). Such stabilizing sequences can of course be used individually or in combination with one another and also in combination with other stabilizing sequences known to a person skilled in the art.

A histone stem-loop sequence, suitable to be used within the present invention, is preferably selected from at least one of the following formulae (I) or (II):

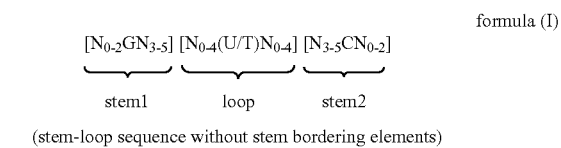

(stem-loop sequence without stem bordering elements)

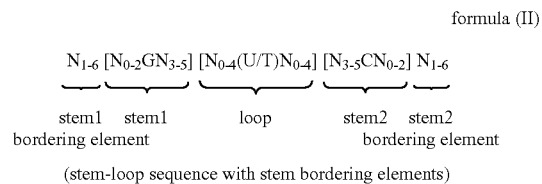

(stem-loop sequence with stem bordering elements)

wherein:

| | |
|---|---|
| stem1 or stem2 bordering elements $N_{1-6}$ | is a consecutive sequence of 1 to 6, preferably of 2 to 6, more preferably of 2 to 5, even more preferably of 3 to 5, most preferably of 4 to 5 or 5 N, wherein each N is independently from another selected from a nucleotide selected from A, U, T, G and C, or a nucleotide analogue thereof; |
| stem1 $[N_{0-2}GN_{3-5}]$ | is reverse complementary or partially reverse complementary with element stem2, and is a consecutive sequence between of 5 to 7 nucleotides; wherein $N_{0-2}$ is a consecutive sequence of 0 to 2, preferably of 0 to 1, more preferably of 1 N, wherein each N is independently from another selected from a nucleotide selected from A, U, T, G and C or a nucleotide analogue thereof; wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof, and wherein G is guanosine or an analogue thereof, and may be optionally replaced by a cytidine or an analogue thereof, provided that its complementary nucleotide cytidine in stem2 is replaced by guanosine; |
| loop sequence $[N_{0-4}(U/T)N_{0-4}]$ | is located between elements stem1 and stem2, and is a consecutive sequence of 3 to 5 nucleotides, more preferably of 4 nucleotides; wherein each $N_{0-4}$ is independent from another a consecutive sequence of 0 to 4, preferably of 1 to 3, more preferably of 1 to 2 N, wherein each N is independently from another selected from a nucleotide selected from A, U, T, G and C or a nucleotide analogue thereof; and wherein U/T represents uridine, or optionally thymidine; |
| stem2 $[N_{3-5}CN_{0-2}]$ | is reverse complementary or partially reverse complementary with element stem1, and is a consecutive sequence between of 5 to 7 nucleotides; wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof; wherein $N_{0-2}$ is a consecutive sequence of 0 to 2, preferably of 0 to 1, more preferably of 1 N, wherein each N is independently from another selected from a nucleotide selected from A, U, T, G or C or a nucleotide analogue thereof; and | wherein C is cytidine or an analogue thereof, and may be optionally replaced by a guanosine or an analogue thereof provided that its complementary nucleoside guanosine in stem1 is replaced by cytidine;

wherein stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one ore more bases in one stem do not have a complementary base in the reverse complementary sequence of the other stem.

A further optionally comprised stabilizing element is a poly(A) sequence, also called poly-A-tail at the 3'-terminus of the at least one RNA. When present, such a poly(A) sequence comprises a sequence of about 25 to about 400 adenosine nucleotides, preferably a sequence of about 50 to about 400 adenosine nucleotides, more preferably a sequence of about 50 to about 300 adenosine nucleotides, even more preferably a sequence of about 50 to about 250 adenosine nucleotides, most preferably a sequence of about 60 to about 250 adenosine nucleotides. In this context the term "about" refers to a deviation of ±10% of the value(s) it is attached to.

According to a further preferred embodiment the at least one RNA of the inventive combination vaccine or any further nucleic acid comprised in the inventive combination vaccine as defined herein, can be modified by a sequence of at least 10 cytosines, preferably at least 20 cytosines, more preferably at least 30 cytosines (so-called "poly(C) sequence"). Particularly, the nucleic acid molecule may contain or code for a poly(C) sequence of typically about 10 to 200 cytosine nucleotides, preferably about 10 to 100 cytosine nucleotides, more preferably about 10 to 70 cytosine nucleotides or even more preferably about 20 to 50 or even 20 to 30 cytosine nucleotides. This poly(C) sequence is preferably located 3' of the coding region comprised in the nucleic acid particularly in the at least one RNA according to the first aspect of the present invention.

In this context it is particularly preferred that the at least one RNA encoding at least one Fusion (F) protein or a fragment, variant or derivative thereof of the virus family Paramyxoviridae and at least one Hemagglutinin (HA) protein or a fragment, variant or derivative thereof of the virus family Orthomyxoviridae (or any other coding nucleic acid comprised in the inventive combination vaccine) has the following structure in 5' to 3'-direction:

a) a coding region, preferably encoding a peptide or protein as defined above;
b) at least one histone stem-loop, optionally without a histone downstream element 3' to the histone stem-loop
c) a poly(A) sequence or a polyadenylation signal.

In another particular preferred embodiment the at least one RNA encoding at least one Fusion (F) protein or a fragment, variant or derivative thereof of the virus family Paramyxoviridae and at least one Hemagglutinin (HA) protein or a fragment, variant or derivative thereof of the virus family Orthomyxoviridae (or any other coding nucleic acid comprised in the inventive combination vaccine) has the following structure in 5' to 3'-direction:

a) a coding region, preferably encoding a peptide or protein as defined above;
b) a poly(A) sequence; and
c) at least one histone stem-loop.

The coding region might be or might comprise at least partially the coding region of one of the sequences according to SEQ ID No. 4 to SEQ ID No. 21. Particularly, the RNA might be or might comprise at least partially one of the sequences according to SEQ ID No. 4 to SEQ ID No. 21. Furthermore, the RNA (e.g. mRNA) might comprise a combination of at least two of these sequences or a combination of fragments or variants thereof. Thereby, at least one sequence is preferably selected from SEQ ID No. 19; or SEQ ID No. 20, and a further sequence is preferably selected from SEQ ID No. 21. Other combinations can of course be imagined as well.

For further improvement of the resistance to e.g. in vivo degradation (e.g. by an exo- or endo-nuclease), the at least one RNA of the inventive combination vaccine or any further nucleic acid comprised in the inventive combination vaccine may be provided as a stabilized nucleic acid, e.g. in the form of a modified nucleic acid. According to a further embodiment of the invention it is therefore preferred that the at least one RNA or any further nucleic acid comprised in the inventive combination vaccine is stabilized, preferably by backbone modifications, sugar modifications and/or base modifications, more preferred stabilized by modification of the G/C-content. All of these modifications may be introduced into the at least one RNA without impairing the RNA's function to be translated into the antigenic function derived from the Fusion (F) protein or the Hemagglutinin (HA) protein or any further encoded protein or peptide.

A backbone modification in the context of the present invention is preferably a modification in which phosphates of the backbone of the nucleotides contained in the at least one RNA of the inventive combination vaccine (or any further nucleic acid as defined herein) are chemically modified, e.g. anionic internucleoside linkage, N3'→P5' modifications, replacement of non-bridging oxygen atoms by boranes, neutral internucleoside linkage, amide linkage of the nucleosides, methylene(methylimino) linkages, formacetal and thioformacetal linkages, introduction of sulfonyl groups, or the like.

A sugar modification in the context of the present invention is preferably a chemical modification of the sugar of the nucleotides of the at least one RNA of the inventive combination vaccine (or any further nucleic acid as defined herein), e.g. methylation of the ribose residue or the like.

According to another embodiment, the at least one RNA of the inventive combination vaccine or any further coding nucleic acid comprised in the inventive combination vaccine may be modified and thus stabilized by modifying the G (guanosine)/C (cytosine) content of the mRNA, preferably of the coding region thereof.

Therein, the G/C content of the at least one RNA of the inventive combination vaccine or any further coding nucleic acid comprised in the inventive combination vaccine is particularly increased compared to the G/C content of the coding region of its particular wild type coding sequence, i.e. the unmodified RNA. However, the encoded amino acid sequence of the RNA or coding nucleic acid is preferably not modified compared to the coded amino acid sequence of the particular wild type RNA or coding nucleic acid.

The modification of the G/C-content of the at least one RNA of the inventive combination vaccine or any further coding nucleic acid comprised in the inventive combination vaccine is based on the fact that RNA sequences having an increased G (guanosine)/C (cytosine) content are more stable than RNA sequences having an increased A (adenosine)/U (uracil) content. The codons of a coding sequence or a whole RNA might therefore be varied compared to the wild type coding sequence or mRNA, such that they include an increased amount of G/C nucleotides while the translated amino acid sequence is retained. In respect to the fact that several codons code for one and the same amino acid (so-called degeneration of the genetic code), the most favourable codons for the stability can be determined (so-called alternative codon usage). Preferably, the G/C content of the coding region of the at least one RNA of the inventive combination vaccine or any further coding nucleic acid comprised in the inventive combination vaccine according to the invention is increased by at least 7%, more preferably by at least 15%, particularly preferably by at least 20%, compared to the G/C content of the coded region of the wild type RNA. According to a specific embodiment at least 5%, 10%, 20%, 30%, 40%, 50%, 60%, more preferably at least 70%, even more preferably at least 80% and most preferably at least 90%, 95% or even 100% of the substitutable codons in the region coding for a protein or peptide as defined herein or its fragment or variant thereof or the whole sequence of the wild type RNA sequence or coding sequence are substituted, thereby increasing the G/C content of said sequence. In this context, it is particularly preferable to increase the G/C content of the at least one RNA of the inventive combination vaccine or any further coding nucleic acid comprised in the inventive combination vaccine to the maximum (i.e. 100% of the substitutable codons), in particular in the region coding for a protein, compared to the wild type sequence.

According to a further preferred embodiment of the invention, the at least one RNA or any further coding nucleic acid comprised in the inventive combination vaccine is optimized for translation, preferably optimized for translation by replacing codons for less frequent tRNAs of a given amino acid by codons for more frequently occurring tRNAs of the respective amino acid. This is based on the finding that the translation efficiency is also determined by a different frequency in the occurrence of tRNAs in cells. Thus, if so-called "less frequent codons" are present in the at least one RNA of the inventive combination vaccine or any further coding nucleic acid comprised in the inventive combination vaccine to an increased extent, the corresponding modified RNA is translated to a significantly poorer degree than in the case where codons coding for more frequent tRNAs are present. Preferably, the coding region of the at least one RNA of the inventive combination vaccine or any further coding nucleic acid comprised in the inventive combination vaccine is modified compared to the corresponding region of the wild type RNA or coding sequence such that at least one codon of the wild type sequence which codes for a tRNA which is relatively rare or less frequent in the cell is exchanged for a codon which codes for a tRNA which is more or most frequent in the cell and carries the same amino acid as the relatively rare or less frequent tRNA. By this modification, the sequences of the at least one RNA of the inventive combination vaccine or any further coding nucleic acid comprised in the inventive combination vaccine can be modified such that codons for which more frequently occurring tRNAs are available are inserted. In other words, according to the invention, by this modification all codons of the wild type sequence which code for a tRNA which is relatively rare in the cell can in each case be exchanged for a codon which codes for a respective tRNA which is relatively frequent in the cell and which, in each case, carries the same amino acid as the relatively rare tRNA. Furthermore, it is particularly preferable to link the sequential G/C content which is increased, in particular maximized, in the modified at least one RNA of the inventive combination vaccine or any further coding nucleic acid comprised in the combination vaccine with the "frequent" codons without modifying the amino acid sequence of the protein encoded by the coding region of the RNA or of the coding nucleic acid. This preferred embodiment allows provision of a particularly efficiently translated and stabilized (modified) at least one RNA of the combination vaccine or any further nucleic acid comprised in the inventive combination vaccine.

Substitutions, additions or eliminations of bases are preferably carried out using a DNA matrix for preparation of the nucleic acid molecule by techniques of the well known site directed mutagenesis or with an oligonucleotide ligation. In such a process, for preparation of the at least one RNA of the inventive combination vaccine as defined herein a corresponding DNA molecule may be transcribed in vitro. This DNA matrix preferably comprises a suitable promoter, e.g. a T7 or SP6 promoter, for in vitro transcription, which is followed by the desired nucleotide sequence for the at least one RNA to be prepared and a termination signal for in vitro transcription. The DNA molecule, which forms the matrix of the at least one RNA of interest, may be prepared by fermentative proliferation and subsequent isolation as part of a plasmid which can be replicated in bacteria. Plasmids which may be mentioned as suitable for the present invention are e.g. the plasmids pT7 Ts (GenBank accession number U26404; Lai et al., Development 1995, 121: 2349 to 2360), pGEM® series, e.g. pGEM®-1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, FL, 2001.

Additionally, nucleic acid molecules used, e.g. the at least one RNA of the inventive combination vaccine or any further nucleic acid molecule as defined herein, may be prepared using any method known in the art, including synthetic methods such as e.g. solid phase synthesis, as well as in vitro methods, such as in vitro transcription reactions.

According to one embodiment of the present invention the at least one RNA of the inventive combination vaccine or any further nucleic acid comprised in the inventive combination vaccine may be administered naked without being associated with any further vehicle, transfection or complexation agent for increasing the transfection efficiency and/or the immunostimulatory properties of the at least one RNA or of further comprised nucleic acid.

In another preferred embodiment, the at least one RNA of the inventive combination vaccine or any other nucleic acid comprised in the inventive combination vaccine according to the invention may be formulated together with a cationic or polycationic compound and/or with a polymeric carrier. Accordingly, in a further embodiment of the invention it is preferred that the at least one RNA or any other nucleic acid comprised in the inventive combination vaccine is associated with or complexed with a cationic or polycationic compound or a polymeric carrier, optionally in a weight ratio selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w) of RNA to cationic or polycationic compound and/or with a polymeric carrier; or optionally in a nitrogen/phosphate ratio of RNA to cationic or polycationic compound and/or polymeric carrier in the range of about 0.1-10, preferably in a range of about 0.3-4 or 0.3-1, and most preferably in a range of about 0.5-1 or 0.7-1, and even most preferably in a range of about 0.3-0.9 or 0.5-0.9.

Thereby, the at least one RNA of the inventive combination vaccine or any other nucleic acid comprised in the inventive combination vaccine can also be associated with a vehicle, transfection or complexation agent for increasing the transfection efficiency and/or the immunostimulatory properties of the at least one RNA or of optionally comprised further included nucleic acids.

Cationic or polycationic compounds, being particularly preferred agents in this context include protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, pIsl, FGF, Lactoferrin, Transportan, Buforin-2, Bac715-24, SynB, SynB(1), pVEC, hCT-derived peptides, SAP, or histones.

In this context protamine is particularly preferred.

Additionally, preferred cationic or polycationic proteins or peptides may be selected from the following proteins or peptides having the following total formula (III):

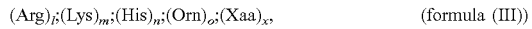

$(Arg)_l;(Lys)_m;(His)_n;(Orn)_o;(Xaa)_x$, (formula (III))

wherein $l+m+n+o+x=8-15$, and 1, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred cationic peptides in this context are e.g. $Arg_7$, $Arg_8$, $Arg_9$, $H_3R_9$, $R_9H_3$, $H_3R_9H_3$, $YSSR_9SSY$, $(RKH)_4$, $Y(RKH)_2R$, etc.

Further preferred cationic or polycationic compounds, which can be used as transfection or complexation agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl]trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole); etc.

A polymeric carrier according to the invention might be a polymeric carrier formed by disulfide-crosslinked cationic components. The disulfide-crosslinked cationic components may be the same or different from each other. The polymeric carrier can also contain further components. It is also particularly preferred that the polymeric carrier of the present invention comprises mixtures of cationic peptides, proteins or polymers and optionally further components as defined herein, which are crosslinked by disulfide bonds as described herein.

In this context the cationic components, which form basis for the polymeric carrier by disulfide-crosslinkage, are typically selected from any suitable cationic or polycationic peptide, protein or polymer suitable for this purpose, particular any cationic or polycationic peptide, protein or polymer capable to complex a nucleic acid as defined according to the present invention, and thereby preferably condensing the nucleic acid. The cationic or polycationic peptide, protein or polymer, is preferably a linear molecule, however, branched cationic or polycationic peptides, proteins or polymers may also be used.

Every disulfide-crosslinking cationic or polycationic protein, peptide or polymer of the polymeric carrier, which may be used to complex the at least one RNA of the combination vaccine or any further nucleic acid comprised in the combination vaccine contains at least one —SH moiety, most preferably at least one cysteine residue or any further chemical group exhibiting an —SH moiety, capable to form a disulfide linkage upon condensation with at least one further cationic or polycationic protein, peptide or polymer as cationic component of the polymeric carrier as mentioned herein.

As defined above, the polymeric carrier, which may be used to complex the at least one RNA of the combination vaccine or any further nucleic acid comprised in the combination vaccine may be formed by disulfide-crosslinked cationic (or polycationic) components.

According to one first alternative, at least one cationic (or polycationic) component of the polymeric carrier, which may be used to complex the at least one RNA of the inventive combination vaccine or any further nucleic acid comprised in the inventive combination vaccine may be selected from cationic or polycationic peptides or proteins. Such cationic or polycationic peptides or proteins preferably exhibit a length of about 3 to 100 amino acids, preferably a length of about 3 to 50 amino acids, more preferably a length of about 3 to 25 amino acids, e.g. a length of about 3 to 10, 5 to 15, 10 to 20 or 15 to 25 amino acids. Alternatively or additionally, such cationic or polycationic peptides or proteins may exhibit a molecular weight of about 0.01 kDa to about 100 kDa, including a molecular weight of about 0.5 kDa to about 100 kDa, preferably of about 10 kDa to about 50 kDa, even more preferably of about 10 kDa to about 30 kDa.

In the specific case that the cationic component of the polymeric carrier, which may be used to complex the at least one RNA of the inventive combination vaccine or any further nucleic acid comprised in the inventive combination vaccine comprises a cationic or polycationic peptide or protein, the cationic properties of the cationic or polycationic peptide or protein or of the entire polymeric carrier, if the polymeric carrier is entirely composed of cationic or polycationic peptides or proteins, may be determined upon its content of cationic amino acids. Preferably, the content of cationic amino acids in the cationic or polycationic peptide or protein and/or the polymeric carrier is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 15% to 75%, even more preferably in the range of about 20% to 50%, e.g. 20, 30, 40 or 50%, or in a range formed by any two of the afore mentioned values, provided, that the content of all amino acids, e.g. cationic, lipophilic, hydrophilic, aromatic and further amino acids, in the cationic or polycationic peptide or protein, or in the entire polymeric carrier, if the polymeric carrier is entirely composed of cationic or polycationic peptides or proteins, is 100%.

Preferably, such cationic or polycationic peptides or proteins of the polymeric carrier, which comprise or are additionally modified to comprise at least one —SH moiety, are selected from, without being restricted thereto, cationic peptides or proteins such as protamine, nucleoline, spermine or spermidine, oligo- or poly-L-lysine (PLL), basic polypeptides, oligo or poly-arginine, cell penetrating peptides (CPPs), chimeric CPPs, such as Transportan, or MPG peptides, HIV-binding peptides, Tat, HIV-1 Tat (HIV), Tat-derived peptides, members of the penetratin family, e.g. Penetratin, Antennapedia-derived peptides (particularly from *Drosophila antennapedia*), pAntp, pIsl, etc., antimicrobial-derived CPPs e.g. Buforin-2, Bac715-24, SynB, SynB(1), pVEC, hCT-derived peptides, SAP, MAP, PpTG20, Loligomere, FGF, Lactoferrin, histones, VP22 derived or analog peptides, Pestivirus Erns, HSV, VP22 (Herpes simplex), MAP, KALA or protein transduction domains (PTDs, PpT620, prolin-rich peptides, arginine-rich peptides, lysine-rich peptides, Pep-1, L-oligomers, Calcitonin peptide(s), etc.

Alternatively or additionally, such cationic or polycationic peptides or proteins of the polymeric carrier, which comprise or are additionally modified to comprise at least one —SH moiety, are selected from, without being restricted thereto, following cationic peptides having the following sum formula (IV):

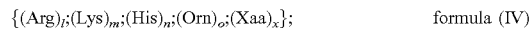

wherein l+m+n+o+x=3-100, and 1, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Orn (Ornithine) represents at least 10% of all amino acids of the oligopeptide; and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide. Any of amino acids Arg, Lys, His, Orn and Xaa may be positioned at any place of the peptide. In this context cationic peptides or proteins in the range of 7-30 amino acids are particular preferred. Even more preferred peptides of this formula are oligoarginines such as e.g. $Arg_7$, $Arg_8$, $Arg_9$, $Arg_{12}$, $His_3Arg_9$, $Arg_9His_3$, $His_3Arg_9His_3$, $His_6Arg_9His_6$, $His_3Arg_4His_3$, $His_6Arg_4His_6$, $TyrSer_2Arg_9Ser_2Tyr$, $(ArgLysHis)_4$, $Tyr(ArgLysHis)_2Arg$, etc.

According to a one further particular preferred embodiment, the cationic or polycationic peptide or protein of the polymeric carrier, when defined according to formula $\{(Arg)_l; (Lys)_m; (His)_n; (Orn)_o; (Xaa)_x\}$ (formula (IV)) as shown above and which comprises or is additionally modified to comprise at least one —SH moiety, may be, without being restricted thereto, selected from subformula (IVa):

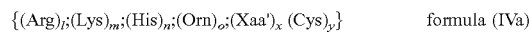

wherein $(Arg)_l$; $(Lys)_m$; $(His)_n$; $(Orn)_o$; and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide.

This embodiment may apply to situations, wherein the cationic or polycationic peptide or protein of the polymeric carrier, e.g. when defined according to empirical formula $(Arg)_l$; $(Lys)_m$; $(His)_n$; $(Orn)_o$; $(Xaa)_x$ (formula (IV)) as shown above, comprises or has been modified with at least one cysteine as —SH moiety in the above meaning such that the cationic or polycationic peptide as cationic component carries at least one cysteine, which is capable to form a disulfide bond with other components of the polymeric carrier.

According to another particular preferred embodiment, the cationic or polycationic peptide or protein of the polymeric carrier, when defined according to formula $\{(Arg)_l; (Lys)_m; (His)_n; (Orn)_o; (Xaa)_x\}$ (formula (IV)) as shown above, may be, without being restricted thereto, selected from subformula (IVb):

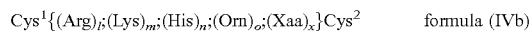

wherein empirical formula $\{(Arg)_l; (Lys)_m; (His)_n; (Orn)_o; (Xaa)_x\}$ (formula (IV)) is as defined herein and forms a core of an amino acid sequence according to (semiempirical) formula (IV) and wherein $Cys^1$ and $Cys^2$ are Cysteines proximal to, or terminal to $(Arg)_l$; $(Lys)_m$; $(His)_n$; $(Orn)_o$; $(Xaa)_x$. This embodiment may apply to situations, wherein the cationic or polycationic peptide or protein of the polymeric carrier, which may be used to complex the at least one RNA of the inventive combination vaccine, e.g. when defined according to empirical formula $(Arg)_l$; $(Lys)_m$; $(His)_n$; $(Orn)_o$; $(Xaa)_x$ (formula (IV)) as shown above, has been modified with at least two cysteines as —SH moieties in the above meaning such that the cationic or polycationic peptide of the inventive polymeric carrier carries at least two (terminal) cysteines, which are capable to form a disulfide bond with other components of the polymeric carrier.

According to a second alternative, at least one cationic (or polycationic) component of the polymeric carrier may be selected from e.g. any (non-peptidic) cationic or polycationic polymer suitable in this context, provided that this (non-peptidic) cationic or polycationic polymer exhibits or is modified to exhibit at least one —SH-moiety, which provide for a disulfide bond linking the cationic or polycationic polymer with another component of the polymeric carrier as defined herein. Thus, likewise as defined herein, the polymeric carrier may comprise the same or different cationic or polycationic polymers.

In the specific case that the cationic component of the polymeric carrier comprises a (non-peptidic) cationic or polycationic polymer the cationic properties of the (non-peptidic) cationic or polycationic polymer may be determined upon its content of cationic charges when compared to the overall charges of the components of the cationic polymer. Preferably, the content of cationic charges in the cationic polymer at a (physiological) pH as defined herein is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 30% to 100%, even preferably in the range of about 50% to 100%, e.g. 50, 60, 70, 80%, 90% or 100%, or in a range formed by any two of the afore mentioned values, provided, that the content of all charges, e.g. positive and negative charges at a (physiological) pH as defined herein, in the entire cationic polymer is 100%.

Preferably, the (non-peptidic) cationic component of the polymeric carrier represents a cationic or polycationic polymer, typically exhibiting a molecular weight of about 0.1 or 0.5 kDa to about 100 kDa, preferably of about 1 kDa to about 75 kDa, more preferably of about 5 kDa to about 50 kDa, even more preferably of about 5 kDa to about 30 kDa, or a molecular weight of about 10 kDa to about 50 kDa, even more preferably of about 10 kDa to about 30 kDa. Additionally, the (non-peptidic) cationic or polycationic polymer typically exhibits at least one —SH-moiety, which is capable to form a disulfide linkage upon condensation with either other cationic components or other components of the polymeric carrier as defined herein.

In the above context, the (non-peptidic) cationic component of the polymeric carrier, which may be used to complex the at least one RNA of the inventive combination vaccine or any further nucleic acid comprised in the inventive combination vaccine may be selected from acrylates, modified acrylates, such as pDMAEMA (poly(dimethylaminoethyl methylacrylate)), chitosanes, aziridines or 2-ethyl-2-oxazoline (forming oligo ethylenimines or modified oligoethylenimines), polymers obtained by reaction of bisacrylates with amines forming oligo beta aminoesters or poly amido amines, or other polymers like polyesters, polycarbonates, etc. Each molecule of these (non-peptidic) cationic or polycationic polymers typically exhibits at least one —SH-moiety, wherein these at least one —SH-moiety may be introduced into the (non-peptidic) cationic or polycationic polymer by chemical modifications, e.g. using imonothiolan, 3-thio propionic acid or introduction of —SH-moieties containing amino acids, such as cysteine or any further (modified) amino acid. Such —SH-moieties are preferably as already defined above.

According to a particularly preferred embodiment, the further component, which may be contained in the polymeric carrier, and which may be used to complex the at least one RNA of the inventive combination vaccine or any further nucleic acid comprised in the inventive combination vaccine or which may be used to modify the different (short) cationic or polycationic peptides or (non-peptidic) polymers forming basis for the polymeric carrier or the biophysical/biochemical properties of the polymeric carrier as defined herein, is an amino acid component (AA). According to the present invention, the amino acid component (AA) comprises a number of amino acids preferably in a range of about 1 to 100, preferably in a range of about 1 to 50, more preferably selected from a number comprising 1, 2, 3, 4, 5, 6, 7, 8, 9, 10, 11, 12, 13, 14 or 15-20, or may be selected from a range formed by any two of the afore mentioned values. In this context the amino acids of amino acid component (AA) can be chosen independently from each other. For example if in the polymeric carrier two or more (AA) components are present they can be the same or can be different from each other.

The amino acid component (AA) may contain or may be flanked (e.g. terminally) by a —SH containing moiety, which allows introducing this component (AA) via a disulfide bond into the polymeric carrier as defined herein. In the specific case that the —SH containing moiety represents a cysteine, the amino acid component (AA) may also be read as -Cys-(AA)-Cys- wherein Cys represents cysteine and provides for the necessary —SH-moiety for a disulfide bond. The —SH containing moiety may be also introduced into amino acid component (AA) using any of modifications or reactions as shown above for the cationic component or any of its components.

Furthermore, the amino acid component (AA) may be provided with two —SH-moieties (or even more), e.g. in a form represented by formula HS-(AA)-SH to allow binding to two functionalities via disulfide bonds, e.g. if the amino acid component (AA) is used as a linker between two further components (e.g. as a linker between two cationic polymers).

Alternatively, the amino acid component (AA) may be provided with other functionalities as already described above for the other components of the polymeric carrier, which allow binding of the amino acid component (AA) to any of components of the polymeric carrier.

Thus, according to the present invention, the amino acid component (AA) of the polymeric carrier may be bound to further components of the polymeric carrier, which may be used to complex the at least one RNA of the inventive combination vaccine or any further nucleic acid comprised in the inventive combination vaccine with or without using a disulfide linkage.

According to a further and particularly preferred alternative, the amino acid component (AA), may be used to modify the polymeric carrier, particularly the content of cationic components in the polymeric carrier as defined above.

In the context of the present invention, the amino acid component (AA) may be selected from the following alternatives: an aromatic amino acid component, a hydrophilic (and preferably non charged polar) amino acid component, a lipophilic amino acid component, or a weak basic amino acid component.

According to a further alternative, the amino acid component (AA) may be a signal peptide or signal sequence, a localisation signal or sequence, a nuclear localisation signal or sequence (NLS), an antibody, a cell penetrating peptide (e.g. TAT), etc. Additionally, according to another alternative, the amino acid component (AA) may be a functional peptide or protein, which may modulate the functionality of the polymeric carrier accordingly. Such functional peptides or proteins as the amino acid component (AA) preferably comprise any peptides or proteins as defined herein, e.g. as defined below as therapeutically active proteins. According to one alternative, such further functional peptides or proteins may comprise so called cell penetrating peptides (CPPs) or cationic peptides for transportation.

According to a last alternative, the amino acid component (AA) may consist of any peptide or protein which can execute any favourable function in the cell. Particularly preferred are peptides or proteins selected from therapeutically active proteins or peptides, from antigens, e.g. tumour antigens, pathogenic antigens (animal antigens, viral antigens, protozoan antigens, bacterial antigens, allergic antigens), autoimmune antigens, or further antigens, from allergens, from antibodies, from immunostimulatory proteins or peptides, from antigen-specific T cell receptors, or from any other protein or peptide suitable for a specific (therapeutic) application. Particularly preferred are peptide epitopes from antigens, particularly of the virus family Paramyxoviridae and/or of the virus family Orthomyxoviridae as defined herein, and more particularly of the F protein of the virus family Paramyxoviridae and/or of the HA protein of the virus family Orthomyxoviridae as defined herein.

The polymeric carrier, which may be used to complex the at least one RNA of the inventive combination vaccine or any further nucleic acid comprised in inventive combination vaccine may comprise at least one of the above mentioned cationic or polycationic peptides, proteins or polymers or further components, e.g. (AA), wherein any of the above alternatives may be combined with each other, and may be formed by polymerizing same in a polymerization condensation reaction via their —SH-moieties.

Further, the polymeric carrier may be selected from a polymeric carrier molecule according to generic formula (V):

$$L\text{-}P^1\text{—S—}[\text{S—}P^2\text{—S}]_n\text{—S—}P^3\text{-}L \qquad \text{formula (V)}$$

wherein, $P^1$ and $P^3$ are different or identical to each other and represent a linear or branched hydrophilic polymer chain, each $P^1$ and $P^3$ exhibiting at least one —SH-moiety, capable to form a disulfide linkage upon condensation with component $P^2$, or alternatively with (AA), $(AA)_x$, or $[(AA)_x]_z$ if such components are used as a linker between $P^1$ and $P^2$ or $P^3$ and $P^2$) and/or with further components (e.g. (AA), $(AA)_x$, $[(AA)_x]_z$ or L), the linear or branched hydrophilic polymer chain selected independent from each other from polyethylene glycol (PEG), poly-N-(2-hydroxypropyl)methacrylamide, poly-2-(methacryloyloxy)ethyl phosphorylcholines, poly(hydroxyalkyl L-asparagine), poly(2-(methacryloyloxy)ethyl phosphorylcholine), hydroxyethylstarch or poly(hydroxyalkyl L-glutamine), wherein the hydrophilic polymer chain exhibits a molecular weight of about 1 kDa to about 100 kDa, preferably of about 2 kDa to about 25 kDa; or more preferably of about 2 kDa to about 10 kDa, e.g. about 5 kDa to about 25 kDa or 5 kDa to about 10 kDa;

$P^2$ is a cationic or polycationic peptide or protein, e.g. as defined above for the polymeric carrier formed by disulfide-crosslinked cationic components, and preferably having a length of about 3 to about 100 amino acids, more preferably having a length of about 3 to about 50 amino acids, even more preferably having a length of about 3 to about 25 amino acids, e.g. a length of about 3 to 10, 5 to 15, 10 to 20 or 15 to 25 amino acids, more preferably a length of about 5 to about 20 and even more preferably a length of about 10 to about 20; or is a cationic or polycationic polymer, e.g. as defined above for the polymeric carrier formed by disulfide-crosslinked cationic components, typically having a molecular weight of about 0.5 kDa to about 30 kDa, including a molecular weight of about 1 kDa to about 20 kDa, even more preferably of about 1.5 kDa to about 10 kDa, or having a molecular weight of about 0.5 kDa to about 100 kDa, including a molecular weight of about 10 kDa to about 50 kDa, even more preferably of about 10 kDa to about 30 kDa;

each $P^2$ exhibiting at least two —SH-moieties, capable to form a disulfide linkage upon condensation with further components $P^2$ or component(s) $P^1$ and/or $P^3$ or alternatively with further components (e.g. (AA), $(AA)_x$, or $[(AA)_x]_z$);

—S—S— is a (reversible) disulfide bond (the brackets are omitted for better readability), wherein S preferably represents sulphur or a —SH carrying moiety, which has formed a (reversible) disulfide bond. The (reversible) disulfide bond is preferably formed by condensation of —SH-moieties of either components $P^1$ and $P^2$, $P^2$ and $P^2$, or $P^2$ and $P^3$, or optionally of further components as defined herein (e.g. L, (AA), $(AA)_x$, $[(AA)_x]_z$, etc); The —SH-moiety may be part of the structure of these components or added by a modification as defined below;

L is an optional ligand, which may be present or not, and may be selected independent from the other from RGD, Transferrin, Folate, a signal peptide or signal sequence, a localization signal or sequence, a nuclear localization signal or sequence (NLS), an antibody, a cell penetrating peptide, (e.g. TAT or KALA), a ligand of a receptor (e.g. cytokines, hormones, growth factors etc), small molecules (e.g. carbohydrates like mannose or galactose or synthetic ligands), small molecule agonists, inhibitors or antagonists of receptors (e.g. RGD peptidomimetic analogues), or any further protein as defined herein, etc.;

n is an integer, typically selected from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 4 to 9, 4 to 10, 3 to 20, 4 to 20, 5 to 20, or 10 to 20, or a range of about 3 to 15, 4 to 15, 5 to 15, or 10 to 15, or a range of about 6 to 11 or 7 to 10. Most preferably, n is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

Each of hydrophilic polymers $P^1$ and $P^3$ typically exhibits at least one —SH-moiety, wherein the at least one —SH-moiety is capable to form a disulfide linkage upon reaction with component $P^2$ or with component (AA) or $(AA)_x$, if used as linker between $P^1$ and $P^2$ or $P^3$ and $P^2$ as defined below and optionally with a further component, e.g. L and/or (AA) or $(AA)_x$, e.g. if two or more —SH-moieties are contained. The following subformulae "$P^1$—S—S—$P^2$" and "$P^2$—S—S—$P^3$" within generic formula (V) above (the brackets are omitted for better readability), wherein any of S, $P^1$ and $P^3$ are as defined herein, typically represent a situation, wherein one —SH-moiety of hydrophilic polymers $P^1$ and $P^3$ was condensed with one —SH-moiety of component $P^2$ of generic formula (V) above, wherein both sulphurs of these —SH-moieties form a disulfide bond —S—S— as defined herein in formula (V). These —SH-moieties are typically provided by each of the hydrophilic polymers $P^1$ and $P^3$, e.g. via an internal cysteine or any further (modified) amino acid or compound which carries a —SH moiety. Accordingly, the subformulae "$P^1$—S—S—$P^2$" and "$P^2$—S—S—$P^3$" may also be written as "$P^1$-Cys-Cys-$P^2$" and "$P^2$-Cys-Cys-$P^3$", if the —SH-moiety is provided by a cysteine, wherein the term Cys-Cys represents two cysteines coupled via a disulfide bond, not via a peptide bond. In this case, the term "—S—S—" in these formulae may also be written as "—S-Cys", as "-Cys-S" or as "-Cys-Cys-". In this context, the term "-Cys-Cys-" does not represent a peptide bond but a linkage of two cysteines via their —SH-moieties to form a disulfide bond. Accordingly, the term "-Cys-Cys-" also may be understood generally as "-(Cys-S)—(S-Cys)-", wherein in this specific case S indicates the sulphur of the —SH-moiety of cysteine. Likewise, the terms "—S-Cys" and "—Cys-S" indicate a disulfide bond between a —SH containing moiety and a cysteine, which may also be written as "—S—(S-Cys)" and "-(Cys-S)—S". Alternatively, the hydrophilic polymers $P^1$ and $P^3$ may be modified with a —SH moiety, preferably via a chemical reaction with a compound carrying a —SH moiety, such that each of the hydrophilic polymers $P^1$ and $P^3$ carries at least one such —SH moiety. Such a compound carrying a —SH moiety may be e.g. an (additional) cysteine or any further (modified) amino acid, which carries a —SH moiety. Such a compound may also be any non-amino compound or moiety, which contains or allows to introduce a —SH moiety into hydrophilic polymers $P^1$ and $P^3$ as defined herein. Such non-amino compounds may be attached to the hydrophilic polymers $P^1$ and $P^3$ of formula (VI) of the polymeric carrier according to the present invention via chemical reactions or binding of compounds, e.g. by binding of a 3-thio propionic acid or thioimolane, by amide formation (e.g. carboxylic acids, sulphonic acids, amines, etc), by Michael addition (e.g maleimide moieties, □, □ unsaturated carbonyls, etc), by click chemistry (e.g. azides or alkines), by alkene/alkyne methathesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components. A particularly preferred PEG derivate in this context is alpha-Methoxy-omega-mercapto poly(ethylene glycol). In each case, the SH-moiety, e.g. of a cysteine or of any further (modified) amino acid or compound, may be present at the terminal ends or internally at any position of hydrophilic polymers $P^1$ and $P^3$. As defined herein, each of hydrophilic polymers $P^1$ and $P^3$ typically exhibits at least one —SH-moiety preferably at one terminal end, but may also contain two or even more —SH-moieties, which may be used to additionally attach further components as defined herein, preferably further functional peptides or proteins e.g. a ligand, an amino acid component (AA) or $(AA)_x$, antibodies, cell penetrating peptides or enhancer peptides (e.g. TAT, KALA), etc.

In the context of the entire formula (V) of the inventive polymeric carrier may be preferably defined as follows:

$$L-P^1-S-[Cys-P^2-Cys]_n-S-P^3-L \qquad \text{formula (VI)}$$

wherein L, $P^1$, $P^2$, $P^3$ and n are as defined herein, S is sulphur and each Cys provides for one —SH-moiety for the disulfide bond.

The amino acid component (AA) or $(AA)_x$ in the polymeric carrier of formula (V or VI), e.g. as defined above for the polymeric carrier formed by disulfide-crosslinked cationic components may also occur as a mixed repetitive amino acid component $[(AA)_x]_z$, wherein the number of amino acid components (AA) or $(AA)_x$ is further defined by integer z. In this context, z may be selected from a range of about 1 to 30, preferably from a range of about 1 to 15, more preferably 1 to 10 or 1 to 5 and even more preferably selected from a number selected from 1, 2, 3, 4, 5, 6, 7, 8, 9, 10, 11, 12, 13, 14 or 15, or may be selected from a range formed by any two of the afore mentioned values.

According to a specific and particularly preferred alternative, the amino acid component (AA) or $(AA)_x$, preferably written as $S-(AA)_x-S$ or $[S-(AA)_x-S]$ may be used to modify component $P^2$, particularly the content of component $S-P^2-S$ in repetitive component $[S-P^2-S]_n$ of the polymeric carrier of formula (V) above. This may be represented in the context of the entire polymeric carrier according to formula (VI) e.g. by following formula (VIa):

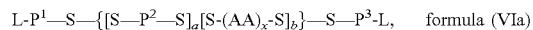

$$L-P^1-S-\{[S-P^2-S]_a[S-(AA)_x-S]_b\}-S-P^3-L, \qquad \text{formula (VIa)}$$

wherein x, S, L, AA, $P^1$, $P^2$ and $P^3$ are preferably as defined herein. In formula (VIa) above, any of the single components $[S-P^2-S]$ and $[S-(AA)_x-S]$ may occur in any order in the subformula $\{[S-P^2-S]_a[S-(AA)_x-S]_b\}$. The numbers of single components $[S-P^2-S]$ and $[S-(AA)_x-S]$ in the subformula $\{[S-P^2-S]_a[S-(AA)_x-S]_b\}$ are determined by integers a and b, wherein a+b=n. n is an integer and is defined as above for formula (V).

According to another embodiment, the polymeric carrier, which may be used to complex the at least one RNA of the combination vaccine or any further nucleic acid comprised in the combination vaccine or single components thereof, e.g. of the above mentioned cationic or polycationic peptides, proteins or polymers or further components, e.g. (AA), may be further modified with a ligand, preferably a carbohydrate, more preferably a sugar, even more preferably mannose.

According to one specific embodiment, the entire polymeric carrier may be formed by a polymerization condensation (of at least one) of the above mentioned cationic or polycationic peptides, proteins or polymers or further components, e.g. (AA), via their —SH-moieties in a first step and complexing the at least one RNA of the inventive combination vaccine or any further nucleic acid comprised in the inventive combination vaccine to such a polymeric carrier in a second step. The polymeric carrier may thus contain a number of at least one or even more of the same or different of the above defined cationic or polycationic peptides, proteins or polymers or further components, e.g. (AA), the number preferably determined by the above range.

According to one alternative specific embodiment, the polymeric carrier, which may be used to complex the at least one RNA of the inventive combination vaccine or any further nucleic acid comprised in the inventive combination vaccine is formed by carrying out the polymerization condensation of at least one of the above mentioned cationic or polycationic peptides, proteins or polymers or further components, e.g. (AA), via their —SH-moieties simultaneously to complexing the at least one RNA of the inventive combination vaccine or any further nucleic acid comprised in the inventive combination vaccine to the (in situ prepared) polymeric carrier. Likewise, the polymeric carrier may thus also here contain a number of at least one or even more of the same or different of the above defined cationic or polycationic peptides, proteins or polymers or further components, e.g. (AA), the number preferably determined by the above range.

In this context it is particularly preferred that the at least one RNA of the inventive combination vaccine or any further coding nucleic acid in the inventive combination vaccine is complexed at least partially with a cationic or polycationic compound and/or a polymeric carrier, preferably cationic proteins or peptides. Partially means that only a part of the at least one RNA is complexed with a cationic compound and that the rest of the at least one RNA is comprised in the combination vaccine in uncomplexed form ("free"). Preferably the ratio of complexed RNA to: free RNA in the combination vaccine is selected from a range. of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of complexed RNA to free RNA in the inventive combination vaccine is selected from a ratio of about 1:1 (w/w).

The complexed RNA in the inventive combination vaccine, is preferably prepared according to a first step by complexing the at least one RNA with a cationic or polycationic compound and/or with a polymeric carrier, preferably as defined herein, in a specific ratio to form a stable complex. In this context, it is highly preferable, that no free cationic or polycationic compound or polymeric carrier or only a negligibly small amount thereof remains in the component of the complexed RNA after complexing the RNA. Accordingly, the ratio of the RNA and the cationic or polycationic compound and/or the polymeric carrier in the component of the complexed RNA is typically selected in a range that the RNA is entirely complexed and no free cationic or polycationic compound or polymeric carrier or only a negligibly small amount thereof remains in the composition.

Preferably the ratio of the RNA (e.g. mRNA) to the cationic or polycationic compound and/or the polymeric carrier, preferably as defined herein, is selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w). Alternatively, the ratio of the RNA to the cationic or polycationic compound and/or the polymeric carrier, preferably as defined herein, in the component of the complexed RNA, may also be calculated on the basis of the nitrogen/phosphate ratio (N/P-ratio) of the entire complex. In the context of the present invention, an N/P-ratio is preferably in the range of about 0.1-10, preferably in a range of about 0.3-4 and most preferably in a range of about 0.5-2 or 0.7-2 regarding the ratio of RNA:cationic or polycationic compound and/or polymeric carrier, preferably as defined herein, in the complex, and most preferably in a range of about 0.7-1.5, 0.5-1 or 0.7-1, and even most preferably in a range of about 0.3-0.9 or 0.5-0.9, preferably provided that the cationic or polycationic compound in the complex is a cationic or polycationic cationic or polycationic protein or peptide and/or the polymeric carrier as defined above. In this specific embodiment the complexed RNA is also encompassed in the term "adjuvant component".

In another embodiment, the at least one antigen-providing RNA of the inventive combination vaccine as defined above may be formulated together with an adjuvant. Such an adjuvant may be preferably a further nucleic acid that is not encoding a further antigen but is able to stimulate an unspecific immune response, i.e. innate immune response, by interacting with any part of the innate immune system. Such a nucleic acid stimulating an unspecific immune response is termed herein as "adjuvant nucleic acid".

In this context an adjuvant nucleic acid preferably comprises or consists of an oligo- or a polynucleotide; more preferably an adjuvant nucleic acid comprises or consists of a RNA or a DNA; even more preferably such an adjuvant nucleic acid comprising or consisting of a RNA or a DNA being complexed with a cationic or polycationic compound and/or with a polymeric carrier; optionally in a weight ratio selected from a range of about 6:1 (w/w) to about 0.25:1 (w/w), more preferably from about 5:1 (w/w) to about 0.5:1 (w/w), even more preferably of about 4:1 (w/w) to about 1:1 (w:w) or of about 3:1 (w/w) to about 1:1 (w/w), and most preferably a ration of about 3:1 (w/w) to about 2:1 (w/w) of adjuvant component to cationic or polycationic compound and/or with a polymeric carrier; or optionally in a nitrogen/phosphate ratio of the adjuvant component to cationic or polycationic compound and/or polymeric carrier in the range of about 0.1-10, preferably in a range of about 0.3-4, most preferably in a range of about 0.7-1 or 0.5-1, and even most preferably in a range of about 0.3-0.9 or 0.5-0.9. Such a complexed adjuvant nucleic acid is also encompassed in the term "adjuvant component":

In other words a combination vaccine according to the invention may comprise a first RNA encoding for an antigenic function, e.g. the RSV Fusion (F) protein, the Influenza Hemagglutinin (HA) protein or the like, and a second nucleic acid that is acting as an adjuvant which is called the adjuvant nucleic acid. Of course the inventive combination vaccine may also comprise further RNAs encoding for further antigenic functions and is also not limited to comprise only one adjuvant nucleic acid but can comprise several different of them. Both kinds of nucleic acid, the antigen-encoding RNA and the adjuvant nucleic acid, may be, independently from each other, complexed with a carrier as defined above. Therefore, a cationic or polycationic compound and/or a polymeric carrier used to complex the at least one adjuvant nucleic acid, may be selected from a cationic or polycationic compound and/or a polymeric carrier as defined above.

In this context, an adjuvant nucleic acid, as used herein, is preferably selected from nucleic acids which are known to bind to TLR receptors. Such an adjuvant nucleic acid can be in the form of a(n) (immunostimulatory) CpG nucleic acid, in particular CpG-RNA or CpG-DNA, which preferably induces an innate immune response. A CpG-RNA or CpG-DNA used according to the invention can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid used according to the invention is preferably in the form of CpG-RNA, more preferably in the form of single-stranded CpG-RNA (ss CpG-RNA). Also preferably, such CpG nucleic acids have a length as described above. Preferably, the CpG motifs are unmethylated.

Furthermore, an adjuvant nucleic acid, as used herein, can be an immunostimulatory RNA (isRNA), which preferably elicits an innate immune response. Preferably, the immunostimulatory RNA may be a single-stranded, a double-stranded or a partially double-stranded RNA, more preferably a single-stranded RNA, and/or a circular or linear RNA, more preferably a linear RNA. More preferably, the immunostimulatory RNA may be a (linear) single-stranded RNA. Even more preferably, the immunostimulatory RNA may be a (long) (linear) (single-stranded) non-coding RNA. In this context it is particular preferred that the isRNA carries a triphosphate at its 5'-end which is the case for in vitro transcribed RNA. An immunostimulatory RNA may also occur as a short RNA oligonucleotide as defined herein. An immunostimulatory RNA as used herein may furthermore be selected from any class of RNA molecules, found in nature or being prepared synthetically, and which can induce an innate immune response and may support an adaptive immune response induced by an antigen.

In case the inventive combination vaccine comprises an antigen-providing RNA and additionally an adjuvant nucleic acid, the immune response that is evoked by administration of such a vaccine comprises activation of both parts of the immune system, the adaptive immune system as well as the innate immune system.

A substantial factor for a suitable adaptive immune response is the stimulation of different T cell sub-populations. T-lymphocytes are typically divided into two sub-populations, the T-helper 1 cells, in the following Th1-cells, and the T-helper 2 cells, in the following Th2-cells, with which the immune system is capable of destroying intracellular and extracellular pathogens (e.g. antigens). Thereby Th1-cells are responsible for intracellular pathogen destruction by assisting the cellular immune response by activation of macrophages and cytotoxic T cells. Th2-cells, on the other hand, are mainly for extracellular pathogen-elimination and promote the humoral immune response by stimulation of B-cells for conversion into plasma cells and by formation of antibodies (e.g. against antigens). The two T-helper cell populations differ in the pattern of the effector proteins (cytokines) produced by them.

The Th1-cell/Th2-cell ratio is of great importance in the induction and maintenance of an adaptive immune response. In connection with the present invention, the Th1-cell/Th2-cell ratio of the (adaptive) immune response is preferably shifted in the direction towards the cellular response (Th1 response) and a cellular immune response is thereby induced. Stimulation of this response of the adaptive immune system is mainly provoked by the translation of the antigen-providing RNA and the resulting presence of the peptide or protein antigens within the organism.

The innate immune system which may support such an adaptive immune response may be activated by ligands of Toll-like receptors (TLRs). TLRs are a family of highly conserved pattern recognition receptor (PRR) polypeptides that recognize pathogen-associated molecular patterns (PAMPs) and play a critical role in innate immunity in mammals. Currently at least thirteen family members, designated TLR1-TLR13 (Toll-like receptors: TLR1, TLR2, TLR3, TLR4, TLR5, TLR6, TLR7, TLR8, TLR9, TLR10, TLR11, TLR12 or TLR13), have been identified. Furthermore, a number of specific TLR ligands have been identified. It was e.g. found that unmethylated bacterial DNA and synthetic analogs thereof (CpG DNA) are ligands for TLR9 (Hemmi H et al. (2000) Nature 408:740-5; Bauer S et al. (2001) Proc Natl. Acad. Sci. USA 98, 9237-42). Furthermore, it has been reported that ligands for certain TLRs include certain nucleic acid molecules and that certain types of RNA are immunostimulatory in a sequence-independent or sequence-dependent manner, wherein these various immunostimulatory RNAs may e.g. stimulate TLR3, TLR7, or TLR8, or intracellular receptors such as RIG-I, MDA-5, etc.

In the context of the invention, the activation of the innate immune system can be provided by the adjuvant of the inventive combination vaccine. Preferably, an adjuvant nucleic acid, preferably an immunostimulatory RNA (isRNA), as used herein, may comprise any RNA sequence known to be immunostimulatory, including, e.g., RNA sequences representing and/or encoding ligands of TLRs, preferably selected from human family members TLR1-TLR10 or murine family members TLR1-TLR13, more preferably selected from (human) family members TLR1-TLR10, even more preferably from TLR7 and TLR8, ligands for intracellular receptors for RNA (such as RIG-I or MDA-5, etc.) (see e.g. Meylan, E., Tschopp, J. (2006). Toll-like receptors and RNA helicases: two parallel ways to trigger antiviral responses. Mol. Cell 22, 561-569), or any other immunostimulatory RNA sequence. Furthermore, (classes of) immunostimulatory RNA molecules, used as a further compound of the inventive combination vaccine, may include any other RNA capable of eliciting an innate immune response. E.g., such an immunostimulatory RNA may include ribosomal RNA (rRNA), transfer RNA (tRNA), messenger RNA (mRNA), and viral RNA (vRNA). Such an immunostimulatory RNA may comprise a length of 1000 to 5000, of 500 to 5000, of 5 to 5000, or of 5 to 1000, 5 to 500, 5 to 250, of 5 to 100, of 5 to 50 or of 5 to 30 nucleotides.

According to a particularly preferred embodiment, an adjuvant nucleic acid sequence, particularly an isRNA, as used herein, may consist of or comprise a nucleic acid of formula (VII) or (VIII):

$$G_l X_m G_n, \qquad \text{(formula (VII))}$$

wherein:

G is guanosine, uracil or an analogue of guanosine or uracil;

X is guanosine, uracil, adenosine, thymidine, cytosine or an analogue of the above-mentioned nucleotides;

l is an integer from 1 to 40, wherein when l=1 G is guanosine or an analogue thereof, when l>1 at least 50% of the nucleotides are guanosine or an analogue thereof;

m is an integer and is at least 3;

wherein when m=3 X is uracil or an analogue thereof, when m>3 at least 3 successive uracils or analogues of uracil occur;

n is an integer from 1 to 40, wherein when n=1 G is guanosine or an analogue thereof, when n>1 at least 50% of the nucleotides are guanosine or an analogue thereof.

$$C_l X_m C_n, \qquad \text{(formula (VIII))}$$

wherein:
C is cytosine, uracil or an analogue of cytosine or uracil;
X is guanosine, uracil, adenosine, thymidine, cytosine or an analogue of the above-mentioned nucleotides;
l is an integer from 1 to 40,
   wherein
   when l=1 C is cytosine or an analogue thereof,
   when l>1 at least 50% of the nucleotides are cytosine or an analogue thereof;
m is an integer and is at least 3;
   wherein
   when m=3 X is uracil or an analogue thereof,
   when m>3 at least 3 successive uracils or analogues of uracil occur;
n is an integer from 1 to 40,
   wherein
   when n=1 C is cytosine or an analogue thereof,
   when n>1 at least 50% of the nucleotides are cytosine or an analogue thereof.

The nucleic acids of formula (VII) or (VIII), which may be used as an adjuvant nucleic acid sequence, particularly an isRNA, may be relatively short nucleic acid molecules with a typical length of approximately from 5 to 100 (but may also be longer than 100 nucleotides for specific embodiments, e.g. up to 200 nucleotides), from 5 to 90 or from 5 to 80 nucleotides, preferably a length of approximately from 5 to 70, more preferably a length of approximately from 8 to 60 and, more preferably a length of approximately from 15 to 60 nucleotides, more preferably from 20 to 60, most preferably from 30 to 60 nucleotides. If the nucleic acid of formula (VII) or (VIII) has a maximum length of e.g. 100 nucleotides, m will typically be <=98. The number of nucleotides G in the nucleic acid of formula (I) is determined by l or n. l and n, independently of one another, are each an integer from 1 to 40, wherein when l or n=1 G is guanosine or an analogue thereof, and when l or n>1 at least 50% of the nucleotides are guanosine or an analogue thereof. For example, without implying any limitation, when l or n=4 $G_l$ or $G_n$ can be, for example, a GUGU, GGUU, UGUG, UUGG, GUUG, GGGU, GGUG, GUGG, UGGG or GGGG, etc.; when l or n=5 $G_l$ or $G_n$ can be, for example, a GGGUU, GGUGU, GUGGU, UGGGU, UGGUG, UGUGG, UUGGG, GUGUG, GGGGU, GGGUG, GUGGG, GUGGG, UGGGG, or GGGGG, etc.; etc. A nucleotide adjacent to $X_m$ in the nucleic acid of formula (VII) according to the invention is preferably not a uracil. Similarly, the number of nucleotides C in the nucleic acid of formula (VIII) according to the invention is determined by l or n. l and n, independently of one another, are each an integer from 1 to 40, wherein when l or n=1 C is cytosine or an analogue thereof, and when l or n>1 at least 50% of the nucleotides are cytosine or an analogue thereof. For example, without implying any limitation, when l or n=4, $C_l$ or $C_n$ can be, for example, a CUCU, CCUU, UCUC, UUCC, CUUC, CCCU, CCUC, CUCC, UCCC or CCCC, etc.; when l or n=5 $C_l$ or $C_n$ can be, for example, a CCCUU, CCUCU, CUCCU, UCCCU, UCCUC, UCUCC, UUCCC, CUCUC, CCCCU, CCCUC, CCUCC, CUCCC, UCCCC, or CCCCC, etc.; etc. A nucleotide adjacent to $X_m$ in the nucleic acid of formula (VIII) according to the invention is preferably not a uracil. Preferably, for formula (VII), when l or n>1, at least 60%, 70%, 80%, 90% or even 100% of the nucleotides are guanosine or an analogue thereof, as defined above. The remaining nucleotides to 100% (when guanosine constitutes less than 100% of the nucleotides) in the flanking sequences $G_l$ and/or $G_n$ are uracil or an analogue thereof, as defined hereinbefore. Also preferably, l and n, independently of one another, are each an integer from 2 to 30, more preferably an integer from 2 to 20 and yet more preferably an integer from 2 to 15. The lower limit of l or n can be varied if necessary and is at least 1, preferably at least 2, more preferably at least 3, 4, 5, 6, 7, 8, 9 or 10. This definition applies correspondingly to formula (VIII).

According to a further particularly preferred embodiment, an immunostimulatory nucleic acid sequence, particularly an isRNA, as used herein, may consist of or comprise a nucleic acid of formula (IX) or (X):

  (formula (IX))

wherein:
G is guanosine (guanine), uridine (uracil) or an analogue of guanosine (guanine) or uridine (uracil), preferably guanosine (guanine) or an analogue thereof;
X is guanosine (guanine), uridine (uracil), adenosine (adenine), thymidine (thymine), cytidine (cytosine), or an analogue of these nucleotides (nucleosides), preferably uridine (uracil) or an analogue thereof;
N is a nucleic acid sequence having a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);
a is an integer from 1 to 20, preferably from 1 to 15, most preferably from 1 to 10;
l is an integer from 1 to 40,
   wherein
   when l=1, G is guanosine (guanine) or an analogue thereof,
   when l>1, at least 50% of these nucleotides (nucleosides) are guanosine (guanine) or an analogue thereof;
m is an integer and is at least 3;
   wherein
   when m=3, X is uridine (uracil) or an analogue thereof, and
   when m>3, at least 3 successive uridines (uracils) or analogues of uridine (uracil) occur;
n is an integer from 1 to 40,
   wherein
   when n=1, G is guanosine (guanine) or an analogue thereof,
   when n>1, at least 50% of these nucleotides (nucleosides) are guanosine (guanine) or an analogue thereof;
u, v may be independently from each other an integer from 0 to 50,
   preferably wherein when u=0, v≥1, or
   when v=0, u≥1;
wherein the nucleic acid molecule of formula (IX) has a length of at least 50 nucleotides, preferably of at least 100 nucleotides, more preferably of at least 150 nucleotides, even more preferably of at least 200 nucleotides and most preferably of at least 250 nucleotides.

  (formula (X))

wherein:
C is cytidine (cytosine), uridine (uracil) or an analogue of cytidine (cytosine) or uridine (uracil), preferably cytidine (cytosine) or an analogue thereof;
X is guanosine (guanine), uridine (uracil), adenosine (adenine), thymidine (thymine), cytidine (cytosine) or an analogue of the above-mentioned nucleotides (nucleosides), preferably uridine (uracil) or an analogue thereof;

N is each a nucleic acid sequence having independent from each other a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);

a is an integer from 1 to 20, preferably from 1 to 15, most preferably from 1 to 10;

l is an integer from 1 to 40,
wherein
when l=1, C is cytidine (cytosine) or an analogue thereof,
when l>1, at least 50% of these nucleotides (nucleosides) are cytidine (cytosine) or an analogue thereof;

m is an integer and is at least 3;
wherein
when m=3, X is uridine (uracil) or an analogue thereof,
when m>3, at least 3 successive uridines (uracils) or analogues of uridine (uracil) occur;

n is an integer from 1 to 40,
wherein
when n=1, C is cytidine (cytosine) or an analogue thereof,
when n>1, at least 50% of these nucleotides (nucleosides) are cytidine (cytosine) or an analogue thereof.

u, v may be independently from each other an integer from 0 to 50,
preferably wherein when u=0, v 1, or
when v=0, u 1;

wherein the nucleic acid molecule of formula (X) according to the invention has a length of at least 50 nucleotides, preferably of at least 100 nucleotides, more preferably of at least 150 nucleotides, even more preferably of at least 200 nucleotides and most preferably of at least 250 nucleotides.

Any of the definitions given above in formulae (VII) and (VIII), e.g. for elements N (i.e. $N_u$ and $N_v$) and X ($X_m$), particularly the core structure as defined above, as well as for integers a, l, m, n, u and v, similarly apply to elements of formula (IX) and (X) correspondingly. The definition of bordering elements $N_u$ and $N_v$ in formula (X) is identical to the definitions given above for $N_u$ and $N_v$ in formula (IX).

Finally, the adjuvant, which may be used together with the antigen-providing RNA in the inventive combination vaccine, is preferably prepared according to a first step by complexing the immunostimulatory RNA (isRNA) with a cationic or polycationic compound and/or with a polymeric carrier, preferably as defined herein, in a specific ratio to form a stable complex. In this context, it is highly preferable, that no free cationic or polycationic compound or polymeric carrier or only a negligibly small amount thereof remains in the adjuvant after complexing the isRNA. Accordingly, the ratio of the isRNA and the cationic or polycationic compound and/or the polymeric carrier in the adjuvant is typically selected in a range that the isRNA is entirely complexed and no free cationic or polycationic compound or polymeric carrier or only a negligibly small amount thereof remains in the composition.

Preferably the ratio of the adjuvant, i.e. the ratio of the isRNA to the cationic or polycationic compound and/or the polymeric carrier, preferably as defined herein, is selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w). Alternatively, the ratio of the isRNA to the cationic or polycationic compound and/or the polymeric carrier, preferably as defined herein, in the adjuvant, may also be calculated on the basis of the nitrogen/phosphate ratio (N/P-ratio) of the entire complex of the adjuvant. In the context of the present invention, an N/P-ratio is preferably in the range of about 0.1-10, preferably in a range of about 0.3-4 and most preferably in a range of about 0.5-2 or 0.7-2 regarding the ratio of isRNA:cationic or polycationic compound and/or polymeric carrier, preferably as defined herein, in the complex, and most preferably in a range of about 0.7-1.5, 0.7-1 or 0.5-1, and even most preferably in a range of about 0.3-0.9 or 0.5-0.9, preferably provided the cationic or polycationic compound in the complex is a cationic or polycationic cationic or polycationic protein or peptide and/or the polymeric carrier is as defined above.

According to the above, in a further preferred embodiment of the invention, the inventive combination vaccine is formulated to comprise a) said at least one RNA; preferably in form of a mono-, bi- or multicistronic RNA, optionally being stabilized, optionally being optimized for translation and/or optionally being complexed with a cationic or polycationic compound or a polymeric carrier;

b) optionally an adjuvant component, comprising or consisting of said at least one RNA and/or at least one adjuvant nucleic acid, complexed with a cationic or polycationic compound and/or with a polymeric carrier, and c) optionally a pharmaceutically acceptable carrier.

In this context it is particularly preferred that the optionally comprised adjuvant component comprises the same RNA as comprised in the inventive combination vaccine as antigen-providing RNA e.g. mRNA coding for a F protein of viruses of the Paramyxoviridae or fragments, variants or derivatives thereof, or coding for a HA protein of viruses of the Orthomyxoviridae or fragments, variants or derivatives thereof.

Despite, the inventive combination vaccine may comprise further components for facilitating administration and uptake of the vaccine. Such further components may be an appropriate carrier or vehicle, additional adjuvants for supporting any immune response, antibacterial and/or antiviral agents.

Accordingly, in a further embodiment, the inventive combination vaccine furthermore comprises a pharmaceutically acceptable carrier and/or vehicle.

Such a pharmaceutically acceptable carrier typically includes the liquid or non-liquid basis of a composition comprising the components of the combination vaccine. If the composition is provided in liquid form, the carrier will typically be pyrogen-free water; isotonic saline or buffered (aqueous) solutions, e.g. phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds, which are suitable for administration to a patient to be treated, may be used as well for the vaccine according to the invention. The term "compatible" as used here means that these constituents of the combination vaccine are capable of being mixed with the components of the combination vaccine in such a manner that no interaction occurs which would substantially reduce the pharmaceutical effectiveness of the combination vaccine under typical use conditions.

Furthermore, the inventive combination vaccine may comprise one or more additional adjuvants which are suitable to initiate or increase an immune response of the innate immune system, i.e. a non-specific immune response, particularly by binding to pathogen-associated molecular patterns (PAMPs). With other words, when administered, the vaccine preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following. According to one embodiment such an adjuvant may be selected from an adjuvant as defined above.

Also such an adjuvant may be selected from any adjuvant known to a skilled person and suitable for the present case, i.e. supporting the induction of an innate immune response in a mammal and/or suitable for depot and delivery of the components of the combination vaccine. Preferred as adjuvants suitable for depot and delivery are cationic or polycationic compounds as defined above. Likewise, the adjuvant may be selected from the group consisting of, e.g., cationic or polycationic compounds as defined above, from chitosan, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylaminob-D-glucopyranosyl)-N-octadecyl-dodecanoyl-amide hydroacetate); CALCITRIOL™ (1-alpha,25-dihydroxy-vitamin D3); calcium phosphate gel; CAP™ (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D35 glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L47 alanyl-D-isoglutamine); imiquimod (1-(2-methypropyl)-1H-imidazo[4,5-c]quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferongamma; interleukin-1beta; interleukin-2; interleukin-7; interleukin-12; ISCOMSTM; ISCOPREP 7.0.3. TM; liposomes; LOXORIBINE™ (7-allyl-8-oxoguanosine); LT 5 oral adjuvant (*E. coli* labile enterotoxin-protoxin); microspheres and microparticles of any composition; MF59™; (squalenewater emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-Gln-OCH3); MURAPALMITINE™ and DMURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ ((β□-glucan); PLGA, PGA and PLA (homo- and co-polymers of lactic acid and glycolic acid; microspheres/nanospheres); PLURONIC L121™; PMMA (polymethylmethacrylate); PODDSTM (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, AL); STIMULON™ (QS-21); Quil-A (Quil-A saponin); S-28463 (4-amino-otec-dimethyl-2-ethoxymethyl-1H-imidazo[4,5-c]quinoline-1-ethanol); SAF-1™ ("Syntex adjuvant formulation"); Sendai proteoliposomes and Sendai containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-L-Aladipalmitoxypropylamide); Theronyl-MDP (Termurtide™ or [thr 1]-MDP; N-acetylmuramyl-Lthreonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin, microbe derived adjuvants, including Romurtide, DETOX, MPL, CWS, Mannose, CpG nucleic acid sequences, CpG7909, ligands of human TLR 1-10, ligands of murine TLR 1-13, ISS-1018, 35 IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

Particularly preferred, an adjuvant may be selected from adjuvants, which support induction of a Th1-immune response or maturation of naïve T-cells, such as GM-CSF, IL-12, IFNg, any immunostimulatory nucleic acid as defined above, preferably an immunostimulatory RNA, CpG DNA, etc.

In a further preferred embodiment it is also possible that the inventive combination vaccine contains besides the antigen-providing RNA further components which are selected from the group comprising: further antigens or further antigen-providing nucleic acids; a further immunotherapeutic agent; one or more auxiliary substances; or any further compound, which is known to be immunostimulating due to its binding affinity (as ligands) to human Toll-like receptors; and/or an adjuvant nucleic acid, preferably an immunostimulatory RNA (isRNA).

A further component of the inventive combination vaccine may be an immunotherapeutic agent that can be selected from immunoglobulins, preferably IgGs, monoclonal or polyclonal antibodies, polyclonal serum or sera, etc, most preferably immunoglobulins directed against a virus of the Paramyxoviridae family e.g. palivizumab. Preferably, such a further immunotherapeutic agent may be provided as a peptide/protein or may be encoded by a nucleic acid, preferably by a DNA or an RNA, more preferably an mRNA. Such an immunotherapeutic agent allows providing passive vaccination additional to active vaccination triggered by the RNA encoded antigens of the inventive combination vaccine.

The inventive combination vaccine can additionally contain one or more auxiliary substances in order to increase its immunogenicity or immunostimulatory capacity, if desired. A synergistic action of the components of the inventive combination vaccine and of an auxiliary substance, which may be optionally contained in the vaccine, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CSF, which allow an immune response to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta or TNF-alpha, growth factors, such as hGH.

The inventive combination vaccine can also additionally contain any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13, a ligand of a NOD-like receptor, or a ligand of a RIG-I like receptor. In this context the inventive combination vaccine may also additionally contain an adjuvant nucleic acid, preferably an immunostimulatory RNA (isRNA), as defined above.

Accordingly, in another preferred embodiment, the inventive combination vaccine furthermore comprises at least one adjuvant, an auxiliary substance selected from lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (isRNA), a CpG-DNA, an antibacterial agent, or an anti-viral agent.

In this context, antigens additionally included in the inventive combination vaccine are typically substances such as cells, proteins, peptides, nucleic acids or other bio- or macromolecules or fragments thereof. More preferably, antigens may be proteins and peptides or fragments thereof, such as epitopes of those proteins or peptides, preferably having 5 to 15, more preferably 6 to 9, amino acids. Particularly, said proteins, peptides or epitopes may be derived from Hemagglutinin (HA)-proteins of viruses of the Orthomyxoviridae or may be derived from Fusion (F) proteins of viruses of the Paramyxoviridae. Further, antigens may also comprise any other biomolecule, e.g., lipids, carbohydrates, etc. Preferably, the antigen is a protein or (poly-) peptide antigen, a nucleic acid, a nucleic acid encoding a protein or (poly-) peptide antigen, a polysaccharide antigen, a polysaccharide conjugate antigen, a lipid antigen, a glycolipid antigen, a carbohydrate antigen, a bacterium, a cell (vaccine), or killed or attenuated viruses or bacteria. Particularly preferred in this context is the addition of antigens of the virus family Paramyxoviridae, particularly the addition of antigens comprising or coding for full-length or fragments, variants or derivatives of: F—fusion protein, N—nucleocapsid protein, P—phosphoprotein, M—matrix protein, SH—small hyrdophobic protein, G—glycoprotein, NS1—non-structural protein 1, NS2—non-structural protein 2, M2-1— elongation factor, M2-2— transcription regulation and/or L—large protein, or the addition of antigens of the virus family Orthomyxoviridae, particularly the addition of antigens comprising or coding for full-length or fragments, variants or derivatives of: HA—Hemagglutinin, NA—Neuraminidase, NP—Nucleoprotein, M1—matrix protein 1, M2—matrix protein 2, NEP— nuclear export protein, PA—polymerase acidic protein, PB1—polymerase basic protein 1, PB2—polymerase basic protein 2, NS1—non-structural protein 1, NS2—non-structural protein 2 and/or NS3—non-structural protein 3.

The combination vaccine as defined according to the present invention may furthermore comprise further additives or additional compounds. Further additives which may be included in the combination vaccine are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives, RNase inhibitors and/or an anti-bacterial agent or an anti-viral agent.

In this context, any anti-bacterial agents known to one of skill in the art may be used in combination with the components of the inventive combination vaccine as defined herein. Non-limiting examples of anti-bacterial agents include Amikacin, Amoxicillin, Amoxicillin-clavulanic acid, Amphothericin-B, Ampicillin, Ampicllin-sulbactam, Apramycin, Azithromycin, Aztreonam, Bacitracin, Benzylpenicillin, Caspofungin, Cefaclor, Cefadroxil, Cefalexin, Cefalothin, Cefazolin, Cefdinir, Cefepime, Cefixime, Cefmenoxime, Cefoperazone, Cefoperazone-sulbactam, Cefotaxime, Cefoxitin, Cefbirome, Cefpodoxime, Cefpodoxime-clavulanic acid, Cefpodoxime-sulbactam, Cefbrozil, Cefquinome, Ceftazidime, Ceftibutin, Ceftiofur, Ceftobiprole, Ceftriaxon, Cefuroxime, Chloramphenicole, Florfenicole, Ciprofloxacin, Clarithromycin, Clinafloxacin, Clindamycin, Cloxacillin, Colistin, Cotrimoxazol (Trimthoprim/sulphamethoxazole), Dalbavancin, Dalfopristin/Quinopristin, Daptomycin, Dibekacin, Dicloxacillin, Doripenem, Doxycycline, Enrofloxacin, Ertapenem, Erythromycin, Flucloxacillin, Fluconazol, Flucytosin, Fosfomycin, Fusidic acid, Garenoxacin, Gatifloxacin, Gemifloxacin, Gentamicin, Imipenem, Itraconazole, Kanamycin, Ketoconazole, Levofloxacin, Lincomycin, Linezolid, Loracarbef, Mecillnam (amdinocillin), Meropenem, Metronidazole, Meziocillin, Mezlocillin-sulbactam, Minocycline, Moxifloxacin, Mupirocin, Nalidixic acid, Neomycin, Netilmicin, Nitrofurantoin, Norfloxacin, Ofloxacin, Oxacillin, Pefloxacin, Penicillin V, Piperacillin, Piperacillin-sulbactam, Piperacillin-tazobactam, Rifampicin, Roxythromycin, Sparfloxacin, Spectinomycin, Spiramycin, Streptomycin, Sulbactam, Sulfamethoxazole, Teicoplanin, Telavancin, Telithromycin, Temocillin, Tetracyklin, Ticarcillin, Ticarcillin-clavulanic acid, Tigecycline, Tobramycin, Trimethoprim, Trovafloxacin, Tylosin, Vancomycin, Virginiamycin, and Voriconazole.

Anti-viral agents are preferably, e.g., nucleoside analogs (e.g., zidovudine, acyclovir, gancyclovir, vidarabine, idoxuridine, trifluridine, and ribavirin), foscarnet, amantadine, peramivir, rimantadine, saquinavir, indinavir, ritonavir, alpha-interferons and other interferons, AZT, t-705, zanamivir (Relenza®), and oseltamivir (Tamiflu®). Other anti-viral agents include influenza virus vaccines, e.g., Fluarix® (Glaxo SmithKline), FluMist® (MedImmune Vaccines), Fluvirin® (Chiron Corporation), Flulaval® (GlaxoSmithKline), Afluria® (CSL Biotherapies Inc.), Agriflu® (Novartis) or Fluzone® (Aventis Pasteur).

The inventive combination vaccine typically comprises a "safe and effective amount" of the components of the inventive combination vaccine as defined herein. As used herein, a "safe and effective amount" preferably means an amount of the components, preferably of the at least one RNA encoding at least one F protein or a part thereof of the virus family Paramyxoviridae, and at least one HA protein or a part thereof of the virus family Orthomyxoviridae, that is sufficient to significantly induce a positive modification or prevention of a disease or disorder as defined herein. At the same time, however, a "safe and effective amount" is small enough to avoid serious side-effects and to permit a sensible relationship between advantage and risk. The determination of these limits typically lies within the scope of sensible medical judgment.

In a further aspect, the invention provides a combination vaccine for use in a method of prophylactic and/or therapeutic treatment of infections caused by viruses of the virus family Paramyxoviridae and/or of the virus family Orthomyxoviridae, particularly respiratory tract infections; preferably RSV infection, mumps, measles, bronchitis, pneumonia, croup, distemper or rinderpest, and influenza. Consequently, in a further aspect, the present invention is directed to the first medical use of the inventive combination vaccine as defined herein as a medicament. Particularly, the invention provides the use of a combination vaccine as defined above for the preparation of a medicament. According to another aspect, the present invention is directed to the second medical use of the combination vaccine, as defined herein, optionally in form of a kit or kit of parts, for the treatment of diseases as defined herein. Particularly, the combination vaccine to be used in a method as said above is a combination vaccine formulated together with a pharmaceutically acceptable vehicle and an optionally additional adjuvant and an optionally additional further component as defined above e.g. a further antigen. The combination vaccine may alternatively be provided such that it is administered for treating diseases as disclosed herein by two doses, each dose containing distinct RNA species, e.g. the first dose containing at least one RNA encoding the F protein (or fragments deivatives or variants thereof) and the second dose containing at least one RNA encoding the HA protein (or fragments deivatives or variants thereof). By that embodiment, both doses are administered in a staggered way, i.e. subsequently, shortly one after the other, e.g. within less than 10 minutes, preferably less than 2 minutes, and at the same site of the body to achieve the same immunological effect as for administration of one single composition containing both, e.g. the RNA encoding the HA protein and the RNA encoding the F protein.

In a preferred embodiment, the method comprises the in vitro transfection of isolated cells. The cells used therefore are preferably human or animal cells, particularly cells of a primary cell culture, which are then retransferred to a human or animal. Prior to transfection, these cells are typically isolated from the patient to be treated and cultivated.

In a further embodiment, it is preferred that the combination vaccine comprises one or more RNAs encoding for the Fusion (F) protein or a fragment, variant or derivative of the Fusion (F) protein derived from the virus family Paramyxoviridae and for the Hemagglutinin (HA) protein or a fragment, variant or derivative of the Hemagglutinin (HA) protein derived from the virus family Orthomyxoviridae to be administered to an individual. In such a method, both antigenic functions of the combination vaccine are provided by one composition and can be administered to an individual e.g. by one single injection, preferably by parental administration.

Alternatively, of course administration can also occur orally, nasally, pulmonary, by inhalation, topically, rectally, buccally, vaginally, or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

According to a specific embodiment, the combination vaccine may be administered to the patient as a single dose. In certain embodiments, the inventive combination vaccine may be administered to a patient as a single dose followed by a second dose later and optionally even a third, fourth (or more) dose subsequent thereto etc. In accordance with this embodiment, booster inoculations with the inventive combination vaccine may be administered to a patient at specific time intervals, preferably as defined below, following the second (or third, fourth, etc.) inoculation. In certain embodiments, such booster inoculations with the inventive combination vaccine may utilize an additional compound or component as defined for the inventive combination vaccine as defined herein.

The inventive combination vaccine, as defined herein, may be used for human and also for veterinary medical purposes, preferably for human medical purposes. More preferably, the inventive combination vaccine may be used for treating a mammal for diseases as mentioned herein. In the context of the present invention, a mammal may be selected from any mammal, preferably from a mammal, selected from the group comprising, e.g., goat, cattle, swine, dog, cat, donkey, monkey, ape, a rodent such as a mouse, hamster, rabbit, and, in particular, human. Administration modes may be as defined herein.

Preferably, the method comprises the in vitro transfection of isolated cells. Particularly, a method of treating an individual with his own cells can be performed advantageously by transfection of isolated cells with the inventive combination vaccine. The cells used therefore are preferably human or animal cells, particularly cells of a primary cell culture, which are then retransferred to a human or animal. Prior to transfection, these cells are typically isolated from the patient to be treated and cultivated. The inventive combination vaccine may be administered to the primary cell culture without further adjuvants or vehicles contained optionally in a combination vaccine according to the invention. In a further embodiment, the inventive combination vaccine is to be administered to an individual in a pharmaceutically effective amount.

In a further aspect, the invention is directed to a kit comprising the components of the combination vaccine according to the invention and optionally technical instructions with information on the administration and dosage of the components of the combination vaccine, wherein the combination vaccine contains one or more RNAs (for example mRNAs), said RNAs encoding a first and for a second antigen, wherein the first antigen is a Fusion (F) protein or a fragment, variant or derivative of a Fusion (F) protein derived from the virus family Paramyxoviridae and wherein the second antigen is a Hemagglutinin (HA) protein or a fragment, variant or derivative of a Hemagglutinin (HA) protein derived from the virus family Orthomyxoviridae.

Beside the components of the combination vaccine the kit may additionally contain a pharmaceutically acceptable vehicle, an adjuvant and at least one further component as defined herein, as well as means for administration and technical instructions. The components of the combination vaccine and e.g. the adjuvant may be provided in lyophilized form. In a preferred embodiment, prior to use of the kit for vaccination, the provided vehicle is than added to the lyophilized components in a predetermined amount as written e.g. in the provided technical instructions. By doing so the combination vaccine, according to the above described aspects of the invention is provided that can afterwards be used in a method as described above, also.

Taken together the invention provides in a certain aspect a combination vaccine. The combination vaccine is for use in a method of prophylactic and/or therapeutic treatment of infections caused by viruses of the virus family Paramyxoviridae and/or of the virus family Orthomyxoviridae, particularly respiratory tract infections, e.g. RSV infection, mumps, measles, bronchitis, pneumonia, croup, distemper or rinderpest, and influenza. Accordingly, the invention relates to a combination vaccine as defined herein for use in a method of prophylactic and/or therapeutic treatment of infections caused by viruses of the virus family Paramyxoviridae and/or of the virus family Orthomyxoviridae, particularly respiratory tract infections, e.g. RSV infection, mumps, measles, bronchitis, pneumonia, croup, distemper or rinderpest, and influenza. The target group for such treatment preferably comprises infants, particularly pre-term infants (e.g. pre-term neonates), children, the elderly (e.g. people more than 60 years of age, preferably more than 65 years of age) and immunocompromised patients. Particularly, the invention provides a combination vaccine to be used in a method of preventing or treating respiratory tract infections, e.g. RSV infection, mumps, measles, bronchitis, pneumonia, croup, distemper or rinderpest, and influenza by administering the combination vaccine to pre-term infants, children, the elderly and immunocompromised patients, wherein the combination vaccine provokes a first adaptive immune response directed against an antigen that is similar or identical to the epitope of a Fusion (F) protein of Paramyxoviridae, and a second immune response elicited by an antigen that is similar or identical to the epitope of a Hemagglutinin (HA) protein of Orthomyxoviridae. Furthermore vaccination with a combination vaccine according to the invention can be supported by adjuvants. Such adjuvants may stimulate the innate immune system which in turn supports the adaptive immune response.

In the following, various aspects of the present invention are illustrated by the following items:

1. Composition comprising:
   a) an RNA, preferably mRNA, comprising or consisting of a nucleic acid sequence encoding a protein or peptide, said protein or peptide comprising or consisting of:
      i) the amino acid sequence of a Fusion (F) protein of the virus family Paramyxoviridae;
      ii) the amino acid sequence of a fragment of said Fusion (F) protein of the virus family Paramyxoviridae, said fragment having a length of at least 5 amino acids; and/or
      iii) an amino acid sequence exhibiting a sequence identity of at least 80% to said Fusion (F) protein of the virus family Paramyxoviridae of a) i) and/or said fragment of a) ii);
   and further comprising
   b) an RNA, preferably mRNA, comprising or consisting of a nucleic acid sequence encoding a protein or peptide, said protein or peptide comprising or consisting of:
      i) the amino acid sequence of a Hemagglutinin (HA) protein of the virus family Orthomyxoviridae,
      ii) the amino acid sequence of a fragment of said Hemagglutinin (HA) protein of the virus family Orthomyxoviridae, said fragment having a length of at least 5 amino acids and/or
      iii) an amino acid sequence exhibiting a sequence identity of at least 80% to said Hemagglutinin (HA) protein of the virus family Orthomyxoviridae of b) i) and/or said fragment of b) ii).

2. The composition according to item 1, wherein the Fusion (F) protein of the virus family Paramyxoviridae is a Fusion (F) protein of a virus selected from the group of: Avulavirus, Ferlavirus, Henipavirus, Morbillivirus, Respirovirus, Rubulavirus, TPMV-like viruses, Pneumovirus, Metapneumovirus, Atlantic salmon paramyxovirus, Beilong virus, J virus, Mossman virus, Nariva virus, Salem virus, and Pacific salmon paramyxovirus.

3. The composition according to item 2, wherein the Fusion (F) protein of the virus family Paramyxoviridae is a Fusion (F) protein of a Pneumovirus.

4. The composition according to item 3, wherein the Pneumovirus is human respiratory syncytial virus (RSV), preferably RSV Long or RSV A2.

5. The composition according to item 4, wherein the Fusion (F) protein of the virus family Paramyxoviridae comprises the sequence of SEQ ID No. 1 or SEQ ID No. 2 (or P102A, I379V, and M447V mutants of SEQ ID No. 2).

6. The composition according to any of the preceding items, wherein the Hemagglutinin (HA) protein of the virus family Orthomyxoviridae is a Hemagglutinin (HA) protein of an Influenza virus, preferably selected from the group consisting of: Influenza A (e.g. H1N1, H1N2, H2N2, H3N1, H3N2, H3N8, H5N1, H5N2, H5N3, H5N8, H5N9, H7N1, H7N2, H7N3, H7N4, H7N7, H9N1, H9N2, H10N7), Influenza B, Influenza C, Isavirus (e.g. Infectious salmon anemia virus), Thogotovirus (e.g. Dhori virus), Quaranfil virus, Johnston Atoll virus, and Lake Chad virus.

7. The composition according to any of the preceding items, wherein the Hemagglutinin (HA) protein of the virus family Orthomyxoviridae comprises the sequence of SEQ ID No. 3.
8. The composition according to any of the preceding items, wherein the composition comprises a combination selected from the group consisting of: RNA of a) i) and the RNA of b) i), RNA of a) i) and the RNA of b) ii), RNA of a) i) and the RNA of b) iii), RNA of a) ii) and the RNA of b) i), RNA of a) ii) and the RNA of b) ii), RNA of a) ii) and the RNA of b) iii), RNA of a) iii) and the RNA of b) i), RNA of a) iii) and the RNA of b) ii), and RNA of a) iii) and the RNA of b) iii); preferably wherein the composition comprises the RNA of a) i) and the RNA of b) i).
9. The composition according to item 8, wherein the RNA of a) and the RNA of b) are not the same nucleic acid molecule.
10. The composition according to item 8, wherein the RNA of a) and the RNA of b) are the same nucleic acid molecule.
11. The composition according to item 10, wherein said same nucleic molecule encodes the protein or peptide of a) i), a) ii) and/or a) iii); and the protein or peptide of b) i), b) ii) and/or b) iii) in bi- or multicistronic manner.
12. The composition according to item 10, wherein said nucleic acid molecule does not encode a fusion protein representing a combination of the amino acid sequence of a Fusion (F) protein of the virus family Paramyxoviridae, or fragment thereof with an HA tag of the sequence YPYDVPDYA (SEQ ID No. 22).
13. The composition according any of the preceding items wherein the RNA of b) does not encode a peptide consisting of and/or comprising an HA-tag of the sequence YPYDVPDYA (SEQ ID No. 22).
14. The composition according to any of the preceding items, wherein the composition comprises two or more different RNAs according to a), preferably encoding different peptides comprising the amino acid sequence of different fragments of said Fusion (F) protein of the virus family Paramyxoviridae, wherein most preferably the sequence of all encoded fragments aligned with each other covers the full length of said Fusion (F) protein of the virus family Paramyxoviridae.
15. The composition according to any of the preceding items, wherein the composition comprises two or more different RNAs according to b), preferably encoding different peptides comprising the amino acid sequence of different fragments of said Hemagglutinin (HA) protein of the virus family Orthomyxoviridae, wherein most preferably the sequence of all encoded fragments aligned with each other covers up to the full length of said Hemagglutinin (HA) protein of the virus family Orthomyxoviridae.
16. The composition according to any of the preceding items, wherein said fragment of said Fusion (F) protein of the virus family Paramyxoviridae, and/or said fragment of said Hemagglutinin (HA) protein of the virus family Orthomyxoviridae, selected independently of each other, has a length of at least 6 amino acids, preferably at least 7 amino acids, more preferably at least 8 amino acids, even more preferably at least 9 amino acids; even more preferably at least 10 amino acids; even more preferably at least 11 amino acids; even more preferably at least 12 amino acids; even more preferably at least 13 amino acids; even more preferably at least 14 amino acids; even more preferably at least 15 amino acids; even more preferably at least 16 amino acids; even more preferably at least 17 amino acids; even more preferably at least 18 amino acids; even more preferably at least 19 amino acids; even more preferably at least 20 amino acids; even more preferably at least 25 amino acids; even more preferably at least 30 amino acids; even more preferably at least 35 amino acids; even more preferably at least 50 amino acids; or most preferably at least 100 amino acids.
17. The composition according to any of the preceding items, wherein said fragment of said Fusion (F) protein of the virus family Paramyxoviridae, and/or said fragment of said Hemagglutinin (HA) protein of the virus family Orthomyxoviridae, is selected independently of each other from the first, second, third or fourth quarter of the amino acid sequence of said Fusion (F) protein of the virus family Paramyxoviridae and/or the amino acid sequence of said Hemagglutinin (HA) protein of the virus family Orthomyxoviridae, respectively.
18. The composition according to any of the preceding items, wherein the sequence identity of a) iii) and/or b) iii), selected independently of each other, is at least 85%, preferably at least 90%, even more preferably at least 92%; even more preferably at least 92%; even more preferably at least 94%; even more preferably at least 95%; even more preferably at least 96%; even more preferably at least 97%; even more preferably at least 98%; most preferably at least 99%.
19. The composition according to any of the preceding items, with the proviso that if the RNA of a) and the RNA of b) are the same nucleic acid molecule and the protein or peptide of a) and peptide of b) encoded by said same nucleic acid are the same protein or peptide, and said same protein or peptide comprises the sequence of SEQ ID No. 22, then said same nucleic acid molecule encodes a protein or peptide comprising:
I) an amino acid sequence of b i);
II) an amino acid sequence of b) ii), said fragment having a length of at least 10 amino acids, preferably at least 11 amino acids, more preferably at least 12 amino acids, more preferably at least 13 amino acids, more preferably at least 14 amino acids, more preferably at least 15 amino acids, more preferably at least 16 amino acids, more preferably at least 17 amino acids, more preferably at least 18 amino acids, more preferably at least 19 amino acids, most preferably at least 20 amino acids;
III) an amino acid sequence exhibiting a sequence identity of at least 80% to an Hemagglutinin (HA) protein of the virus family Orthomyxoviridae;
IV) an amino acid sequence exhibiting a sequence identity of at least 80% to of a fragment of an Hemagglutinin (HA) protein of the virus family Orthomyxoviridae, said fragment having a length of at least 12 amino acids; and/or
V) said sequence of SEQ ID No. 22 is present in the protein or peptide in addition to a further amino acid sequence according to bi), bii) or b iii), which further amino acid sequence does not comprise SEQ ID No. 22.

20. The composition according to any of the preceding items, wherein the RNA of a) and/or the RNA of b) are mRNA.
21. The composition according to any of the preceding items, wherein the RNA of a) comprises or consists of a nucleic acid sequence selected from the group consisting of SEQ ID No. 13, SEQ ID No. 14, SEQ ID No. 15, SEQ ID No. 16, SEQ ID No. 17, SEQ ID No. 19 or SEQ ID No. 20, in particular selected from SEQ ID No. 19 or SEQ ID No. 20, in particular wherein the composition comprises at least two monocistronic RNAs, wherein the composition is selected from the group: (a) at least one monocistronic RNA according to SEQ ID No.: 13 and at least one monocistronic RNA according to SEQ ID No.: 18 or SEQ ID No.: 21, (b) at least one monocistronic RNA according to SEQ ID No.: 14 and at least one monocistronic RNA according to SEQ ID No.: 18 or according to SEQ ID No.: 21, (c) at least one monocistronic RNA according to SEQ ID No.: 15 and at least one monocistronic RNA according to SEQ ID No.: 18 or SEQ ID No.: 21, (d) at least one monocistronic RNA according to SEQ ID No.: 16 and at least one monocistronic RNA according to SEQ ID No.: 18 or SEQ ID No.: 21, (e) at least one monocistronic RNA according to SEQ ID No.: 17 and at least one monocistronic RNA according to SEQ ID No.: 18 or SEQ ID No.: 21, (f) at least one monocistronic RNA according to SEQ ID No.: 19 and at least one monocistronic RNA according to SEQ ID No.: 18 or SEQ ID No.: 21, and (g) at least one monocistronic RNA according to SEQ ID No.: 20 and at least one monocistronic RNA according to SEQ ID No.: 18 or SEQ ID No.: 21, or functional fragments, variants or derivatives of any of the above SEQ ID Nos.
22. The composition according to any of the preceding items, wherein the RNA of b) comprises or consists of a nucleic acid sequence selected from the group consisting of SEQ ID No: 18 and SEQ ID No. 21.
23. The composition according to any of items 20 to 22, wherein:
    i) the RNA of a) comprises or consists of the sequence of SEQ ID No. 19 and/or SEQ ID No. 20; and
    ii) the RNA of b) comprises or consists of the sequence of SEQ ID No. 21.
24. The composition according to any of the preceding items, wherein the composition comprises an RNA consisting of the sequence of SEQ ID No. 19 or SEQ ID No. 20; and comprises an RNA consisting of the sequence of SEQ ID No. 21.
25. The composition according to any of the preceding items, wherein the RNA of a) and/or the RNA of b) comprise one, two or more than two of the following structural elements:
    i) a histone-stem-loop structure, preferably a histone-stem-loop in its 3' untranslated region;
    ii) a 5'-Cap structure;
    iii) a poly(C) sequence;
    iv) a poly-A tail; and/or
    v) a polyadenylation signal.
26. The composition according to any of items 1 to 19, wherein the RNA of a) and/or the RNA of b) are selfreplicating RNA, in particular RNA packaged in a replicon particle.
27. The composition according to any of items 20 to 26, wherein the mRNA of a) and/or the mRNA of b) are stabilized RNA, preferably RNA stabilized by complete or partial backbone modifications (e.g. over the full length of the sequence or only parts thereof), complete or partial sugar modifications (e.g. over the full length of the sequence or only parts thereof), complete or partial base modifications (e.g. over the full length of the sequence or only parts thereof), and/or by complete or partial modification of the G/C-content (e.g. over the full length of the sequence or only parts thereof).
28. The composition according to any of the preceding items, wherein the RNA of a) and/or the RNA of b) are codon optimized, in particular for human codon usage.
29. The composition according to any of the preceding items, wherein the RNA of a) and/or the RNA of b) are associated with or complexed with a cationic or polycationic compound or a polymeric carrier, optionally in a weight ratio selected independently of each other from a range of about 6:1 (w/w) to about 0.25:1 (w/w), more preferably from about 5:1 (w/w) to about 0.5:1 (w/w), even more preferably of about 4:1 (w/w) to about 1:1 (w:w) or of about 3:1 (w/w) to about 1:1 (w/w), and most preferably a ration of about 3:1 (w/w) to about 2:1 (w/w) of nucleic to cationic or polycationic compound and/or with a polymeric carrier; or optionally in a nitrogen/phosphate ratio of nucleic to cationic or polycationic compound and/or polymeric carrier in the range of about 0.1-10, preferably in a range of about 0.3-4 or 0.3-1, most preferably in a range of about 0.5-1 or 0.7-1, and even most preferably in a range of about 0.3-0.9 or 0.5-0.9.
30. The composition according to any of the preceding items, wherein the RNA of a) and/or the RNA of b) are associated or complexed with a cationic protein or peptide, preferably protamine.
31. The composition according to any of the preceding items, wherein the composition further comprises an adjuvant; preferably an adjuvant comprising or consisting of an oligo- or a polynucleotide; more preferably an adjuvant comprising or consisting of a RNA or a DNA; even more preferably an adjuvant comprising or consisting of a RNA or a DNA, said RNA or DNA being complexed with a cationic or polycationic compound and/or with a polymeric carrier; optionally in a weight ratio selected from a range of about 6:1 (w/w) to about 0.25:1 (w/w), more preferably from about 5:1 (w/w) to about 0.5:1 (w/w), even more preferably of about 4:1 (w/w) to about 1:1 (w:w) or of about 3:1 (w/w) to about 1:1 (w/w), and most preferably a ration of about 3:1 (w/w) to about 2:1 (w/w) of adjuvant component to cationic or polycationic compound and/or with a polymeric carrier; or optionally in a nitrogen/phosphate ratio of the adjuvant component to cationic or polycationic compound and/or polymeric carrier in the range of about 0.1-10, preferably in a range of about 0.3-4 or 0.3-1, and most preferably in a range of about 0.7-1 or 0.5-1, and even most preferably in a range of about 0.3-0.9 or 0.5-0.9.
32. The composition according to any of the preceding items, wherein the composition further comprises an auxiliary substance selected from lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (isRNA), a CpG-DNA, an antibacterial agent, or an anti-viral agent.
33. The composition according to any of the preceding items, wherein the composition is a pharmaceutical composition optionally further comprising a pharmaceutically acceptable carrier, excipient or diluent.
34. The composition according to item 33, wherein the composition is formulated for parenteral, oral, nasal, pulmonary, topical, rectal, buccal, or vaginal administration or for administration by inhalation or via an implanted reservoir.
35. The composition according to any of items 1 to 34 for use in a method of prophylactic and/or therapeutic treatment of the human or animal body.
36. The composition according to any of items 1 to 34 for use in a method of prophylactic and/or therapeutic treatment of infections caused by viruses of the virus family Paramyxoviridae and/or of the virus family Orthomyxoviridae, particularly respiratory tract infections; preferably RSV infection, mumps, measles, bronchitis, pneumonia, croup, distemper or rinderpest, and/or influenza.
37. The composition according to item 35 or 36 for use as vaccine.
38. The composition according to any of items 35 to 37, wherein the method comprises the in vitro transfection of isolated cells.
39. The composition according to any of items 35 to 38, wherein the individual to be treated is selected from the group consisting of infants, particularly pre-term neonates, children, the elderly and immunocompromised patients.
40. Kit comprising:
    a) an RNA, preferably mRNA, comprising or consisting of a nucleic acid sequence encoding a protein or peptide, said protein or peptide comprising or consisting of:
    i) the amino acid sequence of a Fusion (F) protein of the virus family Paramyxoviridae;
    ii) the amino acid sequence of a fragment of said Fusion (F) protein of the virus family Paramyxoviridae, said fragment having a length of at least 5 amino acids; and/or
    iii) an amino acid sequence exhibiting a sequence identity of at least 80% to said Fusion (F) protein of the virus family Paramyxoviridae of a) i) and/or said fragment of a) ii);
    and further comprising
    b) an RNA, preferably mRNA, comprising or consisting of a nucleic acid sequence encoding a protein or peptide, said protein or peptide comprising or consisting of:
    i) the amino acid sequence of a Hemagglutinin (HA) protein of the virus family Orthomyxoviridae,
    ii) the amino acid sequence of a fragment of said Hemagglutinin (HA) protein of the virus family Orthomyxoviridae, said fragment having a length of at least 5 amino acids and/or
    iii) an amino acid sequence exhibiting a sequence identity of at least 80% to said Hemagglutinin (HA) protein of the virus family Orthomyxoviridae of b) i) and/or said fragment of b) ii).
41. The kit according to item 40, wherein the RNA of a) and the RNA of b) are as defined in any of items 2 to 34.
42. The kit according to item 40 or 41 for use in a method of prophylactic and/or therapeutic treatment of the human or animal body.
43. The kit according to any of items 40 to 42 for use in a method of prophylactic and/or therapeutic treatment of infections caused by viruses of the virus family Paramyxoviridae and/or of the virus family Orthomyxoviridae, particularly respiratory tract infections; preferably RSV infection, mumps, measles, bronchitis, pneumonia, croup, distemper or rinderpest, and/or influenza.
44. The kit according to item 40 or 41 for use as vaccine.
45. The kit according to any of items 40 to 44, wherein the method comprises the in vitro transfection of isolated cells.
46. The kit according to any of items 40 to 45, wherein the individual to be treated is selected from the group consisting of infants, particularly pre-term neonates, children, the elderly and immunocompromised patients.
47. Method of prophylactic and/or therapeutic treatment of infections caused by viruses of the virus family Paramyxoviridae and/or of the virus family Orthomyxoviridae, particularly respiratory tract infections; preferably RSV infection, mumps, measles, bronchitis, pneumonia, croup, distemper or rinderpest, and/or influenza, wherein the method comprises administration of an effective amount of the composition according to any of items 1 to 35, or kit according to any of items 41 to 42.
48. The method to item 47, wherein said composition or kit is used as vaccine.
49. The method according to item 47 or 48, wherein the method comprises the in vitro transfection of isolated cells.
50. The method according to any of items 47 to 49, wherein the individual to be treated is selected from the group consisting of infants, particularly pre-term neonates, children, the elderly and immunocompromised patients.
51. Nucleic acid comprising or consisting of a sequence selected from the group of: SEQ ID No. 7, SEQ ID No. 8, SEQ ID No. 9, SEQ ID No. 10, SEQ ID No. 11, and SEQ ID No: 12.
52. Nucleic acid comprising or consisting of a sequence selected from the group of: SEQ ID No. 13, SEQ ID No. 14, SEQ ID No. 15, SEQ ID No. 16, SEQ ID No. 17, and SEQ ID No: 18.
53. Nucleic acid according to item 52, the nucleic acid comprising or consisting of a sequence selected from the group of: SEQ ID No. 19, SEQ ID No. 20 and SEQ ID No. 21.
54. RNA, preferably mRNA, comprising or consisting of a nucleic acid sequence encoding a protein or peptide, said protein or peptide comprising or consisting of:
    i) the amino acid sequence of a Fusion (F) protein of the virus family Paramyxoviridae;
    ii) the amino acid sequence of a fragment of said Fusion (F) protein of the virus family Paramyxoviridae, said fragment having a length of at least 5 amino acids; and/or iii) an amino acid sequence exhibiting a sequence identity of at least 80% to said Fusion (F) protein of the virus family Paramyxoviridae of a) i) and/or said fragment of a) ii);

for use in a method according to any of items 47 to 50.

55. The RNA of item 54, wherein the RNA is as defined in any of items 2 to 5, 9 to 13, 16 to 21, or 25 to 32, in particular wherein the RNA comprises or consists of a sequence selected from the group consisting of SEQ ID No. 13, SEQ ID No. 14, SEQ ID No. 15, SEQ ID No. 16, SEQ ID No. 17, SEQ ID No. 19 and SEQ ID No. 20.

56. RNA, preferably mRNA, comprising or consisting of a nucleic acid sequence encoding a protein or peptide, said protein or peptide comprising or consisting of:
   i) the amino acid sequence of a Hemagglutinin (HA) protein of the virus family Orthomyxoviridae,
   ii) the amino acid sequence of a fragment of said Hemagglutinin (HA) protein of the virus family Orthomyxoviridae, said fragment having a length of at least 5 amino acids and/or
   iii) an amino acid sequence exhibiting a sequence identity of at least 80% to said Hemagglutinin (HA) protein of the virus family Orthomyxoviridae of b) i) and/or said fragment of b) ii);

for use in a method according to any of items 47 to 50.

57. The RNA of item 56, wherein the RNA is as defined in any of items 6 to 7, 9 to 13, 16 to 20, 22, or 25 to 32, in particular wherein the RNA comprises or consists of a sequence selected from the group consisting of SEQ ID No: 18 or SEQ ID No. 21.

It is understood that the subject-matter of any of the above mentioned items may be combined with or modified according to any of the possibilities (or any features thereof) described in the instant description of the present invention.

Further, it is emphasized again that an HA-tag is preferably not used according to the invention as fragment of said Hemagglutinin (HA) protein of the virus family Orthomyxoviridae. RNA encoding a mere HA-tagged Fusion (F) proteins of the virus family Paramyxoviridae, e.g. a Fusion (F) protein of the virus family Paramyxoviridae linked (optionally via a short 1 to 10 amino acid peptide linker) to an HA tag—or nucleic acids encoding the same—is not an preferred embodiment of composition of the invention. However, there are several possibilities in which presence of an HA-tag is possible. For example, if an HA tag sequence is present in such fusion protein, the encoded fusion protein must preferably comprise as Hemagglutinin (HA) derived portion (peptide b in item 1) aside of the HA tag preferably also other sequence elements of an Hemagglutinin protein. For example, the Hemagglutinin (HA) derived portion (see peptide b in item 1) may be longer than the real HA tag or may comprise elsewhere in its sequence additional Hemagglutinin protein derived sequence elements of sufficient length (e.g. sequence stretches of preferably 5 or more amino acids). An additional HA tag, i.e. in addition to another non-HA sequence qualifying as Hemagglutinin (HA) derived portion (see peptide b in item 1), is also possible. Likewise, the fusion of fragments of an Fusion (F) protein—instead of the full length F>Uion (F) protein—with an HA tag is not excluded from the scope of the present invention. A fusion protein of an Fusion (F) protein as defined herein with an HA tag is furthermore particularly acceptable, when the composition comprises—aside of said fusion protein—another distinct peptide which fulfils the requirements of peptide b in item 1 in lieu thereof.

In any event, the inventive medical application of such RNA encoding an HA tagged Fusion (F) protein is clearly contemplated by the present invention, for example as vaccine or in a method of treatment as disclosed herein.

In the present invention, if not otherwise indicated, different features of alternatives and embodiments may be combined with each other, where suitable. Furthermore, the term "comprising" shall not be narrowly construed as being limited to "consisting of" only, if not specifically mentioned. Rather, in the context of the present invention, "consisting of" is an embodiment specifically contemplated by the inventors to fall under the scope of "comprising", wherever "comprising" is used herein.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

BRIEF DESCRIPTION OF THE DRAWINGS

The following Figures are intended to illustrate the invention further. They are not intended to limit the subject matter of the invention thereto.

As can be seen from the results, the combination of both coding mRNAs in one vaccine synergistically increases the induction of F protein specific cytotoxic T cells (CTLs). But this effect is only visible if both mRNAs are comprised in the same pharmaceutical composition (combination vaccine) and are not separately injected.

Figure 2:
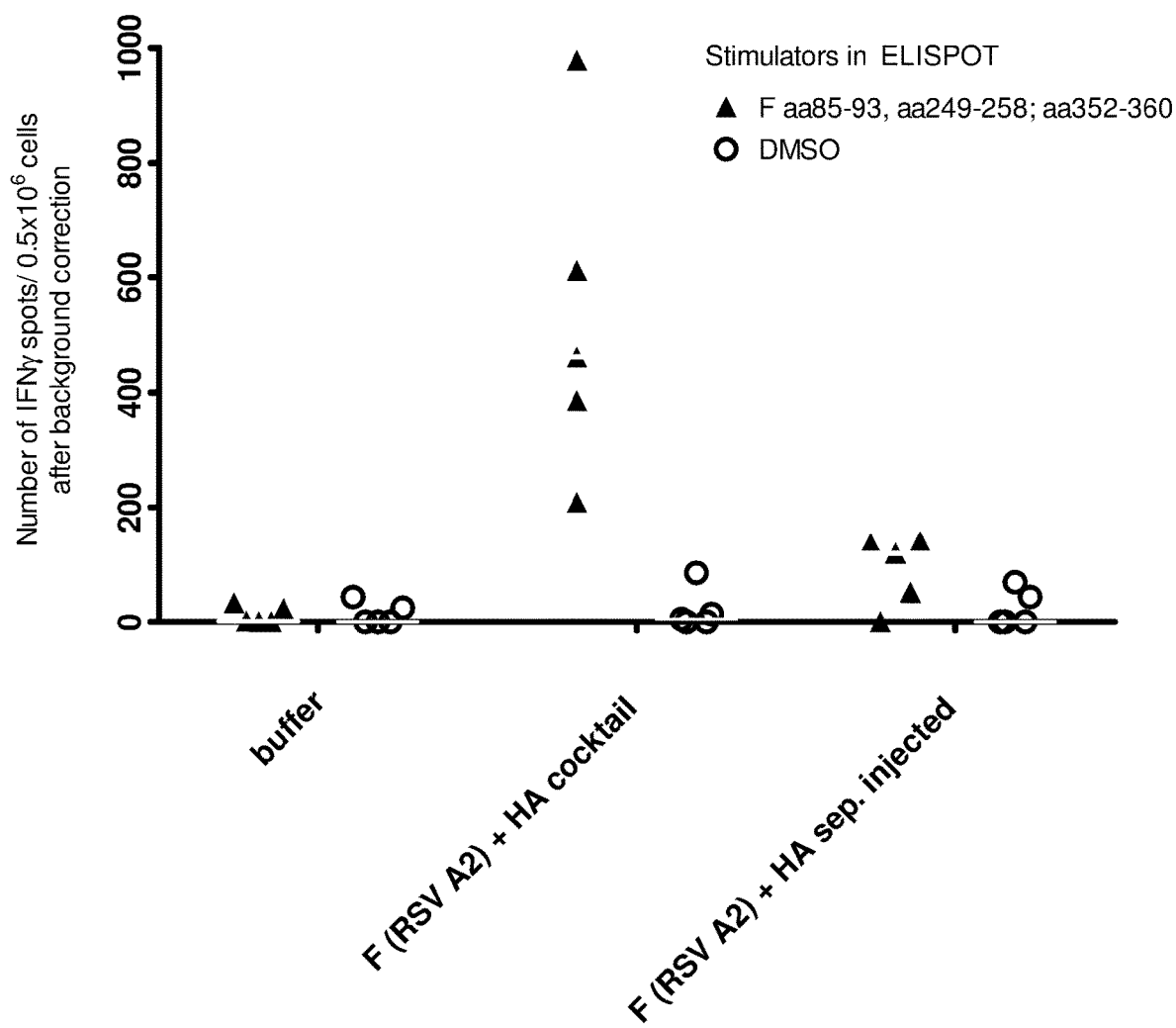

FIG. 2: shows the induction of a RSV F protein specific CTL immune response in BALB/c mice after vaccination with mRNA coding for RSV A2 F protein and mRNA coding for HA (Hemagglutinin of A/Puerto Rico/8/34), injected in one pharmaceutical composition (F (RSV A2)+HA cocktail) or separately injected (F (RSV A2)+HA sep. injected). For negative control, mice were treated with buffer. Four weeks after the last vaccination antigen specific T cells were analysed in spleens of vaccinated mice by ELISPOT analysis. Splenocytes were either stimulated with three $H-2k^d$-restricted T-cell epitopes of the F protein (KYKNAVTEL (amino acids 85-93; SEQ ID No. 24), TYMLTNSELL (amino acids 249-258; SEQ ID No. 25), FPQAETCKV (amino acids 352-360; SEQ ID No. 26)) or DMSO alone. Lines represent the median.

As can be seen from the results, the combination of both coding mRNAs in one vaccine synergistically increases the induction of F protein specific cytotoxic T cells (CTLs). But this effect is only visible if both mRNAs are comprised in the same pharmaceutical composition (combination vaccine) and are not separately injected.

Figure 3:
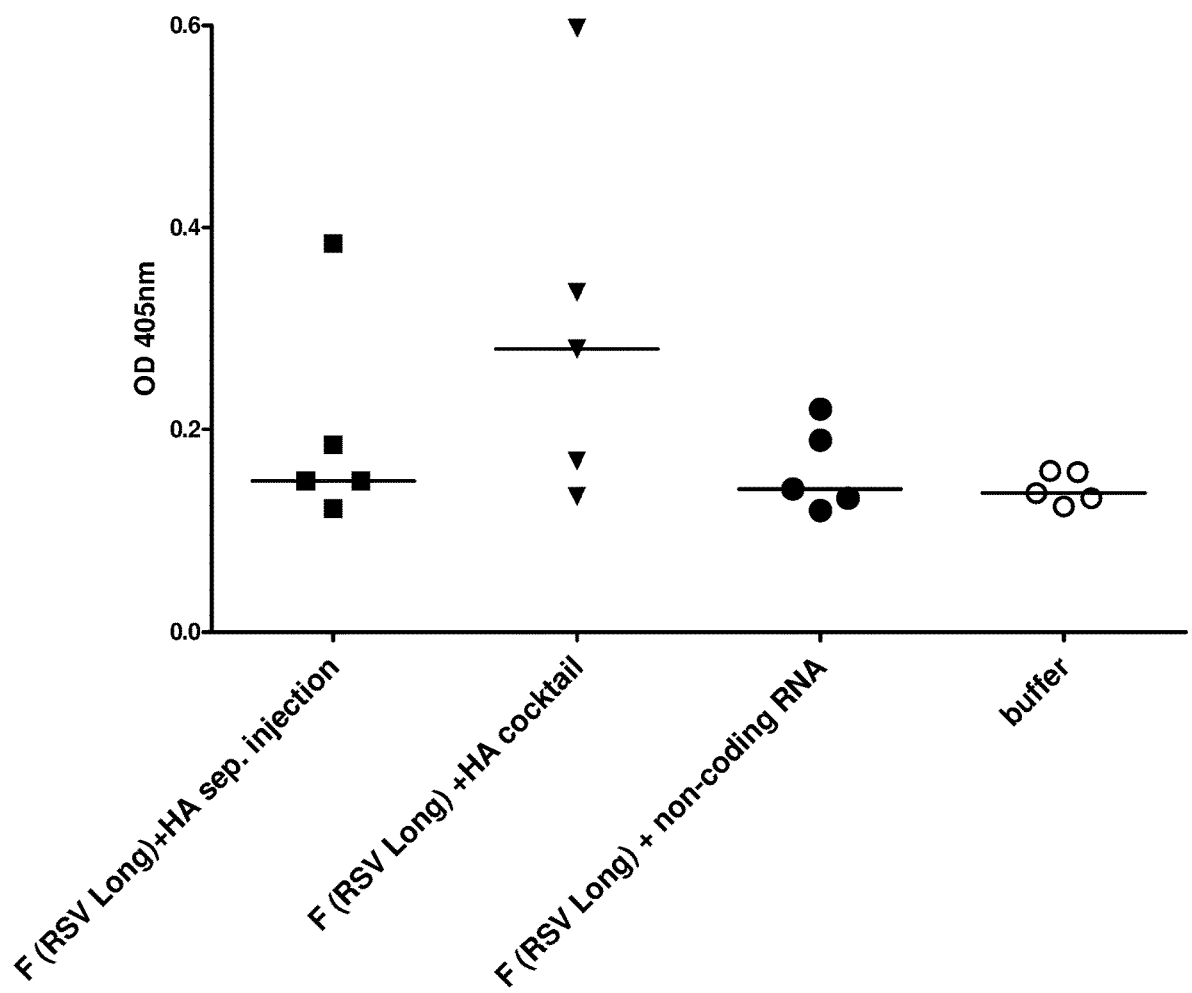

FIG. 3: shows the induction of RSV F protein specific antibodies in BALB/c mice 2 weeks after the last vaccination with mRNA coding for RSV Long F protein and mRNA coding for HA (Hemagglutinin of A/Puerto Rico/8/34), injected in one pharmaceutical composition (F (RSV Long)+HA cocktail) or separately injected (F (RSV Long)+HA sep. injected). To control for unspecific immune effects of the cocktail application, one group was treated with a cocktail of mRNA coding for F protein (RSV Long) and a non-coding RNA. For negative control, mice were treated with buffer. Two weeks after the last vaccination F protein specific antibodies were analysed in serum of vaccinated mice. Lines represent the median.

As can be seen from the results, the combination of both coding mRNAs in one pharmaceutical composition increases the induction of F protein specific antibodies in 3 of 5 mice compared to the group vaccinated with the combination of mRNA coding for F protein and non-coding RNA.

FIG. 4: shows the induction of HA protein specific antibodies in BALB/c mice 4 weeks after the last vaccination with mRNA encoding the HA protein of A/Puerto Rico/8/1934 or a combination of HA mRNA and F protein (RSV Long) encoding mRNA vaccine. Mice either received the two mRNAs at separate injection sites (F+HA sep. injected) or as a cocktail of both mRNAs. For negative control, mice were treated with buffer. Four weeks after second immunization antigen specific antibodies were analysed in serum of vaccinated mice. Lines represent the median.

As can be seen from the results, the combination of both coding mRNAs has no effect on the induction of HA protein specific antibodies compared to the group with was vaccinated only with mRNA coding for HA.

FIG. 5: shows the protein sequence of the Fusion (F) protein of RSV Long (NCBI Accession No. AAX23994) according to SEQ ID No. 1.

FIG. 6: shows the protein sequence of the Fusion (F) protein of RSV A2 (NCBI Accession No. AAB59858) according to SEQ ID No. 2.

FIG. 7: shows the protein sequence of the Hemagglutinin (HA) protein of Influenza A/Puerto Rico/8/1934 (NCBI Accession No. AB021709) according to SEQ ID No. 3.

FIG. 8: shows the wild type coding sequence of Fusion (F) protein of RSV Long (Human respiratory syncytial virus strain ATCC VR-26 (NCBI Accession No. AY911262) according to SEQ ID No. 4.

FIG. 9: shows the wild type coding sequence of Fusion (F) protein of RSV A2 (NCBI Accession No. M11486.1) according to SEQ ID No. 5.

FIG. 10: shows the wild type coding sequence of Hemagglutinin (HA) protein of Influenza A/Puerto Rico/8/1934 (NCBI Accession No. EF467821) according to SEQ ID No. 6.

FIG. 11: shows the GC-enriched DNA coding sequence (SEQ ID No. 7) coding for the Fusion (F) protein of RSV Long.

FIG. 12: shows the GC-enriched DNA coding sequence (SEQ ID No. 8) coding for the Fusion (F) protein of RSV A2.

FIG. 13: shows the GC-enriched DNA coding sequence (SEQ ID No. 9) coding for the Fusion (F) protein of RSV A2 (P102A).

FIG. 14: shows the GC-enriched DNA coding sequence (SEQ ID No. 10) coding for the Fusion (F) protein of RSV A2 (I379V).

FIG. 15: shows the GC-enriched DNA coding sequence (SEQ ID No. 11) coding for the Fusion (F) protein of RSV A2 (M447V).

FIG. 16: shows the GC-enriched DNA coding sequence (SEQ ID No: 12) coding for the Hemagglutinin (HA) protein of Influenza A/Puerto Rico/8/1934.

FIG. 17: shows an GC-enriched RNA sequence without UTRs (SEQ ID No. 13) coding for the Fusion (F) protein of RSV Long.

FIG. 18: shows an GC-enriched RNA sequence without UTRs (SEQ ID No. 14) coding for the Fusion (F) protein of RSV A2.

FIG. 19: shows an GC-enriched RNA sequence without UTRs (SEQ ID No. 15) coding for the Fusion (F) protein of RSV A2 (P102A).

FIG. 20: shows an GC-enriched RNA sequence without UTRs (SEQ ID No. 16) coding for the Fusion (F) protein of RSV A2 (I379V).

FIG. 21: shows an GC-enriched RNA sequence without UTRs (SEQ ID No. 17) coding for the Fusion (F) protein of RSV A2 (M447V).

FIG. 22: shows an GC-enriched RNA sequence without UTRs (SEQ ID No: 18) coding for the Hemagglutinin (HA) protein of Influenza A/Puerto Rico/8/1934.

FIG. 23: shows the GC-enriched full mRNA sequence coding for the Fusion (F) protein of RSV Long according to SEQ ID No. 19.

FIG. 24: shows the GC-enriched full mRNA sequence coding for the Fusion (F) protein of RSV A2 according to SEQ ID No. 20.

FIG. 25: shows the GC-enriched full mRNA sequence coding for the Hemagglutinin (HA) protein of Influenza A/Puerto Rico/8/1934 according to SEQ ID No. 21.

FIG. 26: shows the non-coding RNA according to SEQ ID No. 23 used as a control.

EXAMPLES

The following examples are intended to illustrate the invention further. They are not intended to limit the subject matter of the invention thereto.

Example 1—Preparation of mRNA Constructs

For the present examples DNA sequences, encoding the F protein of RSV-Long (SEQ ID No. 1), RSV-A2 (SEQ ID No. 2) and Hemagglutinin of A/Puerto Rico/8/34 (HA) (SEQ ID No. 3), and non-coding RNA as control (SEQ ID No. 23), were prepared and used for subsequent in vitro transcription reactions.

All used DNA sequences (SEQ ID No. 7, SEQ ID No. 8 and SEQ ID No: 12) were prepared by modifying the wild type encoding DNA sequences by introducing a GC-optimized sequence for a better codon usage and stabilization. In SEQ ID No. 19, SEQ ID No. 20 and SEQ ID No. 21 the sequences of the corresponding mRNAs are shown. The sequences was furthermore introduced into a pCV19 vector and modified to comprise stabilizing sequences derived from alpha-globin-3'-UTR (muag (mutated alpha-globin-3'-UTR)), a histone-stem-loop structure, and a stretch of 70×adenosine at the 3'-terminal end (poly-A-tail).

In a further step, the respective DNA plasmids prepared above were transcribed into mRNA in vitro using T7-Polymerase. Subsequently the obtained mRNA was purified using PureMessenger® (CureVac, Tubingen, Germany).

All obtained mRNAs used herein were furthermore complexed with protamine prior to use. The mRNA complexation consisted of a mixture of 50% free mRNA and 50% mRNA complexed with protamine at a weight ratio of 2:1. First, mRNA was complexed with protamine by slow addition of protamine-Ringer's lactate solution to mRNA. As soon as the complexes were stably generated, free mRNA was added, stirred shortly and the final concentration of the vaccine was adjusted with Ringer's lactate solution.

Example 2—Vaccination of Mice with RSV A2 and Influenza HA

BALB/c mice were vaccinated twice intradermally with the vaccine comprising 80 µg mRNA coding for HA (Hemagglutinin of A/Puerto Rico/8/34) and 80 µg mRNA coding for F protein (RSV-A2). Mice either received the two mRNAs at separate injection sites (F (RSV A2)+HA sep. injected) or as a cocktail of both mRNAs (F (RSV A2)+HA cocktail). For negative control, mice were treated with buffer.

Example 3—Vaccination of Mice with RSV Long and Influenza HA

BALB/c mice were vaccinated twice intradermally with the vaccine comprising 10 µg mRNA coding for HA (Hemagglutinin of A/Puerto Rico/8/34) and 10 µg mRNA coding for F protein (RSV-Long). Mice either received the two mRNAs at separate injection sites (F (RSV Long)+HA sep. injected) or as a cocktail of both mRNAs (F (RSV Long)+HA cocktail. To control for unspecific immune effects of the cocktail application, one group was treated with a cocktail of F (RSV Long) mRNA and a non-coding RNA (F (RSV Long)+non-coding RNA). For negative control, mice were treated with buffer.

Example 4—Detection of an Antigen-Specific B-Cell Immune Response (Antibodies)

Detection of an antigen specific immune response was carried out by detecting RSV F protein or HA protein specific antibodies. Therefore, blood samples were taken from vaccinated mice two and four weeks after the last vaccination and sera were prepared. MaxiSorp® plates (Nalgene Nunc International) were coated with F (Sino Biological Inc.) or HA protein (Charles River Laboratories). After blocking with 1×PBS containing 0.05% Tween-20 and 1% BSA the plates were incubated with diluted mouse serum (1:50). Subsequently a biotin-coupled secondary antibody (Anti-mouse-IgG Dianova, cat. #115035003) was added. After washing, the plate was incubated with Horseradish peroxidase-streptavidin and subsequently the conversion of the ABTS substrate (2,2'-azino-bis(3-ethyl-benzthiazoline-6-sulfonic acid) was measured. Results of these experiments are shown in FIGS. 3 and 4.

Figure 1:
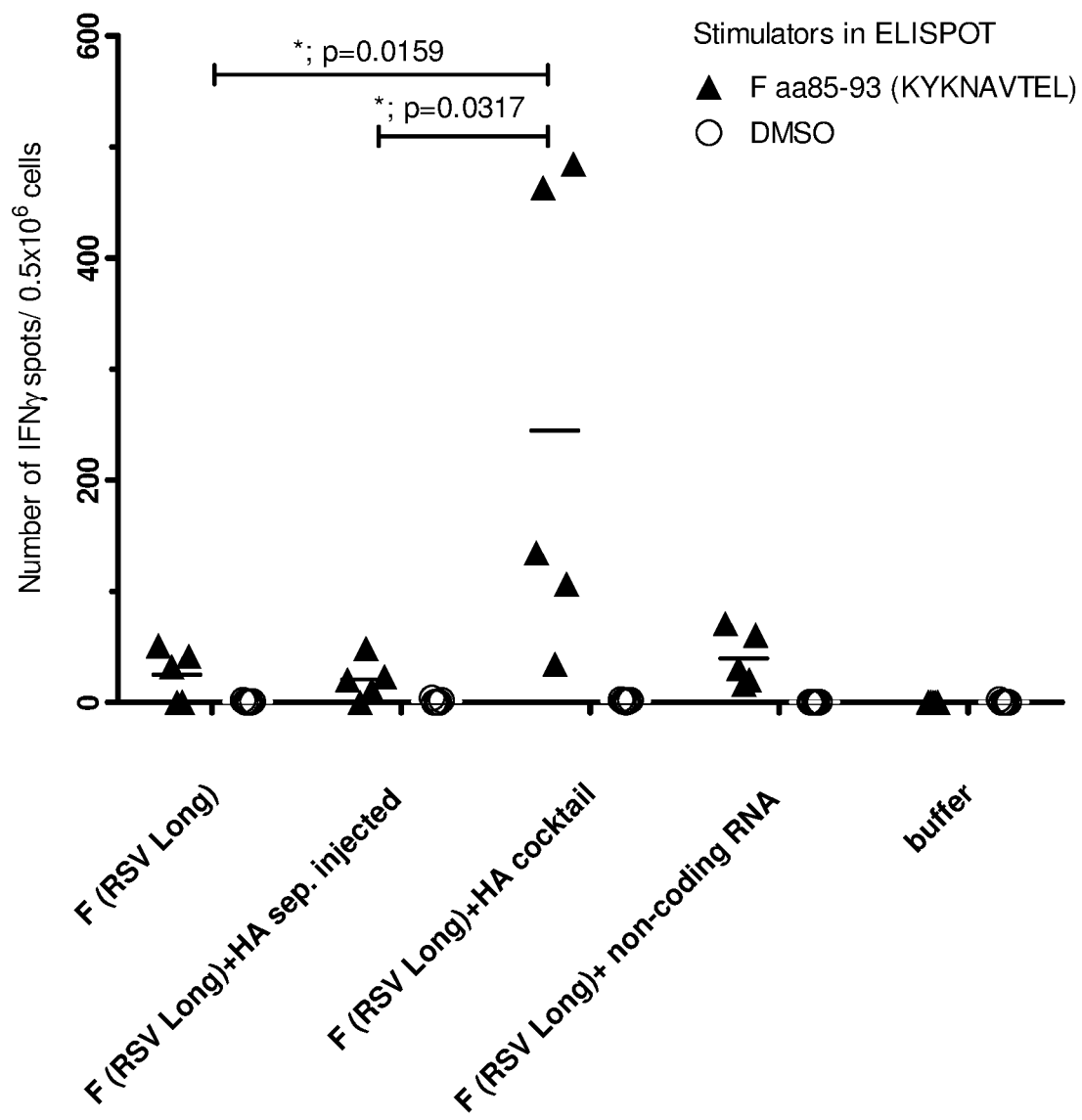
FIG. 1: shows the induction of a RSV F protein specific CTL immune response in BALB/c mice after vaccination with mRNA coding for RSV Long F protein and mRNA coding for HA (Hemagglutinin of A/Puerto Rico/8/34), injected in one pharmaceutical composition (F (RSV Long)+HA cocktail) or separately injected (F (RSV Long)+HA sep. injected). To control for unspecific immune effects of the cocktail application, one group was treated with a cocktail of mRNA coding for F protein (RSV Long) and a non-coding RNA. For negative control, mice were treated with buffer. One week after the last vaccination antigen specific T cells were analysed in spleens of vaccinated mice by ELISPOT analysis. Splenocytes were either stimulated with an $H-2k^d$-restricted T-cell epitope of the F protein KYKNAVTEL (amino acids 85-93; SEQ ID No. 24) or DMSO alone. Lines represent the median. Statistical analysis was done by the Mann-Whitney test.

Example 5—Detection of an Antigen Specific Cellular Immune Response by ELISPOT Four weeks (mice immunized with HA and RSV-A2, example 2) or one week (mice immunized with HA and RSV-Long, example 3) after the last vaccination mice were sacrificed, the spleens were removed and the splenocytes were isolated. For detection of INFgamma a coat multiscreen plate (Millipore) was incubated overnight with coating buffer 0.1 M Carbonat-Bicarbonat Buffer pH 9.6, 10.59 g/l $Na_2CO_3$, 8.4 g/l $NaHCO_3$) comprising antibody against INFγ (BD Pharmingen, Heidelberg, Germany). The next day $5\times10^5$ cells/well were added and re-stimulated with a cocktail of F protein specific epitopes KYKNAVTEL (amino acids 85-93; SEQ ID No. 24), TYMLTNSELL (amino acids 249-258; SEQ ID No. 25), FPQAETCKV (amino acids 352-360; SEQ ID No. 26), 1.25 µg of each epitope/well (mice immunized with HA and RSV-A2, example 2), or with 1.25 µg/well of F protein specific epitope KYKNAVTEL (amino acids 85-93; SEQ ID No. 24) alone (mice immunized with HA and RSV-Long, example 3). As control DMSO was used. Afterwards the cells are incubated for 24 h at 37° C. The next day the plates were washed twice with PBS, once with water and once with PBS/0.05% Tween-20 and afterwards incubated with a biotin-coupled secondary antibody for 11-24 h at 4° C. Then the plates were washed with PBS/0.05% Tween-20 and incubated for 2 h with alkaline phosphatase coupled to streptavidin in blocking buffer. After washing with PBS/0.05% Tween-20 the substrate (5-Bromo-4-Cloro-3-Indolyl Phosphate/Nitro Blue Tetrazolium Liquid Substrate System from Sigma Aldrich, Taufkirchen, Germany) was added to the plate and the conversion of the substrate could be detected visually. The reaction was then stopped by washing the plates with water. The dried plates were then read out by an ELISPOT plate reader. For visualization of the spot levels the numbers were corrected by background subtraction. Results of these experiments were shown in FIGS. 1 and 2.

---

SEQUENCE LISTING

```
<160> NUMBER OF SEQ ID NOS: 26

<210> SEQ ID NO 1
<211> LENGTH: 574
<212> TYPE: PRT
<213> ORGANISM: Human respiratory syncytial virus

<400> SEQUENCE: 1

Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30
```

```
Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Asn
 65                  70                  75                  80

Gln Glu Leu Asp Lys Tyr Lys Asn Ala Val Thr Glu Leu Gln Leu Leu
                85                  90                  95

Met Gln Ser Thr Thr Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
            115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
    195                 200                 205

Lys Gln Ser Cys Arg Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Gln Glu Gly
```

```
                450             455             460
Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu His His Val Asn Ala Gly Lys Ser Thr Thr Asn Ile Met Ile Thr
                515                 520                 525

Thr Ile Ile Ile Val Ile Ile Val Ile Leu Leu Ser Leu Ile Ala Val
                530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 2
<211> LENGTH: 574
<212> TYPE: PRT
<213> ORGANISM: Human respiratory syncytial virus

<400> SEQUENCE: 2

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
                35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
                100                 105                 110

Arg Phe Met Asn Tyr Thr Leu Asn Asn Ala Lys Lys Thr Asn Val Thr
                115                 120                 125

Leu Ser Lys Lys Arg Lys Arg Arg Phe Leu Gly Phe Leu Leu Gly Val
                130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
                195                 200                 205

Lys Gln Ser Cys Ser Ile Ser Asn Ile Glu Thr Val Ile Glu Phe Gln
                210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255
```

-continued

Leu Leu Ser Leu Ile Asn Asp Met Pro Ile Thr Asn Asp Gln Lys Lys
             260                 265                 270

Leu Met Ser Asn Asn Val Gln Ile Val Arg Gln Gln Ser Tyr Ser Ile
         275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Ile Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 3
<211> LENGTH: 565
<212> TYPE: PRT
<213> ORGANISM: Influenza A virus

<400> SEQUENCE: 3

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

```
Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Asn
            130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
            195                 200                 205

Gln Asn Glu Asn Ala Tyr Val Ser Val Val Thr Ser Asn Tyr Asn Arg
210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
            275                 280                 285

His Glu Cys Asn Thr Lys Cys Gln Thr Pro Leu Gly Ala Ile Asn Ser
290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
            355                 360                 365

His Gln Asn Glu Gln Gly Ser Gly Tyr Ala Ala Asp Gln Lys Ser Thr
            370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
            450                 455                 460

Val Lys Ser Gln Leu Lys Asn Asn Ala Lys Glu Ile Gly Asn Gly Cys
465                 470                 475                 480
```

```
Phe Glu Phe Tyr His Lys Cys Asp Asn Glu Cys Met Glu Ser Val Arg
                485                 490                 495
Asn Gly Thr Tyr Asp Tyr Pro Lys Tyr Ser Glu Glu Ser Lys Leu Asn
            500                 505                 510
Arg Glu Lys Val Asp Gly Val Lys Leu Glu Ser Met Gly Ile Tyr Gln
        515                 520                 525
Ile Leu Ala Ile Tyr Ser Thr Val Ala Ser Ser Leu Val Leu Val
    530                 535                 540
Ser Leu Gly Ala Ile Ser Phe Trp Met Cys Ser Asn Gly Ser Leu Gln
545                 550                 555                 560
Cys Arg Ile Cys Ile
                565

<210> SEQ ID NO 4
<211> LENGTH: 1725
<212> TYPE: DNA
<213> ORGANISM: Human respiratory syncytial virus

<400> SEQUENCE: 4
atggagttgc caatcctcaa agcaaatgca attaccacaa tcctcgctgc agtcacattt      60
tgctttgctt ctagtcaaaa catcactgaa gaatttatc aatcaacatg cagtgcagtt     120
agcaaaggct atcttagtgc tctaagaact ggttggtata ctagtgttat aactatagaa     180
ttaagtaata tcaaggaaaa taagtgtaat ggaacagatg ctaaggtaaa attgataaac     240
caagaattag ataaatataa aaatgctgta acagaattgc agttgctcat gcaaagcaca     300
acagcagcaa caatcgagc cagaagagaa ctaccaaggt ttatgaatta cactcaac      360
aataccaaaa aaaccaatgt aacattaagc aagaaaagga aagaagatt cttggtttt      420
ttgttaggtg ttggatctgc aatcgccagt ggcattgctg tatctaaggt cctgcactta     480
gaaggagaag tgaacaagat caaaagtgct ctactatcca caacaaggc cgtagtcagc     540
ttatcaaatg gagttagtgt cttaaccagc aaagtgttag acctcaaaaa ctatatagat     600
aaacaattgt tacctattgt gaataagcaa agctgcagaa tatcaaatat agaaactgtg     660
atagagttcc aacaaaagaa caacagacta ctagagatta ccagggaatt tagtgttaat     720
gcaggtgtaa ctacacctgt aagcacttac atgttaacta atagtgaatt attgtcatta     780
atcaatgata tgcctataac aaatgatcag aaaaagttaa tgtccaacaa tgttcaaata     840
gttagacagc aaagttactc tatcatgtcc ataataaaag aggaagtctt agcatatgta     900
gtacaattac cactatatgg tgtgatagat acaccttgtt ggaaattaca cacatcccct     960
ctatgtacaa ccaacacaaa agaagggtca acatctgtt aacaagaac tgacagagga    1020
tggtactgtg acaatgcagg atcagtatct ttcttcccac aagctgaaac atgtaaagtt    1080
caatcgaatc gagtattttg tgacacaatg aacagtttaa cattaccaag tgaagtaaat    1140
ctctgcaatg ttgacatatt caatcccaaa tatgattgta aaattatgac ttcaaaaaca    1200
gatgtaagca gctccgttat cacatctcta ggagccattg tgtcatgcta tggcaaaact    1260
aaatgtacag catccaataa aaatcgtgga atcataaaga cattttctaa cgggtgtgat    1320
tatgtatcaa ataagggggt ggacactgtg tctgtaggta acacattata ttatgtaaat    1380
aagcaagaag gcaaaagtct ctatgtaaaa ggtgaaccaa taataaattt ctatgaccca    1440
ttagtattcc cctctgatga atttgatgca tcaatatctc aagtcaatga gaagattaac    1500
cagagtttag catttattcg taatccgat gaattattac atcatgtaaa tgctggtaaa    1560
tcaaccacaa atatcatgat aactactata attatagtga ttatagtaat attgttatca    1620
```

```
ttaattgctg ttggactgct cctatactgt aaggccagaa gcacaccagt cacactaagc    1680
aaggatcaac tgagtggtat aaataatatt gcatttagta actga                   1725

<210> SEQ ID NO 5
<211> LENGTH: 1725
<212> TYPE: DNA
<213> ORGANISM: Human respiratory syncytial virus

<400> SEQUENCE: 5
atggagttgc taatcctcaa agcaaatgca attaccacaa tcctcactgc agtcacattt      60
tgttttgctt ctggtcaaaa catcactgaa gaatttatc aatcaacatg cagtgcagtt     120
agcaaaggct atcttagtgc tctgagaact ggttggtata ccagtgttat aactatagaa    180
ttaagtaata tcaaggaaaa taagtgtaat ggaacagatg ctaaggtaaa attgataaaa    240
caagaattag ataaatataa aaatgctgta acagaattgc agttgctcat gcaaagcaca    300
ccaccaacaa acaatcgagc cagaagagaa ctaccaaggt ttatgaatta tacactcaac    360
aatgccaaaa aaccaatgt aacattaagc aagaaaagga aagaagatt tcttggtttt    420 ttgttaggtg ttggatctgc aatcgccagt ggcgttgctg tatctaaggt cctgcaccta    480
gaaggggaag tgaacaagat caaaagtgct ctactatcca caaacaaggc tgtagtcagc    540
ttatcaaatg gagttagtgt cttaaccagc aaagtgttag acctcaaaaa ctatatagat    600
aaacaattgt tacctattgt gaacaagcaa agctgcagca tatcaaatat agaaactgtg    660
atagagttcc aacaaaagaa caacagacta ctagagatta ccagggaatt tagtgttaat    720
gcaggtgtaa ctacacctgt aagcacttac atgttaacta atagtgaatt attgtcatta    780
atcaatgata tgcctataac aaatgatcag aaaaagttaa tgtccaacaa tgttcaaata    840
gttagacagc aaagttactc tatcatgtcc ataataaaag aggaagtctt agcatatgta    900
gtacaattac cactatatgg tgttatagat acaccctgtt ggaaactaca cacatcccct    960
ctatgtacaa ccaacacaaa agaagggtcc aacatctgtt aacaagaac tgacagagga   1020 tggtactgtg acaatgcagg atcagtatct ttcttcccac aagctgaaac atgtaaagtt   1080
caatcaaatc gagtattttg tgacacaatg aacagtttaa cattaccaag tgaaataaat   1140
ctctgcaatg ttgacatatt caaccccaaa tatgattgta aaattatgac ttcaaaaaca   1200
gatgtaagca gctccgttat cacatctcta ggagccattg tgtcatgcta tggcaaaact   1260
aaatgtacag catccaataa aaatcgtgga atcataaaga catttttctaa cgggtgcgat   1320 tatgtatcaa ataagggat ggacactgtg tctgtaggta cacattata ttatgtaaat   1380 aagcaagaag gtaaaagtct ctatgtaaaa ggtgaaccaa taataaattt ctatgaccca   1440
ttagtattcc cctctgatga atttgatgca tcaatatctc aagtcaacga gaagattaac   1500
cagagcctag catttattcg taaatccgat gaattattac ataatgtaaa tgctggtaaa   1560
tccaccacaa atatcatgat aactactata attatagtga ttatagtaat attgttatca   1620
ttaattgctg ttggactgct cttatactgt aaggccagaa gcacaccagt cacactaagc   1680
aaagatcaac tgagtggtat aaataatatt gcatttagta actaa                  1725

<210> SEQ ID NO 6
<211> LENGTH: 1698
<212> TYPE: DNA
<213> ORGANISM: Influenza A virus

<400> SEQUENCE: 6
```

| | |
|---|---|
| atgaaggcaa acctactggt cctgttatgt gcacttgcag ctgcagatgc agacacaata | 60 |
| tgtataggct accatgcgaa caattcaacc gacactgttg acacagtact cgagaagaat | 120 |
| gtgacagtga cacactctgt taacctgctc gaagacagcc acaacggaaa actatgtaga | 180 |
| ttaaaaggaa tagccccact acaattgggg aaatgtaaca tcgccggatg gctcttggga | 240 |
| aacccagaat gcgacccact gcttccagtg agatcatggt cctacattgt agaaacacca | 300 |
| aactctgaga atggaatatg ttatccagga gatttcatcg actatgagga gctgagggag | 360 |
| caattgagct cagtgtcatc attcgaaaga ttcgaaatat ttcccaaaga aagctcatgg | 420 |
| cccaaccaca cacaaacgg agtaacggca gcatgctccc atgaggggaa aagcagtttt | 480 |
| tacagaaatt tgctatggct gacggagaag gagggctcat acccaaagct gaaaaattct | 540 |
| tatgtgaaca aaaagggaa agaagtcctt gtactgtggg gtattcatca cccgcctaac | 600 |
| agtaaggaac aacagaatct ctatcagaat gaaaatgctt atgtctctgt agtgacttca | 660 |
| aattataaca ggagatttac cccggaaata gcagaaagac ccaaagtaag agatcaagct | 720 |
| gggaggatga actattactg gaccttgcta aaacccggag acacaataat atttgaggca | 780 |
| aatggaaatc taatagcacc aatgtatgct ttcgcactga gtagaggctt tgggtccggc | 840 |
| atcatcacct caaacgcatc aatgcatgag tgtaacacga agtgtcaaac accctggga | 900 |
| gctataaaca gcagtctccc ttaccagaat atacacccag tcacaatagg agagtgccca | 960 |
| aaatacgtca ggagtgccaa attgaggatg gttacaggac taaggaacaa tccgtccatt | 1020 |
| caatccagag gtctatttgg agccattgcc ggttttattg aaggggatg gactggaatg | 1080 |
| atagatggat ggtatggtta tcatcatcag aatgaacagg gatcaggcta tgcagcggat | 1140 |
| caaaaagca cacaaaatgc cattaacggg attacaaaca aggtgaacac tgttatcgag | 1200 |
| aaaatgaaca ttcaattcac agctgtgggt aaagaattca acaaattaga aaaaggatg | 1260 |
| gaaaatttaa ataaaaagt tgatgatgga tttctggaca tttggacata taatgcagaa | 1320 |
| ttgttagttc tactggaaaa tgaaaggact ctggatttcc atgactcaaa tgtgaagaat | 1380 |
| ctgtatgaga agtaaaaaag ccaattaaag aataatgcca agaaatcgg aaatggatgt | 1440 |
| tttgagttct accacaagtg tgacaatgaa tgcatggaaa gtgtaagaaa tgggacttat | 1500 |
| gattatccca atattcaga agagtcaaag ttgaacaggg aaaaggtaga tggagtgaaa | 1560 |
| ttggaatcaa tggggatcta tcagattctg gcgatctact caactgtcgc cagttcactg | 1620 |
| gtgcttttgg tctccctggg ggcaatcagt ttctggatgt gttctaatgg atctttgcag | 1680 |
| tgcagaatat gcatctga | 1698 |

<210> SEQ ID NO 7
<211> LENGTH: 1725
<212> TYPE: DNA
<213> ORGANISM: Artificial Sequence
<220> FEATURE:
<223> OTHER INFORMATION: GC-enriched DNA coding sequence coding for the Fusion (F) protein of RSV Long

<400> SEQUENCE: 7

| | |
|---|---|
| atggagctgc ccatcctcaa ggccaacgcc atcaccacca tcctggcggc cgtgacgttc | 60 |
| tgcttcgcca gctcccagaa catcaccgag gagttctacc agagcacctg ctccgccgtc | 120 |
| agcaagggct acctgtccgc cctccggacc gggtggtaca cgagcgtgat caccatcgag | 180 |
| ctgtccaaca tcaaggagaa caagtgcaac ggcaccgacg cgaaggtgaa gctgatcaac | 240 |
| caggagctcg acaagtacaa gaacgccgtc accgagctgc agctgctcat gcagagcacg | 300 |

| accgccgcca | acaaccgcgc | gcggcgcgag | ctgccgcggt | tcatgaacta | caccctgaac | 360 |
| aacaccaaga | agacgaacgt | gaccctctcc | aagaagcgca | agcggcgctt | cctggggttc | 420 |
| ctgctcggcg | tggggagcgc | catcgcctcc | ggcatcgccg | tcagcaaggt | gctgcacctg | 480 |
| gagggcgagt | gaacaagat | caagtccgcc | ctcctgagca | ccaacaaggc | ggtcgtgtcc | 540 |
| ctgagcaacg | gggtgtccgt | cctcaccagc | aaggtgctgg | acctgaagaa | ctacatcgac | 600 |
| aagcagctcc | tgcccatcgt | gaacaagcag | tcctgccgga | tcagcaacat | cgagacgggtc | 660 |
| atcgagttcc | agcagaagaa | caaccgcctg | ctcgagatca | cccgggagtt | cagcgtgaac | 720 |
| gccggcgtga | ccaccccgt | ctccacgtac | atgctgacca | cagcgagct | gctctccctg | 780 |
| atcaacgaca | tgcccatcac | caacgaccag | aagaagctga | tgagcaacaa | cgtgcagatc | 840 |
| gtgcgccagc | agtcctacag | catcatgtcc | atcatcaagg | aggaggtcct | cgcctacgtg | 900 |
| gtgcagctgc | cgctgtacgg | ggtcatcgac | acccctgct | ggaagctcca | cacgagcccc | 960 |
| ctgtgcacca | ccaacaccaa | ggagggctcc | aacatctgcc | tgacgcggac | cgaccgcggg | 1020 |
| tggtactgcg | acaacgccgg | cagcgtgtcc | ttcttcccc | aggccgagac | ctgcaaggtc | 1080 |
| cagagcaacc | gggtgttctg | cgacaccatg | aactccctca | cgctgccgag | cgaggtgaac | 1140 |
| ctgtgcaacg | tcgacatctt | caaccccaag | tacgactgca | agatcatgac | ctccaagacc | 1200 |
| gacgtgagct | ccagcgtgat | cacctccctc | ggcgcgatcg | tcagctgcta | cggaagacg | 1260 |
| aagtgcaccg | ccagcaacaa | gaaccgcggc | atcatcaaga | ccttctccaa | cgggtgcgac | 1320 |
| tacgtgagca | acaagggcgt | ggacaccgtc | tccgtgggca | acaccctgta | ctacgtgaac | 1380 |
| aagcaggagg | ggaagagcct | gtacgtcaag | ggcgagccca | tcatcaactt | ctacgacccc | 1440 |
| ctcgtgttcc | cgtccgacga | gttcgacgcc | agcatctccc | aggtgaacga | gaagatcaac | 1500 |
| cagagcctgg | ccttcatccg | gaagtccgac | gagctgctgc | accacgtcaa | cgccgggaag | 1560 |
| agcacgacca | acatcatgat | caccaccatc | atcatcgtga | tcatcgtgat | cctcctgtcc | 1620 |
| ctgatcgcgg | tcggcctcct | gctgtactgc | aaggcccgca | gcacgccgt | gaccctctcc | 1680 |
| aaggaccagc | tgagcgggat | caacaacatc | gccttctcca | actga | | 1725 |

<210> SEQ ID NO 8
<211> LENGTH: 1725
<212> TYPE: DNA
<213> ORGANISM: Artificial Sequence
<220> FEATURE:
<223> OTHER INFORMATION: GC-enriched DNA coding sequence coding for the Fusion (F) protein of RSV A2

<400> SEQUENCE: 8

| atggagctgc | tcatcctgaa | ggccaacgcc | atcaccacca | tcctgacggc | ggtgaccttc | 60 |
| tgcttcgcca | gcggcagaa | catcaccgag | gagttctacc | agtccacctg | cagcgccgtc | 120 |
| tccaaggggt | acctcagcgc | cctgcggacg | ggctggtaca | cctccgtgat | caccatcgag | 180 |
| ctgagcaaca | tcaaggagaa | caagtgcaac | gggaccgacg | ccaaggtgaa | gctcatcaag | 240 |
| caggagctgg | acaagtacaa | gaacgcggtc | acggagctgc | agctcctgat | gcagtccacc | 300 |
| ccgccgacca | caaccgcgc | ccggcgcgag | ctgccccggt | tcatgaacta | caccctcaac | 360 |
| aacgccaaga | agacgaacgt | gaccctgagc | aagaagcgca | agcggcgctt | cctggggcttc | 420 |
| ctcctggggg | tgggctccgc | catcgcgagc | ggcgtcgccg | tgtccaaggt | gctgcacctc | 480 |
| gagggggagt | caacaagat | caagagcgcc | ctgctgtcca | ccaacaaggc | cgtggtgagc | 540 |
| ctctccaacg | gcgtcagcgt | gctgacctcc | aaggtgctgg | acctcaagaa | ctacatcgac | 600 |

-continued

```
aagcagctgc tgcccatcgt caacaagcag agctgctcca tcagcaacat cgagacggtg    660
atcgagttcc agcagaagaa caaccggctc ctggagatca cccgcgagtt cagcgtgaac    720
gccggggtca ccacccccgt gtccacgtac atgctgacca acagcgagct cctgtccctg    780
atcaacgaca tgccgatcac caacgaccag aagaagctca tgagcaacaa cgtgcagatc    840
gtccggcagc agtcctacag catcatgtcc atcatcaagg aggaggtgct ggcgtacgtg    900
gtccagctgc cctctacgg cgtgatcgac accccctgct ggaagctgca cacgagcccc    960
ctgtgcacca ccaacaccaa ggaggggtcc aacatctgcc tcacgcgcac cgaccggggc   1020
tggtactgcg acaacgccgg cagcgtctcc ttcttcccgc aggccgagac ctgcaaggtg   1080
cagagcaacc gcgtgttctg cgacaccatg aactccctga cgctgcccag cgagatcaac   1140
ctctgcaacg tcgacatctt caaccccaag tacgactgca agatcatgac ctccaagacc   1200
gacgtgagct ccagcgtgat cacctccctg ggggccatcg tcagctgcta cggcaagacg   1260
aagtgcaccg ccagcaacaa gaaccggggg atcatcaaga ccttctccaa cggctgcgac   1320
tacgtgagca acaagggcat ggacaccgtg tccgtcggga acaccctgta ctacgtgaac   1380
aagcaggagg gcaagagcct ctacgtgaag gggggagccca tcatcaactt ctacgacccg   1440
ctggtcttcc cctccgacga gttcgacgcg agcatctccc aggtgaacga gaagatcaac   1500
cagagcctgg ccttcatccg caagtccgac gagctgctcc acaacgtgaa cgccggcaag   1560
agcacgacca acatcatgat caccaccatc atcatcgtca tcatcgtgat cctgctgtcc   1620
ctcatcgccg tggggctgct gctctactgc aaggcccgga gcacgcccgt caccctgtcc   1680
aaggaccagc tgagcggcat caacaacatc gcgttctcca actga                   1725
```

<210> SEQ ID NO 9
<211> LENGTH: 1725
<212> TYPE: DNA
<213> ORGANISM: Artificial Sequence
<220> FEATURE:
<223> OTHER INFORMATION: GC-enriched DNA coding sequence coding for the Fusion (F) protein of RSV A2 (P102A)

<400> SEQUENCE: 9

```
atggagctgc tcatcctgaa ggccaacgcc atcaccacca tcctgacggc ggtgaccttc     60
tgcttcgcca gcggccagaa catcaccgag gagttctacc agtccacctg cagcgccgtc    120
tccaaggggt acctcagcgc cctgcggacg ggctggtaca cctccgtgat caccatcgag    180
ctgagcaaca tcaaggagaa caagtgcaac gggaccgacg ccaaggtgaa gctcatcaag    240
caggagctgg acaagtacaa gaacgcggtc acggagctgc agctcctgat gcagtccacc    300
ccggcgacca acaaccgcgc ccggcgcgag ctgccccggt tcatgaacta caccctcaac    360
aacgccaaga agacgaacgt gaccctgagc aagaagcgca agcggcgctt cctgggcttc    420
ctcctggggg tgggctccgc catcgcgagc ggcgtcgccg tgtccaaggt gctgcacctc    480
gagggggagg tcaacaagat caagagcgcc ctgctgtcca ccaacaaggc cgtggtgagc    540
ctctccaacg gcgtcagcgt gctgacctcc aaggtgctgg acctcaagaa ctacatcgac    600
aagcagctgc tgcccatcgt caacaagcag agctgctcca tcagcaacat cgagacggtg    660
atcgagttcc agcagaagaa caaccggctc ctggagatca cccgcgagtt cagcgtgaac    720
gccggggtca ccacccccgt gtccacgtac atgctgacca acagcgagct cctgtccctg    780
atcaacgaca tgccgatcac caacgaccag aagaagctca tgagcaacaa cgtgcagatc    840
gtccggcagc agtcctacag catcatgtcc atcatcaagg aggaggtgct ggcgtacgtg    900
```

```
gtccagctgc ccctctacgg cgtgatcgac acccccctgct ggaagctgca cacgagcccc    960
ctgtgcacca ccaacaccaa ggaggggtcc aacatctgcc tcacgcgcac cgaccggggc   1020
tggtactgcg acaacgccgg cagcgtctcc ttcttcccgc aggccgagac ctgcaaggtg   1080
cagagcaacc gcgtgttctg cgacaccatg aactccctga cgctgcccag cgagatcaac   1140
ctctgcaacg tcgacatctt caaccccaag tacgactgca agatcatgac ctccaagacc   1200
gacgtgagct ccagcgtgat cacctccctg ggggccatcg tcagctgcta cggcaagacg   1260
aagtgcaccg ccagcaacaa gaaccggggg atcatcaaga ccttctccaa cggctgcgac   1320
tacgtgagca acaagggcat ggacaccgtg tccgtcggga cacccctgta ctacgtgaac   1380
aagcaggagg gcaagagcct ctacgtgaag ggggagccca tcatcaactt ctacgacccg   1440
ctggtcttcc cctccgacga gttcgacgcg agcatctccc aggtgaacga gaagatcaac   1500
cagagcctgg ccttcatccg caagtccgac gagctgctcc acaacgtgaa cgccggcaag   1560
agcacgacca acatcatgat caccaccatc atcatcgtca tcatcgtgat cctgctgtcc   1620
ctcatcgccg tggggctgct gctctactgc aaggcccgga gcacgcccgt caccctgtcc   1680
aaggaccagc tgagcggcat caacaacatc gcgttctcca actga                   1725

<210> SEQ ID NO 10
<211> LENGTH: 1725
<212> TYPE: DNA
<213> ORGANISM: Artificial Sequence
<220> FEATURE:
<223> OTHER INFORMATION: GC-enriched DNA coding sequence coding for the
      Fusion (F) protein of RSV A2 (I379V)

<400> SEQUENCE: 10
atggagctgc tcatcctgaa ggccaacgcc atcaccacca tcctgacggc ggtgaccttc     60
tgcttcgcca gcggccagaa catcaccgag gagttctacc agtccacctg cagcgccgtc    120 tccaagggt acctcagcgc cctgcggacg ggctggtaca cctccgtgat caccatcgag    180
ctgagcaaca tcaaggagaa caagtgcaac gggaccgacg ccaaggtgaa gctcatcaag    240
caggagctgg acaagtacaa gaacgcggtc acggagctgc agctcctgat gcagtccacc    300
ccgccgacca acaaccgcgc ccggcgcgag ctgccccggt tcatgaacta ccccctcaac    360
aacgccaaga gacgaacgt gacccctgagc aagaagcgca agcggcgctt cctgggcttc    420
ctcctggggg tgggctccgc catcgcgagc ggcgtcgccg tgtccaaggt gctgcacctc    480
gagggggagg tcaacaagat caagagcgcc ctgctgtcca ccaacaaggc cgtggtgagc    540
ctctccaacg gcgtcagcgt gctgacctcc aaggtgctgg acctcaagaa ctacatcgac    600
aagcagctgc tgcccatcgt caacaagcag agctgctcca tcagcaacat cgagacggtg    660
atcgagttcc agcagaagaa caaccggctc ctggagatca cccgcgagtt cagcgtgaac    720
gccggggtca ccacccccgt gtccacgtac atgctgacca cagcgagct cctgtccctg    780 atcaacgaca tgccgatcac caacgaccag aagaagctca tgagcaacaa cgtgcagatc    840
gtccggcagc agtcctacag catcatgtcc atcatcaagg aggaggtgct ggcgtacgtg    900
gtccagctgc ccctctacgg cgtgatcgac acccccctgct ggaagctgca cacgagcccc    960
ctgtgcacca ccaacaccaa ggaggggtcc aacatctgcc tcacgcgcac cgaccggggc   1020
tggtactgcg acaacgccgg cagcgtctcc ttcttcccgc aggccgagac ctgcaaggtg   1080
cagagcaacc gcgtgttctg cgacaccatg aactccctga cgctgcccag cgaggtcaac   1140
ctctgcaacg tcgacatctt caaccccaag tacgactgca agatcatgac ctccaagacc   1200
```

```
gacgtgagct ccagcgtgat cacctccctg ggggccatcg tcagctgcta cggcaagacg    1260
aagtgcaccg ccagcaacaa gaaccggggg atcatcaaga ccttctccaa cggctgcgac    1320
tacgtgagca acaagggcat ggacaccgtg tccgtcggga cacccctgta ctacgtgaac    1380
aagcaggagg gcaagagcct ctacgtgaag ggggagccca tcatcaactt ctacgacccg    1440
ctggtcttcc cctccgacga gttcgacgcg agcatctccc aggtgaacga gaagatcaac    1500
cagagcctgg ccttcatccg caagtccgac gagctgctcc acaacgtgaa cgccggcaag    1560
agcacgacca acatcatgat caccaccatc atcatcgtca tcatcgtgat cctgctgtcc    1620
ctcatcgccg tggggctgct gctctactgc aaggcccgga gcacgcccgt caccctgtcc    1680
aaggaccagc tgagcggcat caacaacatc gcgttctcca actga                    1725
```

<210> SEQ ID NO 11
<211> LENGTH: 1725
<212> TYPE: DNA
<213> ORGANISM: Artificial Sequence
<220> FEATURE:
<223> OTHER INFORMATION: GC-enriched DNA coding sequence coding for the
      Fusion (F) protein of RSV A2 (M447V)

<400> SEQUENCE: 11

```
atggagctgc tcatcctgaa ggccaacgcc atcaccacca tcctgacggc ggtgaccttc      60
tgcttcgcca gcggccagaa catcaccgag gagttctacc agtccaccag cagcgccgtc     120
tccaaggggt acctcagcgc cctgcggacg ggctggtaca cctccgtgat caccatcgag     180
ctgagcaaca tcaaggagaa caagtgcaac gggaccgacg ccaaggtgaa gctcatcaag     240
caggagctgg acaagtacaa gaacgcggtc acggagctgc agctcctgat gcagtccacc     300
ccgccgacca caaccgcgc ccggcgcgag ctgccccggt tcatgaacta cacccctcaac     360 aacgccaaga gacgaacgt gaccctgagc aagaagcgca gcggcgcctt cctgggcttc     420
ctcctggggg tgggctccgc catcgcgagc ggcgtcgccg tgtccaaggt gctgcacctc     480
gagggggagg tcaacaagat caagagcgcc ctgctgtcca ccaacaaggc cgtggtgagc     540
ctctccaacg gcgtcagcgt gctgacctcc aaggtgctgg acctcaagaa ctacatcgac     600
aagcagctgc tgcccatcgt caacaagcag agctgctcca tcagcaacat cgagacggtg     660
atcgagttcc agcagaagaa caaccggctc ctggagatca cccgcgagtt cagcgtgaac     720
gccggggtca ccacccccgt gtccacgtac atgctgacca cagcgagct cctgtccctg     780 atcaacgaca tgccgatcac caacgaccag aagaagctca tgagcaacaa cgtgcagatc     840
gtccggcagc agtcctacag catcatgtcc atcatcaagg aggaggtgct ggcgtacgtg     900
gtccagctgc ccctctacgg cgtgatcgac accccctgct ggaagctgca cacgagcccc     960
ctgtgcacca ccaacaccaa ggagggtcc aacatctgcc tcacgcgcac cgaccggggc    1020
tggtactgcg acaacgccgg cagcgtctcc ttcttcccgc aggccgagac ctgcaaggtg    1080
cagagcaacc gcgtgttctg cgacaccatg aactccctga cgctgcccag cgagatcaac    1140
ctctgcaacg tcgacatctt caaccccaag tacgactgca agatcatgac ctccaagacc    1200
gacgtgagct ccagcgtgat cacctccctg ggggccatcg tcagctgcta cggcaagacg    1260
aagtgcaccg ccagcaacaa gaaccggggg atcatcaaga ccttctccaa cggctgcgac    1320
tacgtgagca acaagggcgt ggacaccgtg tccgtcggga cacccctgta ctacgtgaac    1380
aagcaggagg gcaagagcct ctacgtgaag ggggagccca tcatcaactt ctacgacccg    1440
ctggtcttcc cctccgacga gttcgacgcg agcatctccc aggtgaacga gaagatcaac    1500
```

| cagagcctgg | ccttcatccg | caagtccgac | gagctgctcc | acaacgtgaa | cgccggcaag | 1560 |
| agcacgacca | acatcatgat | caccaccatc | atcatcgtca | tcatcgtgat | cctgctgtcc | 1620 |
| ctcatcgccg | tggggctgct | gctctactgc | aaggcccgga | gcacgcccgt | caccctgtcc | 1680 |
| aaggaccagc | tgagcggcat | caacaacatc | gcgttctcca | actga | | 1725 |

<210> SEQ ID NO 12
<211> LENGTH: 1698
<212> TYPE: DNA
<213> ORGANISM: Artificial Sequence
<220> FEATURE:
<223> OTHER INFORMATION: GC-enriched DNA coding sequence coding for the
      Hemagglutinin (HA) protein of Influenza A/Puerto Rico/8/1934

<400> SEQUENCE: 12

| atgaaggcca | acctgctcgt | gctgctgtgc | gccctcgcgg | ccgccgacgc | cgacaccatc | 60 |
| tgcatcggct | accacgccaa | caacagcacc | gacacggtcg | acaccgtgct | ggagaagaac | 120 |
| gtgaccgtca | cccactccgt | gaacctgctc | gaggacagcc | acaacgggaa | gctgtgccgg | 180 |
| ctgaagggca | tcgcgcccct | ccagctgggg | aagtgcaaca | tcgccggctg | gctgctcggg | 240 |
| aacccggagt | gcgaccccct | gctgccgtg | cgctcctgga | gctacatcgt | cgagacgccc | 300 |
| aactccgaga | acggcatctg | ctacccgggc | gacttcatcg | actacgagga | gctccgggag | 360 |
| cagctgagct | ccgtgagctc | cttcgagcgc | ttcgagatct | tccccaagga | gagctcctgg | 420 |
| cccaaccaca | caccaacgg | ggtgaccgcc | gcctgcagcc | acgagggcaa | gtccagcttc | 480 |
| taccggaacc | tgctctggct | gaccgagaag | gaggggtcct | accccaagct | gaagaacagc | 540 |
| tacgtcaaca | agaagggcaa | ggaggtgctc | gtgctgtggg | ggatccacca | cccgcccaac | 600 |
| tccaaggagc | agcagaacct | gtaccagaac | gagaacgcgt | acgtcagcgt | ggtgacgtcc | 660 |
| aactacaacc | gccggttcac | ccccgagatc | gccgagcgcc | ccaaggtccg | ggaccaggcc | 720 |
| ggccgcatga | actactactg | gacctcctg | aagccgggcg | acaccatcat | cttcgaggcc | 780 |
| aacgggaacc | tgatcgcccc | gatgtacgcg | ttcgccctca | gccggggctt | cgggagcggc | 840 |
| atcatcacgt | ccaacgccag | catgcacgag | tgcaacacca | agtgccagac | ccccctgggc | 900 |
| gccatcaact | ccagcctgcc | ctaccagaac | atccacccgg | tgaccatcgg | ggagtgcccc | 960 |
| aagtacgtgc | gctccgccaa | gctccggatg | gtcacgggcc | tgcgcaacaa | ccccagcatc | 1020 |
| cagtcccggg | ggctgttcgg | cgcgatcgcc | gggttcatcg | agggcggctg | gaccgggatg | 1080 |
| atcgacggct | ggtacgggta | ccaccaccag | aacgagcagg | gcagcgggta | cgccgccgac | 1140 |
| cagaagtcca | cccagaacgc | catcaacggc | atcaccaaca | aggtgaacac | ggtgatcgag | 1200 |
| aagatgaaca | tccagttcac | cgcggtcggc | aaggagttca | acaagctcga | aagcgcatg | 1260 |
| gagaacctga | acaagaaggt | ggacgacggg | ttcctggaca | tctggaccta | caacgccgag | 1320 |
| ctcctggtgc | tgctcgagaa | cgagcggacc | ctggacttcc | acgacagcaa | cgtcaagaac | 1380 |
| ctgtacgaga | aggtgaagtc | ccagctcaag | aacaacgcca | aggagatcgg | caacgggtgc | 1440 |
| ttcgagttct | accacaagtg | cgacaacgag | tgcatggaga | gcgtccgcaa | cggcacgtac | 1500 |
| gactacccca | gtactccga | ggagagcaag | ctgaaccggg | agaaggtgga | cggggtgaag | 1560 |
| ctggagtcca | tgggcatcta | ccagatcctc | gccatctaca | gcaccgtcgc | ctccagcctg | 1620 |
| gtgctgctgg | tgtccctcgg | cgcgatcagc | ttctggatgt | gcagcaacgg | gtccctgcag | 1680 |
| tgccgcatct | gcatctga | | | | | 1698 |

<210> SEQ ID NO 13

<211> LENGTH: 1725
<212> TYPE: RNA
<213> ORGANISM: Artificial Sequence
<220> FEATURE:
<223> OTHER INFORMATION: GC-enriched RNA sequence without UTRs coding
for the Fusion (F) protein of RSV Long

<400> SEQUENCE: 13

| auggagcugc ccauccucaa ggccaacgcc aucaccacca uccuggcggc cgugacguuc | 60 |
| ugcuucgcca gcucccagaa caucaccgag gaguucuacc agagcaccug cuccgccguc | 120 |
| agcaagggcu accuguccgc ccuccggacc ggguggauaca cgagcgugau caccaucgag | 180 |
| cuguccaaca ucaaggagaa caagugcaac ggcaccgacg cgaaggugaa gcugaucaac | 240 |
| caggagcucg acaaguacaa gaacgccguc accgagcugc agcugcucau gcagagcacg | 300 |
| accgccgcca caaccgcgc gcggcgcgag cugccgcggu ucaugaacua cacccugaac | 360 |
| aacaccaaga gacgaacgu gacccucucc aagaagcgca gcggcgcuu ccuggggguc | 420 |
| cugcucggcg uggggagcgc caucgccucc ggcaucgccg ucagcaaggu gcugcaccug | 480 |
| gagggcgagg ugaacaagau caaguccgcc cuccugagcc caacaaggc ggucguguc | 540 |
| cugagcaacg ggguguccgu ccucaccagc aaggugcugg accugaagaa cuacaucgac | 600 |
| aagcagcucc ugcccaucgu gaacaagcag uccugccgga ucagcaacau cgagacgguc | 660 |
| aucgaguucc agcagaagaa caaccgccug cucgagauca cccgggaguu cagcgugaac | 720 |
| gccggcguga ccaccccccgu cuccacguac augcugacca cagcgagcu gcucucccug | 780 |
| aucaacgaca ugcccaucac caacgaccag aagaagcuga ugagcaacaa cgugcagauc | 840 |
| gugcgccagc aguccuacag caucaugucc aucaucaagg aggagguccu cgccuacgug | 900 |
| gugcagcugc cgcuguacgg ggucaucgac accccccugcu ggaagcucca cacgagcccc | 960 |
| cugugcacca ccaacaccaa ggagggcucc aacaucugcc ugacgcggac cgaccgcggg | 1020 |
| ugguacugcg acaacgccgg cagcguguccu uucuuccccc aggccgagac cugcaagguc | 1080 |
| cagagcaacc ggguguucug cgacaccaug aacucccuca cgcugccgag cgaggugaac | 1140 |
| cugugcaacg ucgacaucuu caaccccaag uacgacugca gaucaugac cuccaagacc | 1200 |
| gacgugagcu ccagcgugau caccccccuc ggcgcgaucg ucagcugcua cgggaagacg | 1260 |
| aagugcaccg ccagcaacaa gaaccgcggc aucaucaaga ccuucuccaa cgggugcgac | 1320 |
| uacgugagca caagggcgu ggacaccguc uccgugggca cacccuguca ucgugaac | 1380 |
| aagcaggagg ggaagagccu guacgucaag ggcgagccca ucaucaacuu cuacgacccc | 1440 |
| cucguguucc cguccgacga guucgacgcc agcaucuccc aggugaacga gaagaucaac | 1500 |
| cagagccugg ccuucauccg gaaguccgac gagcugcugc accacgucaa cgccgggaag | 1560 |
| agcacgacca caucaugau caccaccauc aucaucguga ucaucgugau ccuccugucc | 1620 |
| cugaucgcgg ucggccuccu gcuguacugc aaggcccgca gcacgccgu gacccucucc | 1680 |
| aaggaccagc ugagcgggau caacaacauc gccuucucca acuga | 1725 |

<210> SEQ ID NO 14
<211> LENGTH: 1725
<212> TYPE: RNA
<213> ORGANISM: Artificial Sequence
<220> FEATURE:
<223> OTHER INFORMATION: GC-enriched RNA sequence without UTRs coding
for the Fusion (F) protein of RSV A2

<400> SEQUENCE: 14

| auggagcugc ucauccugaa ggccaacgcc aucaccacca uccugacggc ggugaccuuc | 60 |

| | |
|---|---|
| ugcuucgcca gcggccagaa caucaccgag gaguucuacc aguccaccug cagcgccguc | 120 |
| uccaaggggu accucagcgc ccugcggacg ggcugguaca ccuccgugau caccaucgag | 180 |
| cugagcaaca ucaaggagaa caagugcaac gggaccgacg ccaaggugaa gcucaucaag | 240 |
| caggagcugg acaaguacaa gaacgcgguc acggagcugc agcuccugau gcaguccacc | 300 |
| ccgccgacca caaccgcgc ccggcgcgag cugccccggu ucaugaacua caccccucaac | 360 |
| aacgccaaga gacgaacgu gacccugagc aagaagcgca agcggcgcuu ccugggcuuc | 420 |
| cuccugggg ugggcuccgc caucgcgagc ggcgucgccg uguccaaggu gcugcaccuc | 480 |
| gaggggagg ucaacaagau caagagcgcc cugcugucca ccaacaaggc cguggugagc | 540 |
| cucuccaacg cgucagcgu gcugaccucc aaggugcugg accucaagaa cuacaucgac | 600 |
| aagcagcugc ugcccaucgu caacaagcag agcugcucca ucagcaacau cgagacggug | 660 |
| aucgaguucc agcagaagaa caaccggcuc cuggagauca cccgcgaguu cagcgugaac | 720 |
| gccggguca ccaccccgu guccacguac augcugacca cagcgagcu ccuguccug | 780 |
| aucaacgaca ugccgaucac caacgaccag aagaagcuca ugagcaacaa cgugcagauc | 840 |
| guccggcagc aguccuacag caucaugucc aucaucaagg aggaggugcu ggcguacgug | 900 |
| guccagcugc cccucuacgg cgugaucgac accccccugcu ggaagcugca cacgagcccc | 960 |
| cugugcacca ccaacaccaa ggaggggucc aacaucugcc ucacgcgcac cgaccggggc | 1020 |
| ugguacugcg acaacgccgg cagcgucucc uucuucccgc aggccgagac cugcaaggug | 1080 |
| cagagcaacc gcguguucug cgacaccaug aacucccuga cgcugcccag cgagaucaac | 1140 |
| cucugcaacg ucgacaucuu caaccccaag uacgacugca agaucaugac cuccaagacc | 1200 |
| gacgugagcu ccagcgugau caccuccccug ggggccaucg ucagcugcua cggcaagacg | 1260 |
| aagugcaccg ccagcaacaa gaaccggggg aucaucaaga ccuucccaa cggcugcgac | 1320 |
| uacgugagca caagggcau ggacaccgug uccgucggga cacccuguca ucgugaac | 1380 |
| aagcaggagg gcaagagccu cuacgugaag ggggagccca ucaucaacuu cuacgacccg | 1440 |
| cuggucuucc ccuccgacga guucgacgcg agcauccccc aggugaacga gaagaucaac | 1500 |
| cagagccugg ccuucauccg caaguccgac gagcugcucc acaacgugaa cgccggcaag | 1560 |
| agcacgacca caucaugau caccaccauc aucaucguca ucaucgugau ccugcugucc | 1620 |
| cucaucgccg uggggcugcu gcucuacgc aaggcccgga gcacgcccgu cacccugucc | 1680 |
| aaggaccagc ugagcggcau caacaacauc gcguucucca acuga | 1725 |

<210> SEQ ID NO 15
<211> LENGTH: 1725
<212> TYPE: RNA
<213> ORGANISM: Artificial Sequence
<220> FEATURE:
<223> OTHER INFORMATION: GC-enriched RNA sequence without UTRs coding
   for the Fusion (F) protein of RSV A2 (P102A)

<400> SEQUENCE: 15

| | |
|---|---|
| auggagcugc ucauccugaa ggccaacgcc aucaccacca uccugacggc ggugaccuuc | 60 |
| ugcuucgcca gcggccagaa caucaccgag gaguucuacc aguccaccug cagcgccguc | 120 |
| uccaaggggu accucagcgc ccugcggacg ggcugguaca ccuccgugau caccaucgag | 180 |
| cugagcaaca ucaaggagaa caagugcaac gggaccgacg ccaaggugaa gcucaucaag | 240 |
| caggagcugg acaaguacaa gaacgcgguc acggagcugc agcuccugau gcaguccacc | 300 |
| ccggcgacca caaccgcgc ccggcgcgag cugccccggu ucaugaacua caccccucaac | 360 |

```
aacgccaaga agacgaacgu gacccugagc aagaagcgca agcggcgcuu ccugggcuuc    420
cuccuggggg ugggcuccgc caucgcgagc ggcgucgccg uguccaaggu gcugcaccuc    480 gaggggagg ucaacaagau caagagcgcc cugcugucca ccaacaaggc cguggugagc     540
cucuccaacg gcgucagcgu gcugaccucc aaggugcugg accuaagaa cuacaucgac     600 aagcagcugc ugcccaucgu caacaagcag agcugcucca ucagcaacau cgagacggug    660
aucgaguucc agcagaagaa caaccggcuc cuggagauca cccgcgaguu cagcgugaac    720
gccgggguca ccaccccgu guccacguac augcugacca acagcgagcu ccugucccug     780
aucaacgaca ugccgaucac caacgaccag aagaagcuca ugagcaacaa cgugcagauc    840
guccggcagc aguccuacag caucaugucc aucaucaagg aggaggugcu ggcguacgug    900
guccagcugc cccucuacgg cgugaucgac accccccugcu ggaagcugca cgagcccc     960 cugugcacca ccaacaccaa ggaggggucc aacaucugcc ucacgcgcac cgaccggggc    1020
ugguacugcg acaacgccgg cagcgucucc uucuucccgc aggccgagac cugcaaggug    1080
cagagcaacc gcguguucug cgacaccaug aacucccuga cgcugcccag cgagaucaac    1140
cucugcaacg ucgacaucuu caaccccaag uacgacugca gaucaugac cuccaagacc     1200 gacgugagcu ccagcgugau caccucccug ggggccaucg ucagcugcua cggcaagacg    1260
aagugcaccg ccagcaacaa gaaccggggg aucaucaaga ccuuccaa cggcugcgac     1320 uacgugagca acaagggcau ggacaccgug uccgucggga cacccugua cuacgugaac     1380 aagcaggagg gcaagagccu cuacgugaag ggggagccca ucaucaacuu cuacgacccg    1440
cuggucuucc ccuccgacga guucgacgcg agcaucuccc aggugaacga gaagaucaac    1500
cagagccugg ccuucauccg caaguccgac gagcugcucc acaacgugaa cgccggcaag    1560
agcacgacca caucaugau caccaccauc aucaucguca ucaucgugau ccugcugucc    1620
cucaucgccg ugggcugcu gcucuacugc aaggcccgga gcacgcccgu caccucgucc    1680
aaggaccagc ugagcggcau caacaacauc gcguuccca acuga                    1725
```

<210> SEQ ID NO 16
<211> LENGTH: 1725
<212> TYPE: RNA
<213> ORGANISM: Artificial Sequence
<220> FEATURE:
<223> OTHER INFORMATION: GC-enriched RNA sequence without UTRs coding
      for the Fusion (F) protein of RSV A2 (I379V)

<400> SEQUENCE: 16

```
auggagcugc ucauccugaa ggccaacgcc aucaccacca uccugacggc ggugaccuuc    60
ugcuucgcca gcggccagaa caucaccgag gaguucuacc aguccaccug cagcgccguc    120
uccaaggggu accucagcgc ccugcgacg ggcuggauaca ccuccgugau caccaucgag    180
cugagcaaca ucaaggagaa caagugcaac gggaccgacg ccaaggugaa gcucaucaag    240
caggagcugg acaaguacaa gaacgcgguc acgagcugc agcuccugau gcaguccacc    300
ccgccgacca caaccgcgc ccggcgcgag cugccccggu ucaugaacua cacccucaac    360
aacgccaaga agacgaacgu gacccugagc aagaagcgca agcggcgcuu ccugggcuuc    420
cuccuggggg ugggcuccgc caucgcgagc ggcgucgccg uguccaaggu gcugcaccuc    480 gaggggagg ucaacaagau caagagcgcc cugcugucca ccaacaaggc cguggugagc     540
cucuccaacg gcgucagcgu gcugaccucc aaggugcugg accuaagaa cuacaucgac     600 aagcagcugc ugcccaucgu caacaagcag agcugcucca ucagcaacau cgagacggug    660
```

| | |
|---|---|
| aucgaguucc agcagaagaa caaccggcuc cuggagauca cccgcgaguu cagcgugaac | 720 |
| gccggguca ccaccccgu guccacguac augcugacca cagcgagcu ccugucccug | 780 |
| aucaacgaca ugccgaucac caacgaccag aagaagcuca ugagcaacaa cgugcagauc | 840 |
| guccggcagc aguccuacag caucaugucc aucaucaagg aggaggugcu ggcguacgug | 900 |
| guccagcugc cccucuacgg cgugaucgac acccccugcu ggaagcugca cacgagcccc | 960 |
| cugugcacca ccaacaccaa ggaggggucc aacaucugcc ucacgcgcac cgaccggggc | 1020 |
| ugguacugcg acaacgccgg cagcgucucc uucuucccgc aggccgagac cugcaaggug | 1080 |
| cagagcaacc gcguguucug cgacaccaug aacccccuga cgcugcccag cgaggucaac | 1140 |
| cucugcaacg ucgacaucuu caaccccaag uacgacgca agaucaugac cuccaagacc | 1200 |
| gacgugagcu ccagcgugau caccucccug ggggccaucg ucagcugcua cggcaagacg | 1260 |
| aagugcaccg ccagcaacaa gaaccggggg aucaucaaga ccuucuccaa cggcugcgac | 1320 |
| uacgugagca caaggggcau ggacaccgug uccgucggga cacccgua cuacgugaac | 1380 |
| aagcaggagg gcaagagccu cuacgugaag ggggagccca ucaucaacuu cuacgacccg | 1440 |
| cuggucuucc ccuccgacga guucgacgcg agcaucuccc aggugaacga gaagaucaac | 1500 |
| cagagccugg ccuucauccg caagucccgac gagcugcucc acaacgugaa cgccggcaag | 1560 |
| agcacgacca acaucaugau caccaccauc aucaucguca ucaucgugau ccugcugucc | 1620 |
| cucaucgccg uggggcugcu gcucuacugc aaggcccgga gcacgccgu cacccugucc | 1680 |
| aaggaccagc ugagcggcau caacaacauc gcguucucca acuga | 1725 |

<210> SEQ ID NO 17
<211> LENGTH: 1725
<212> TYPE: RNA
<213> ORGANISM: Artificial Sequence
<220> FEATURE:
<223> OTHER INFORMATION: GC-enriched RNA sequence without UTRs coding
      for the Fusion (F) protein of RSV A2 (M447V)

<400> SEQUENCE: 17

| | |
|---|---|
| auggagcugc ucauccugaa ggccaacgcc aucaccacca uccugacggc ggugaccuuc | 60 |
| ugcuucgcca gcggccagaa caucaccgag gaguucuacc aguccaccug cagcgccguc | 120 |
| uccaaggggu accucagcgc ccugcggacg ggcugguaca ccuccgugau caccaucgag | 180 |
| cugagcaaca ucaaggagaa caagugcaac gggaccgacg ccaaggugaa gcucaucaag | 240 |
| caggagcugg acaaguacaa gaacgcgguc acggagcugc agcuccugau gcagucacc | 300 |
| ccgccgacca caaccgcgc ccggcgcgag cugcccggu ucaugaacua cacccucaac | 360 |
| aacgccaaga gacgaacgu gacccugagc aagaagcgca agcggcgcuu ccugggcuuc | 420 |
| cuccuggggg ugggcuccgc caucgcgagc ggcgucgccg uguccaaggu gcugcaccuc | 480 |
| gagggggagg ucaacaagau caagagcgcc cugcugucca ccaacaaggc cguggugagc | 540 |
| cucuccaacg gcgucagcgu gcugaccucc aaggugcugg accuaagaa cuacaucgac | 600 |
| aagcagcugc ugcccaucgu caacaagcag agcugcucca ucagcaacau cgagacggug | 660 |
| aucgaguucc agcagaagaa caaccggcuc cuggagauca cccgcgaguu cagcgugaac | 720 |
| gccggguca ccaccccgu guccacguac augcugacca cagcgagcu ccugucccug | 780 |
| aucaacgaca ugccgaucac caacgaccag aagaagcuca ugagcaacaa cgugcagauc | 840 |
| guccggcagc aguccuacag caucaugucc aucaucaagg aggaggugcu ggcguacgug | 900 |
| guccagcugc cccucuacgg cgugaucgac acccccugcu ggaagcugca cacgagcccc | 960 |

```
cugugcacca ccaacaccaa ggaggggucc aacaucugcc ucacgcgcac cgaccggggc    1020
ugguacugcg acaacgccgg cagcgucucc uucuucccgc aggccgagac cugcaaggug    1080
cagagcaacc gcguguucug cgacaccaug aacucccuga cgcugcccag cgagaucaac    1140
cucugcaacg ucgacaucuu caaccccaag uacgacugca agaucaugac cuccaagacc    1200
gacgugagcu ccagcgugau caccucccug ggggccaucg ucagcugcua cggcaagacg    1260
aagugcaccg ccagcaacaa gaaccggggg aucaucaaga ccuucccaa cggcugcgac     1320 uacgugagca acaagggcgu ggacaccgug uccgucggga acacccugua cuacgugaac    1380
aagcaggagg gcaagagccu cuacgugaag ggggagccca ucaucaacuu cuacgacccg    1440
cuggucuucc ccuccgacga guucgacgcg agcaucuccc aggugaacga gaagaucaac    1500
cagagccugg ccuucauccg caaguccgac gagcugcucc acaacgugaa cgccggcaag    1560
agcacgacca acaucaugau caccaccauc aucaucguca ucaucgugau ccugcuguCC    1620
cucaucgccg uggggcugcu gcucuacugc aaggcccgga gcacgcccgu caccccuguCC   1680 aaggaccagc ugagcggcau caacaacauc gcguucucca acuga                    1725

<210> SEQ ID NO 18
<211> LENGTH: 1698
<212> TYPE: RNA
<213> ORGANISM: Artificial Sequence
<220> FEATURE:
<223> OTHER INFORMATION: GC-enriched RNA sequence without UTRs coding
      for the Hemagglutinin (HA) protein of Influenza A/Puerto
      Rico/8/1934

<400> SEQUENCE: 18
augaaggcca accugcucgu gcugcugugc gcccucgcgg ccgccgacgc cgacaccauc      60
ugcaucggcu accacgccaa caacagcacc gacacggucg acaccgugcu ggagaagaac    120
gugaccguca cccacuccgu gaaccugcuc gaggacagcc acaacgggaa gcugugccgg    180
cugaagggca ucgcgccccu ccagcugggg aagugcaaca ucgccggcug gcugcucggg    240
aacccggagu gcgacccccu gcugcccgug cgcuccugga gcuacaucgu cgagacgccc    300
aacuccgaga acggcaucug cuacccgggc gacuucaucg acuacgagga gcuccgggag    360
cagcugagcu ccgugagcuc cuucgagcgc uucgagaucu uccccaagga gagcuccugg    420
cccaaccaca caccaacgg ggugaccgcc gccugcagcc acgagggcaa guccagcuuc    480
uaccggaacc ugcucuggcu gaccgagaag gaggggyuccu acccaagcu gaagaacagc    540 uacgucaaca agaagggcaa ggaggugcuc gugcuguggg ggauccacca cccgcccaac    600
uccaaggagc agcagaaccu guaccagaac gagaacgcgu acgucagcgu ggugacgucc    660
aacuacaacc gccgguucac ccccgagauc gccgagcgcc caagguccgg gaccaggcc     720 ggccgcauga cuacuacug gacccuccug aagccgggcg acaccaucau cuucgaggcc    780
aacgggaacc ugaucgcccc gauguacgcg uucgcccuca gccggggcuu cgggagcggc    840
aucaucacgu ccaacgccag caugcacgag ugcaacacca gugccagac ccccuggc     900 gccaucaacu ccagccugcc cuaccagaac auccacccgg ugaccaucgg ggagugcccc    960
aaguacgugc gcuccgccaa gcuccggaug ucacggggcc ugcgcaacaa ccccagcauc   1020
cagucccggg ggcuguucgg cgcgaucgcc ggguucaucg agggcggcug gaccgggaug   1080
aucgacggcu gguacgggua ccaccaccag aacgagcagg gcagcgggua cgccgccgac   1140
cagaagucca cccagaacgc caucaacggc aucaccaaca ggugaacac ggugaucgag    1200
```

```
aagaugaaca uccaguucac cgcggucggc aaggaguuca acaagcucga gaagcgcaug    1260
gagaaccuga acaagaaggu ggacgacggg uuccuggaca ucuggaccua caacgccgag    1320
cuccuggugc ugcucgagaa cgagcggacc cuggacuucc acgacagcaa cgucaagaac    1380
cuguacgaga aggugaaguc ccagcucaag aacaacgcca aggagaucgg caacgggugc    1440
uucgaguucu accacaagug cgacaacgag ugcauggaga gcguccgcaa cggcacguac    1500
gacuacccca aguacuccga ggagagcaag cugaaccggg agaaggugga cggggugaag    1560
cuggaguuca ugggcaucua ccagauccuc gccaucuaca gcaccgucgc cuccagccug    1620
gugcugcugg uguccucgg cgcgaucagc uucggaugu gcagcaacgg gucccugcag    1680
ugccgcaucu gcaucuga                                                  1698
```

<210> SEQ ID NO 19
<211> LENGTH: 1942
<212> TYPE: RNA
<213> ORGANISM: Artificial Sequence
<220> FEATURE:
<223> OTHER INFORMATION: GC-enriched full mRNA sequence coding for the
      Fusion (F) protein of RSV Long

<400> SEQUENCE: 19

```
gggagaaagc uuaccaugga gcugcccauc ucaaggcca acgccaucac caccauccug     60
gcggccguga cguucugcuu cgccagcucc cagaacauca ccgaggaguu cuaccagagc    120
accugcuccg ccgucagcaa gggcuaccug uccgcccucc ggaccggug guacacgagc    180 gugaucacca ucgagcuguc caacaucaag gagaacaagu gcaacggcac cgacgcgaag    240
gugaagcuga ucaaccagga gcucgacaag uacaagaacg ccgucaccga gcugcagcug    300
cucaugcaga gcacgaccgc cgccaacaac cgcgcgcggc gcgagcugcc gcgguucaug    360
aacuacaccc ugaacaacac caagaagacg aacgugaccc ucuccaagaa gcgcaagcgg    420
cgcuuccugg gguccugcu cggcgugggg agcgccaucg ccuccggcau cgccgucagc    480
aaggugcugc accuggaggg cgaggugaac aagaucaagu ccgcccuccu gagcaccaac    540
aaggcggucg uguccugag caacggggug uccguccuca ccagcaaggu gcuggaccug    600
aagaacuaca ucgacaagca gcuccugccc aucgugaaca agcaguccug ccggaucagc    660
aacaucgaga cggucaucga guuccagcag aagaacaacc gccugcucga gaucacccgg    720
gaguucagcg ugaacgccgg cgugaccacc cccgucucca cguacaugcu gaccaacagc    780
gagcugcucu cccugaucaa cgacaugccc aucaccaacg accagaagaa gcugaugagc    840
aacaacgugc agaucgugcg ccagcagucc uacagcauca ugucaaucau caaggaggag    900
guccucgccu acgugguggc agcugccgcu acggggguca ucgacacccc cugcuggaag    960
cuccacacga gccccugug caccaccaac accaaggagg cuccaacau cugccugacg   1020 cggaccgacc gcggguggua cugcgacaac gccggcagcg uguccuucuu ccccccaggcc   1080 gagaccugca agguccagag caaccgggug uucugcgaca ccaugaacuc ccucacgcug   1140
ccgagcgagg ugaaccugug caacgucgac aucuucaacc ccaaguacga cugcaagauc   1200
augacccuca agaccgacgu gagcuccagc gugaucaccu cccucggcgc gaucgucagc   1260
ugcuacggga agacgaagug caccgccagc aacaagaacc gcggcaucau caagaccuuc   1320
uccaacgggu gcgacuacgu gagcaacaag ggcguggaca ccgucuccgu gggcaacacc   1380
cuguacuacg ugaacaagca ggagggggaag agccuguacg ucaagggcga gcccaucauc   1440
aacuucuacg accccccucgu guucccgucc gacgaguucg acgccagcau cucccaggug   1500
```

| aacgagaaga ucaaccagag ccuggccuuc auccggaagu ccgacgagcu gcugcaccac | 1560 |
| gucaacgccg ggaagagcac gaccaacauc augaucacca ccaucaucau cgugaucauc | 1620 |
| gugauccucc ugucccugau cgcggucggc cuccugcugu acugcaaggc ccgcagcacg | 1680 |
| cccgugaccc ucuccaagga ccagcugagc gggaucaaca caucgccuu uccaacuga | 1740 |
| ggacuaguua uaagacugac uagcccgaug ggccucccaa cgggcccucc ucccucccuu | 1800 |
| gcaccgagau uaauaaaaaa aaaaaaaaaa aaaaaaaaaa aaaaaaaaaa aaaaaaaaaa | 1860 |
| aaaaaaaaaa aaaaaaaaug cauccccccc cccccccccc cccccccccc cccaaaggc | 1920 |
| ucuuuucaga gccaccagaa uu | 1942 |

<210> SEQ ID NO 20
<211> LENGTH: 1942
<212> TYPE: RNA
<213> ORGANISM: Artificial Sequence
<220> FEATURE:
<223> OTHER INFORMATION: GC-enriched full mRNA sequence coding for the
      Fusion (F) protein of RSV A2

<400> SEQUENCE: 20

| gggagaaagc uuaccaugga gcugcucauc cugaaggcca acgccaucac caccauccug | 60 |
| acggcgguga ccuucugcuu cgccagcggc cagaacauca ccgaggaguu cuaccagucc | 120 |
| accugcagcg ccgucuccaa gggguaccuc agcgcccugc ggacgggcug guacaccucc | 180 |
| gugaucacca ucgagcugag caacaucaag gagaacaagu gcaacgggac cgacgccaag | 240 |
| gugaagcuca ucaagcagga gcuggacaag uacaagaacg cggucacgga gcugcagcuc | 300 |
| cugaugcagu ccaccccgcc gaccaacaac cgcgcccggc gcgagcugcc ccgguucaug | 360 |
| aacuacaccc ucaacaacgc caagaagacg aacgugaccc ugagcaagaa cgcaagcgg | 420 |
| cgcuuccugg gcuuccuccu gggggugggc uccgccaucg cgagcggcgu cgccguguc | 480 |
| aaggugcugc accucgaggg ggaggucaac aagaucaaga cgcccugcu guccaccaac | 540 |
| aaggccgugg ugagccucuc caacggcguc agcgugcuga ccuccaaggu gcuggaccuc | 600 |
| aagaacuaca ucgacaagca gcugcugccc aucgucaaca gcagagcug cuccaucagc | 660 |
| aacaucgaga cggugaucga guuccagcag aagaacaacc ggcuccugga gaucacccgc | 720 |
| gaguucagcg ugaacgccgg ggucaccacc cccgugucca cguacaugcu gaccaacagc | 780 |
| gagcuccugu cccugaucaa cgacaugccg aucaccaacg accagaagaa gcucaugagc | 840 |
| aacaacgugc agaucguccg gcagcaguc uacagcauca ugucacau caaggaggag | 900 |
| gugcuggcgu acgugguca gcugcccuc uacggcguga ucgacccccc ugcuggaag | 960 |
| cugcacacga gccccgugug caccaccaac accaaggagg ggucaacau cugccucacg | 1020 |
| cgcaccgacc ggggcuggua cugcgacaac gccggcagcg ucccuucucu cccgcaggcc | 1080 |
| gagaccugca aggugcagag caaccgcgug uucugcgaca ccaugaacuc ccugacgcug | 1140 |
| cccagcgaga ucaaccucug caacgucgac aucuucaacc caaguacga cugcaagauc | 1200 |
| augaccucca agaccgacgu gagcuccagc gugaucaccu cccgggggc caucgucagc | 1260 |
| ugcuacggca agacgaagug caccgccagc aacaagaacc gggggaucau caagaccuuc | 1320 |
| uccaacggcu gcgacuacgu gagcaacaag ggcauggaca ccgugucgu cgggaacacc | 1380 |
| cuguacuacg ugaacaagca ggagggcaag agccucuacg ugaaggggga gcccaucauc | 1440 |
| aacuucuacg acccgcuggu cuucccccuc gacgaguucg acgcgagcau cucccagguc | 1500 |
| aacgagaaga ucaaccagag ccuggccuuc auccggaagu ccgacgagcu gcuccacaac | 1560 |

```
gugaacgccg gcaagagcac gaccaacauc augaucacca ccaucaucau cgucaucauc    1620
gugauccugc ugucccucau cgccgugggg cugcugcucu acugcaaggc ccggagcacg    1680
cccgucaccc uguccaagga ccagcugagc ggcaucaaca acaucgcguu cuccaacuga    1740
ggacuaguua uaagacugac uagcccgaug ggccucccaa cgggcccucc uccccuccuu    1800
gcaccgagau uaauaaaaaa aaaaaaaaaa aaaaaaaaaa aaaaaaaaaa aaaaaaaaaa    1860
aaaaaaaaaa aaaaaaaaug cauccccccc cccccccccc cccccccccc cccaaaggc     1920 ucuuuucaga gccaccagaa uu                                             1942
```

<210> SEQ ID NO 21
<211> LENGTH: 1915
<212> TYPE: RNA
<213> ORGANISM: Artificial Sequence
<220> FEATURE:
<223> OTHER INFORMATION: GC-enriched full mRNA sequence coding for the
      Hemagglutinin (HA) protein of Influenza A/Puerto Rico/8/1934

<400> SEQUENCE: 21

```
gggagaaagc uuaccaugaa ggccaaccug cucgugcugc ugugcgcccu cgcggccgcc    60
gacgccgaca ccaucugcau cggcuaccac gccaacaaca gcaccgacac ggucgacacc    120
gugcuggaga agaacgugac cgucacccac uccgugaacc ugcucgagga cagccacaac    180
gggaagcugu gccggcugaa gggcaucgcg ccccuccagc uggggaagug caacaucgcc    240
ggcuggcugc ucgggaaccc ggagugcgac ccccugcugc ccgugcgcuc cuggagcuac    300
aucgucgaga cgcccaacuc cgagaacggc aucugcuacc cggcgacuu caucgacuac    360 gaggagcucc gggagcagcu gagcuccgug agcuccuucg agcgcuucga gaucuucccc    420
aaggagagcu ccuggcccaa ccacaacacc aacgggguga ccgccgccug cagccacgag    480
ggcaagucca gcuucuaccg gaaccugcuc uggcugaccg agaaggaggg guccuacccc    540
aagcugaaga cagcuacgu caacaagaag ggcaaggagg ugcucgugcu guggggauc    600 caccacccgc ccaacuccaa ggagcagcag aaccuguacc agaacgagaa cgcguacguc    660
agcguggugu cguccaacua caaccgccgg uucaccccgg agaucgccga gcgccccaag    720
guccgggacc aggccggccg caugaacuac uacuggaccc uccugaagcc gggcgacacc    780
aucaucuucg aggccaacgg gaaccugauc gccccgaugu acgcguucgc ccucagccgg    840
ggcuucggga cgcaucau cacguccaac gccagcaugc acgagugcaa caccaagugc    900
cagacccccc ugggcgccau caacuccagc cugcccuacc agaacaucca cccggugacc    960
aucggggagu gccccaagua cgugcgcucc gccaagcucc ggaugucac gggccugcgc    1020 aacaaccccg cauccaguc ccgggggcug uucggcgcga ucgccgggu caucgagggc    1080 ggcuggaccg gaugaucga cggcugguac ggguaccacc accagaacga gcagggcagc    1140 gggacgccg ccgaccagaa guccacccag aacgccauca cggcaucac caacaaggug    1200 aacacgguga ucgagaagau gaacauccag uucaccgcgg ucggcaagga guucaacaag    1260
cucgagaagc gcauggagaa ccugaacaag aaggugacg acgggunucu ggacaucugg    1320
accuacaacg ccgagcuccu ggugcugcuc gagaacgagc ggacccugga cuuccacgac    1380
agcaacguca gaaccugua cgagaaggug aagucccagc ucaagaacaa cgccaaggag    1440
aucggcaacg ggugcuucga guucuaccac aagugcgaca acgagugcau ggagagcguc    1500
cgcaacggca cguacgacua ccccaaguac uccgaggaga gcaagcugaa ccggagaag    1560 guggacgggg ugaagcugga guccaugggc aucuaccaga uccucgccau cuacagcacc    1620
```
gucgccucca gccuggugcu gcuggugucc cucggcgcga ucagcuucug gaugugcagc 1680
aacgggaccc ugcagugccg caucugcauc ugaccacuag uuauaagacu gacuagcccg 1740
augggccucc caacgggccc uccuccccuc cuugcaccga gauuaauaaa aaaaaaaaaa 1800
aaaaaaaaaa aaaaaaaaaa aaaaaaaaaa aaaaaaaaaa aaaaaaaaaa augcaucccc 1860
cccccccccc cccccccccc cccccccaaa ggcucuuuuc agagccacca gaauu 1915

<210> SEQ ID NO 22
<211> LENGTH: 9
<212> TYPE: PRT
<213> ORGANISM: Influenza A virus

<400> SEQUENCE: 22

Tyr Pro Tyr Asp Val Pro Asp Tyr Ala
1 5

<210> SEQ ID NO 23
<211> LENGTH: 547
<212> TYPE: RNA
<213> ORGANISM: Artificial sequence
<220> FEATURE:
<223> OTHER INFORMATION: Non-coding RNA used as a control

<400> SEQUENCE: 23
gggagaaagc ucaagcuugg agcaaugccc gcacauugag gaaaccgagu ugcauaucuc 60
agaguauugg cccccgugua gguuauucuu gacagacagu ggagcuuauu cacucccagg 120
auccgagucg cauacuacgg uacuggugac agaccuaggu cgucaguuga ccaguccgcc 180
acuagacgug aguccgucaa agcaguuaga uguuacacuc uauuagaucu cggauuacag 240
cuggaaggag caggaguagu guucuugcuc uaaguaccga gugugcccaa uacccgauca 300
gcuuauuaac gaacggcucc uccucuuaga cugcagcgua agugcggaau cuggggauca 360
aauuacugac ugccuggauu acccucggac auauaaccuu guagcacgcu guugcuguau 420
aggugaccaa cgcccacucg aguagaccag cucucuuagu ccggacaaug auaggaggcg 480
cggucaaucu acuucuggcu aguuaagaau aggcugcacc gaccucuaua aguagcgugu 540
ccucuag 547

<210> SEQ ID NO 24
<211> LENGTH: 9
<212> TYPE: PRT
<213> ORGANISM: respiratory syncytial virus

<400> SEQUENCE: 24

Lys Tyr Lys Asn Ala Val Thr Glu Leu
1 5

<210> SEQ ID NO 25
<211> LENGTH: 10
<212> TYPE: PRT
<213> ORGANISM: respiratory syncytial virus

<400> SEQUENCE: 25

Thr Tyr Met Leu Thr Asn Ser Glu Leu Leu
1 5 10

```
<210> SEQ ID NO 26
<211> LENGTH: 9
<212> TYPE: PRT
<213> ORGANISM: respiratory syncytial virus

<400> SEQUENCE: 26

Phe Pro Gln Ala Glu Thr Cys Lys Val
1               5
```

The invention claimed is:

1. A cytotoxic T cell-inducing immunogenic composition comprising:
   i) at least a first mRNA comprising a protein coding sequence encoding at least the extracellular domain of a human respiratory syncytial virus (RSV) Fusion protein (F) antigen, said RSV-F antigen comprising an amino acid sequence encoding the T-cell epitopes of SEQ ID NOs: 24, 25 and 26; and
   ii) at least a second mRNA comprising a protein coding sequence encoding at least the extracellular domain of a human influenza virus Hemagglutinin (HA) protein.

2. The immunogenic composition of claim 1, wherein the first and second mRNAs comprise 5' Cap structures.

3. The immunogenic composition of claim 2, wherein the first and second mRNAs comprise poly-A sequence of about 50 to about 250 adenosine nucleotides.

4. The immunogenic composition of claim 3, wherein the first and second mRNAs comprise 5' and/or 3' UTR sequences.

5. The immunogenic composition of claim 4, wherein the protein coding sequence of the first and second mRNAs is modified to increase the G/C content.

6. The immunogenic composition of claim 4, wherein the first and second mRNAs are complexed with a cationic or polycationic compound.

7. The immunogenic composition of claim 6, wherein the first and second mRNAs are complexed with a cationic or polycationic protein.

8. The immunogenic composition of claim 6, wherein the first and second mRNAs are complexed with a cationic lipid.

9. The immunogenic composition of claim 4, wherein the HA protein is a full-length HA protein.

10. The immunogenic composition of claim 4, wherein the F protein is a full-length HA protein.

11. The immunogenic composition of claim 4, wherein the HA protein is an Influenza A HA protein.

12. The immunogenic composition of claim 11, wherein the Influenza A HA protein is from H1N1, H1N2, H3N1, H3N2, H3N8, H5N1, H5N2, H5N3, H5N8, H5N9, H7N1, H7N2, H7N3, H7N4, H7N7, H9N1, H9N2 or H10N7 Influenza.

13. The immunogenic composition of claim 12, wherein the Influenza A HA protein is H1 HA protein.

14. The immunogenic composition of claim 4, wherein the HA protein is an Influenza B HA protein.

15. The immunogenic composition of claim 4, wherein the composition comprises a further mRNA encoding a further antigen.

16. The immunogenic composition of claim 15, wherein the further antigen is an Influenza HA protein.

17. The immunogenic composition of claim 5, wherein the first and second mRNAs are complexed with a cationic lipid.

18. The immunogenic composition of claim 17, wherein the HA protein is an Influenza A HA protein.

19. The immunogenic composition of claim 18, wherein the HA protein is a full-length HA protein.

20. The immunogenic composition of claim 17, wherein the first mRNA encodes a RSV F protein comprising least the extracellular domain and the transmembrane domain of the RSV F protein.

21. The immunogenic composition of claim 4, wherein the HA protein is from a H1N1 virus.

22. The immunogenic composition of claim 21, wherein upon intradermal or intramuscular injection to a mammal the composition induces a cytotoxic T cell response to the amino acid epitope of SEQ ID NOs: 24, 25 and/or 26.

23. The immunogenic composition of claim 22, wherein upon intradermal or intramuscular injection to a mammal the composition induces a cytotoxic T cell response to the amino acid epitope of SEQ ID NO: 24.

24. The immunogenic composition of claim 22, wherein the first and second mRNAs are complexed with a cationic or polycationic compound.

* * * * *

UNITED STATES PATENT AND TRADEMARK OFFICE
CERTIFICATE OF CORRECTION

| | | |
|---|---|---|
| PATENT NO. | : 12,337,031 B2 | Page 1 of 1 |
| APPLICATION NO. | : 17/590173 | |
| DATED | : June 24, 2025 | |
| INVENTOR(S) | : Karl-Josef Kallen et al. | |

It is certified that error appears in the above-identified patent and that said Letters Patent is hereby corrected as shown below:

On the Title Page

In Item (71) Applicant, delete "CureVac AG" and insert --CureVac SE-- therefor.

Signed and Sealed this
Sixteenth Day of September, 2025

Coke Morgan Stewart
*Acting Director of the United States Patent and Trademark Office*